United States Patent [19]

Yoshida et al.

[11] 4,210,767
[45] * Jul. 1, 1980

[54] 2,2,3-TRIMETHYL-3-CYCLOPENTEN-1-YLALKENYL AND ALKYLIDENE SECONDARY ALKANOLS, ALKANONES, CYCLOALKANOLS AND CYCLOALKANONES, ORGANOLEPTIC USES THEREOF IN PERFUME COMPOSITIONS, COLOGNES AND PERFUMED ARTICLES AND PROCESS FOR PRODUCING SAME

[75] Inventors: Takao Yoshida, West Long Branch; Braja D. Mookherjee, Holmdel; Venkatesh Kamath, Red Bank; John B. Hall, Rumson; William I. Taylor, Summit; Frederick L. Schmitt, Holmdel, all of N.J.

[73] Assignee: International Flavors & Fragrances Inc., New York, N.Y.

[*] Notice: The portion of the term of this patent subsequent to Sep. 25, 1996, has been disclaimed.

[21] Appl. No.: 23,442

[22] Filed: Mar. 23, 1979

Related U.S. Application Data

[62] Division of Ser. No. 932,677, Aug. 10, 1978, Pat. No. 4,169,109.

[51] Int. Cl.$^2$ .................... C07C 45/00; C07C 29/00
[52] U.S. Cl. .................... 568/345; 568/816; 568/838
[58] Field of Search .................... 260/586 C, 593 R; 568/862; 508/802, 816

[56] References Cited

U.S. PATENT DOCUMENTS

| | | | |
|---|---|---|---|
| 2,245,567 | 6/1941 | Brant et al. | 260/593 R |
| 2,549,508 | 4/1951 | Matter | 260/586 C |
| 3,316,303 | 4/1967 | Merlzweiler et al. | 260/586 C |
| 4,081,481 | 3/1978 | Sprecker | 260/586 C |
| 4,107,099 | 8/1978 | Hedge | 568/862 |
| 4,165,339 | 8/1979 | Reichle | 260/586 C |

OTHER PUBLICATIONS

Fieser et al., Reagents for Organic Synthesis, p. 1050 (1965).

*Primary Examiner*—Norman Morgenstern
*Assistant Examiner*—James H. Reamer
*Attorney, Agent, or Firm*—Arthur L. Liberman; Franklin D. Wolffe

[57] ABSTRACT

Described are perfume and fragrance compositions and perfumed articles including soaps, detergents, powders as well as colognes containing 2,2,3-trimethyl-3-cyclopenten-1-ylalkenyl and alkylidene secondary alkanols, alkanones, cycloalkanols and cycloalkanones having the generic structure:

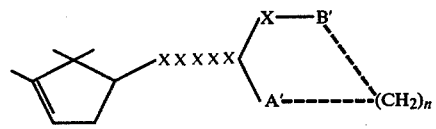

wherein one of the lines + + + + + is a carbon-carbon double bond and the other of the lines + + + + is a carbon-carbon single bond; wherein X is carbinol having the structure:

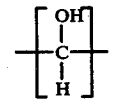

or carbonyl having the structure

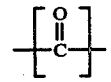

wherein A' is hydrogen, CH$_3$, C$_2$H$_5$ or —CH$_2$—; wherein B' is hydrogen, CH$_3$, C$_2$H$_5$ or —CH$_2$—; where n is 0, 1 or 2; wherein each of the dashed lines are the same and each represents a carbon-carbon single bond or no bond; wherein A' and B' are both —CH$_2$— when n is 1 or 2 and the dashed line is a carbon-carbon single bond or A' is hydrogen and B' is C$_2$H$_5$ or CH$_3$ or both A' and B' are each CH$_3$ or A' is C$_2$H$_5$ and B' is CH$_3$ when n is 0 and the dashed line represents no bond, which imparts thereto rich, musky, cedar woody, sandalwood, sweet, floral, ionone-like, soft-fruity (apricot), green and earthy aromas with resinous topnotes and nutty oily nuances. Also described is a process for preparing such compounds according to the reaction schemes:

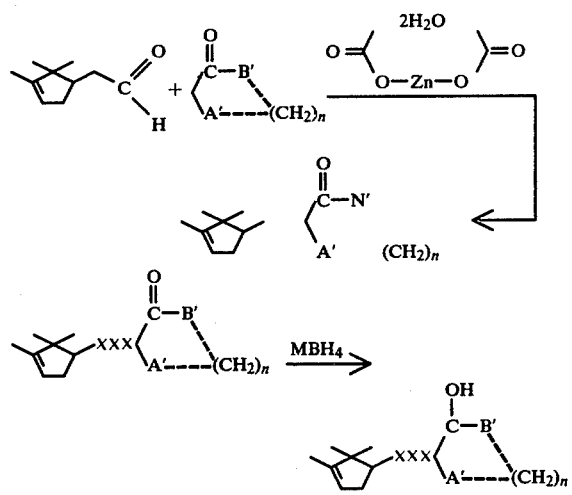

wherein the lines + + + + A', B', the dashed lines and n are as defined above wherein M is alkaline metal.

8 Claims, 45 Drawing Figures

GLC PROFILE FOR EXAMPLE I(A)

GLC PROFILE FOR EXAMPLE I(A)

IR SPECTRUM FOR EXAMPLE I(A).

GLC PROFILE FOR EXAMPLE I(A).

NMR SPECTRUM FOR EXAMPLE IB

IR SPECTRUM FOR EXAMPLE IB.

NMR SPECTRUM FOR EXAMPLE IB.

IR SPECTRUM FOR EXAMPLE IB.

NMR SPECTRUM FOR EXAMPLE IB.

IR SPECTRUM FOR EXAMPLE IB.

NMR SPECTRUM FOR EXAMPLE IB.

GLC PROFILE FOR EXAMPLE I(C).

NMR SPECTRUM FOR EXAMPLE I (C), PEAK C.

IR SPECTRUM FOR EXAMPLE I (C), PEAK C.

NMR SPECTRUM FOR EXAMPLE I (C), PEAK D.

IR SPECTRUM FOR EXAMPLE I (C), PEAK D.

NMR SPECTRUM FOR EXAMPLE I (C), PEAK E.

IR SPECTRUM FOR EXAMPLE I (C), PEAK E.

NMR SPECTRUM FOR EXAMPLE I (C), PEAK F.

IR SPECTRUM FOR EXAMPLE I (C), PEAK F.

GLC PROFILE, EXAMPLE II(A)

GLC PROFILE, EXAMPLE II(A) FRACTION 3.

GLC PROFILE, EXAMPLE II(B).

NMR SPECTRUM FOR EXAMPLE II (B), FRACTION 2.

NMR SPECTRUM FOR EXAMPLE III (A), PEAK A.

FIG.29
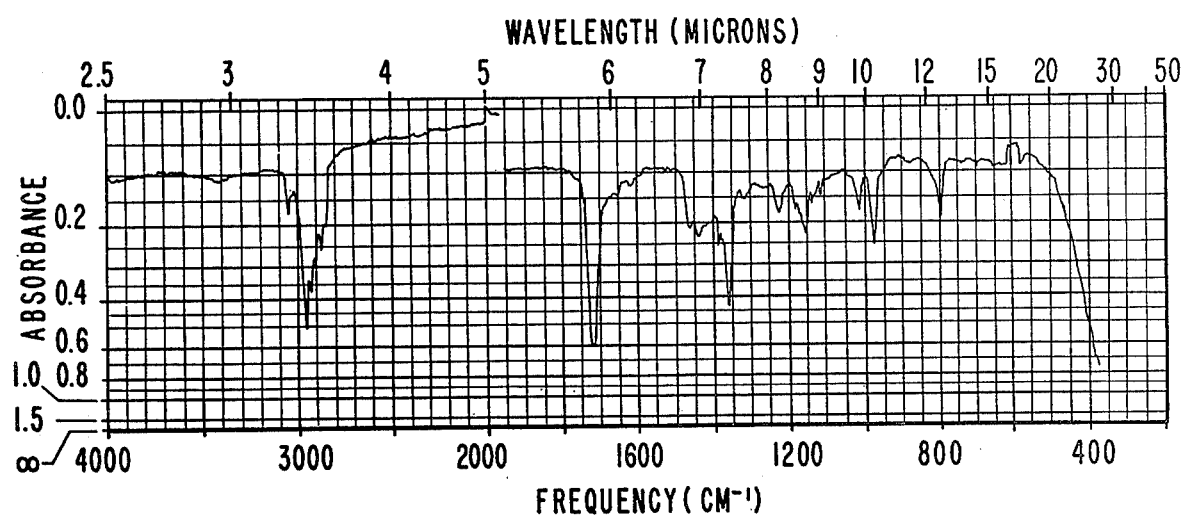
IR SPECTRUM FOR EXAMPLE III (A), PEAK A.
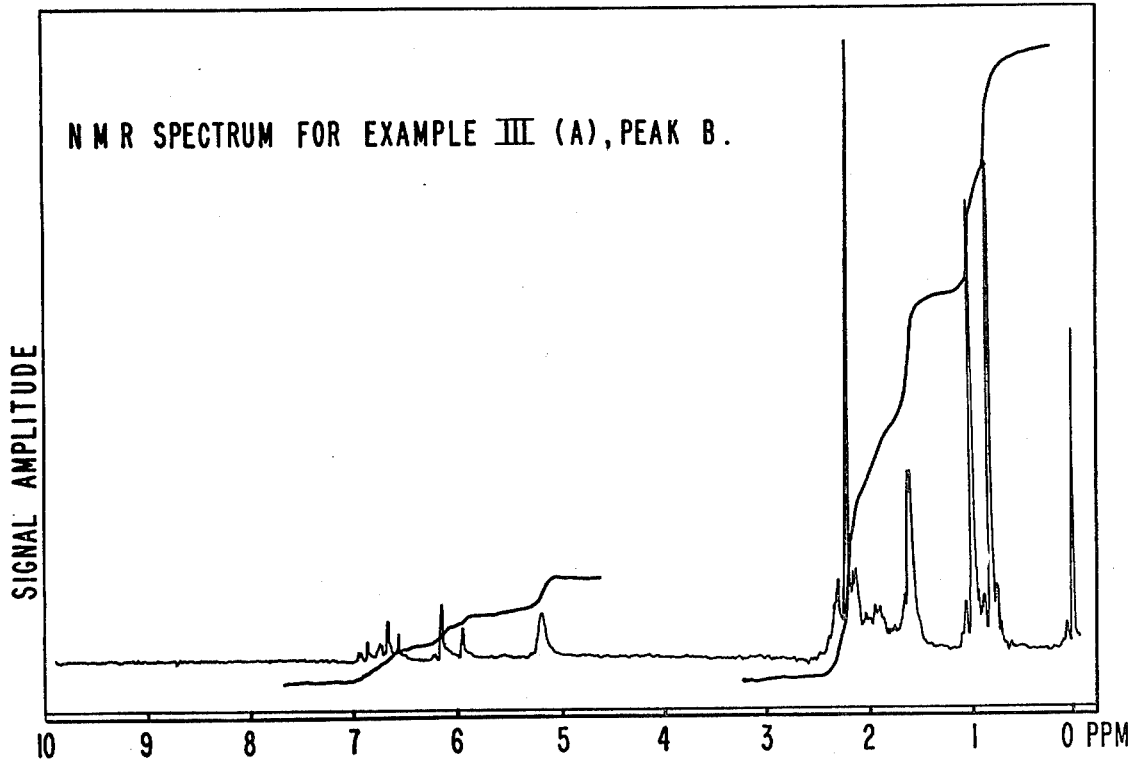
FIG.30

FIG. 31
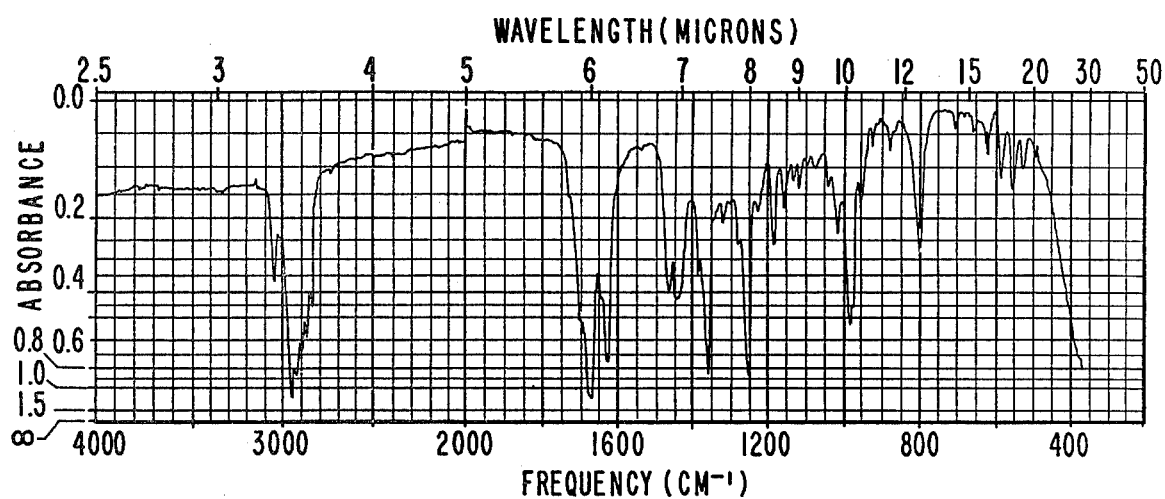
IR SPECTRUM FOR EXAMPLE III (A), PEAK B.
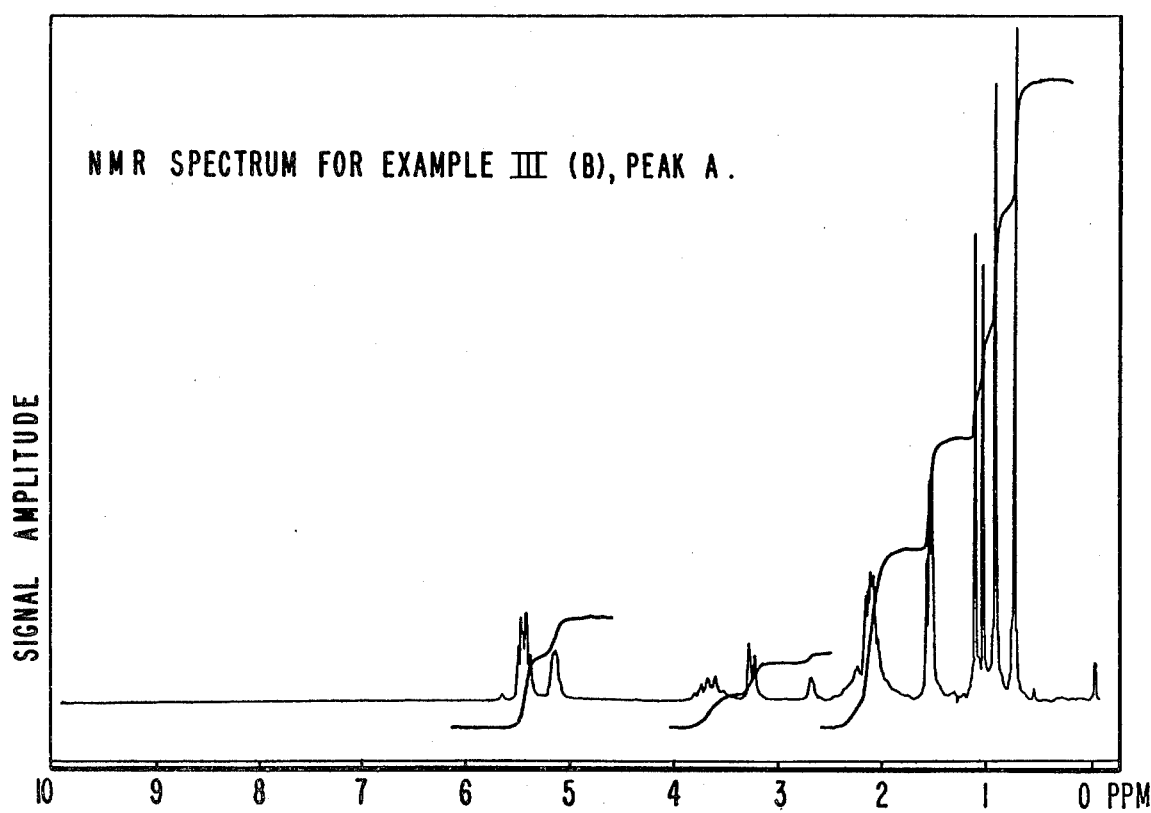
NMR SPECTRUM FOR EXAMPLE III (B), PEAK A.
FIG. 32

IR SPECTRUM FOR EXAMPLE III (B), PEAK B.

GLC PROFILE FOR EXAMPLE IV (A).

IR SPECTRUM FOR EXAMPLE IV (A), PEAK A.

NMR SPECTRUM FOR EXAMPLE IV (A), PEAK A.

IR SPECTRUM FOR EXAMPLE IV(A), PEAK B.

GLC PROFILE FOR EXAMPLE IV(B).

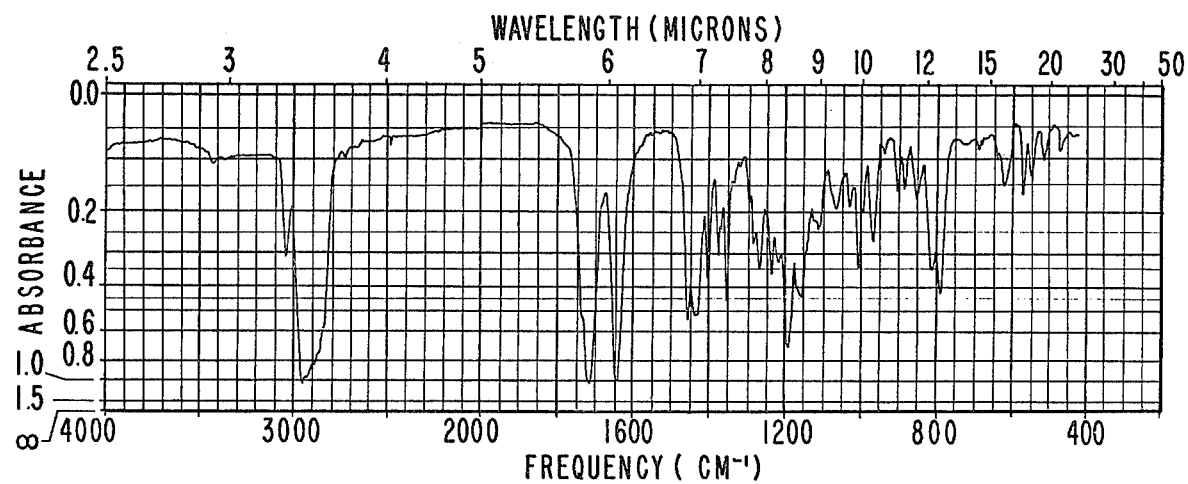
IR SPECTRUM FOR EXAMPLE V(A).
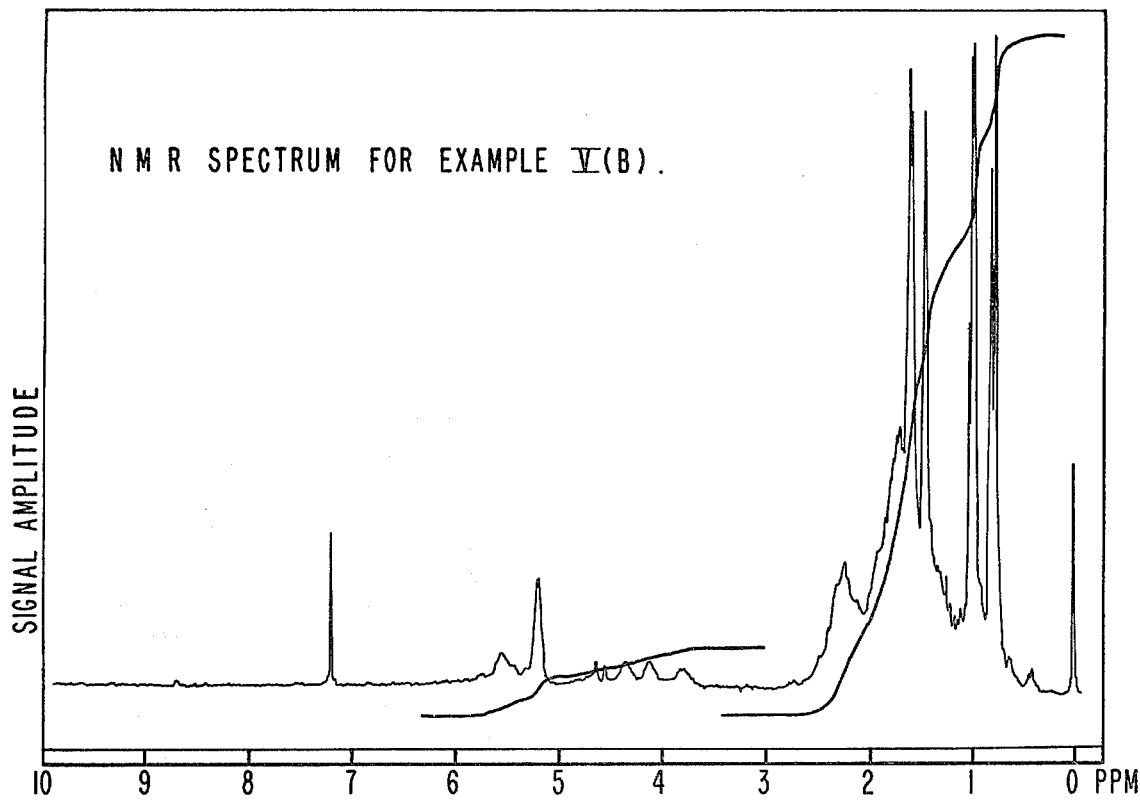

IR SPECTRUM FOR EXAMPLE V(B).

2,2,3-TRIMETHYL-3-CYCLOPENTEN-1-YLALKENYL AND ALKYLIDENE SECONDARY ALKANOLS, ALKANONES, CYCLOALKANOLS AND CYCLOALKANONES, ORGANOLEPTIC USES THEREOF IN PERFUME COMPOSITIONS, COLOGNES AND PERFUMED ARTICLES AND PROCESS FOR PRODUCING SAME

This is a divisional of application Ser. No. 932,677, filed Aug. 10, 1978 now U.S. Pat. No. 4,169,109.

BACKGROUND OF THE INVENTION

There is a continuing search for materials having desirable fragrance properties. Such materials are used either to replace costly natural materials or to provide new fragrances of perfumed types which have not heretofore been available. Especially desirable qualities for substances having interesting fragrances such as sandalwood-type fragrances are stability and persistence, paticularly in a wide variety of perfumed articles (e.g. soaps, detergents and powders) perfumed compositions and colognes, ease of manufacture and intensity of aroma.

Furthermore, according to Guenther [E. Guenther, "The Essential Oils", Vol. V. page 173, D. Van Nostrand Co., Inc., New York (1952)], East Indian sandalwood oil "has been perhaps one of the most precious perfumery materials from antiquity down to modern times, and its popularity has shown no signs of waning." This oil is widely used in perfumery, and would be even more widely used except for its limited supply and high cost.

As is well known, a need exists for synthetic substances which can be used as sandalwood substitutes or extenders. It would be most desirable to be able to synthetically provide the major odorant compounds of the natural sandalwood oil, i.e. alpha-santalol and beta-santalol, but no commercially feasible route to these chemicals is known at this time.

It would be even more desirable to provide a synthetic compound which would have many of the desirable odor qualities of a fine East Indian sandalwood oil, yet not have the potentially labile primary allylic alcohol group present in the natural santalols. A compound which would be more resistant to acidic or oxidative decomposition as well as being base stable could be even more versatile than sandalwood oil itself.

There is no obvious explanation why only slight chemical changes should have such a dramatic effect on odor intensity other than to invoke the general unreliability of odor structure relationships. Why the addition or removal of a methyl group, the removal of a double bond or the mere moving of a methyl group would essentially destroy more than 90% of the odor intensity rather than merely cause subtle odor differences comparable to the subtle chemical differences cannot be explained by any theoretical concepts in the known art.

U.S. Pat. No. 4,052,341, issued on Oct. 4, 1977 provides a sandalwood type aroma imparting material having one of the structures:

TABLE I

| Name | Structure |
|---|---|
| 3-Methyl-5-(2,2,3-trimethylcyclopent-3-en-1-yl)pentan-2-ol | 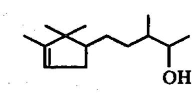 |
| 3-Methyl-5-(2,2,3-trimethylcyclopentan-1-yl)pentan-2-ol | 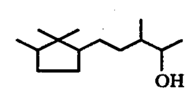 |
| 5-(2,2,3-Trimethylcyclopent-3-en-1-yl)pentan-2-ol | |
| 6-(2,2,3-Trimethylcyclopent-3-en-1-yl)hexan-3-ol | |
| 4-Methyl-6-(2,2,3-trimethylcyclopent-3-en-1-yl)hexan-3-ol | 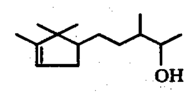 |
| 3-Ethyl-5-(2,2,3-trimethylcyclopent-3-en-1-yl)pentan-2-ol | 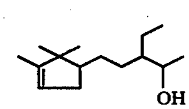 |
| 3-Methyl-5-(2,3,3-trimethylcyclopent-3-en-1-(R)-yl)pentan-2-ol | 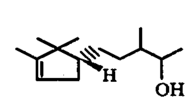 |
| 3-Methyl-5-(2,2,3-trimethylcyclopent-3-en-1-(S)-yl)pentan-2-ol | 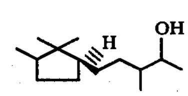 |
| 3-Methyl-5-(2,2,3-trimethylcyclopent-3-en-1-yl)pent-3-en-2-ol | 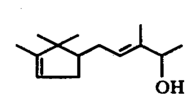 |

These materials are produced according to the reaction schemes:

TABLE II

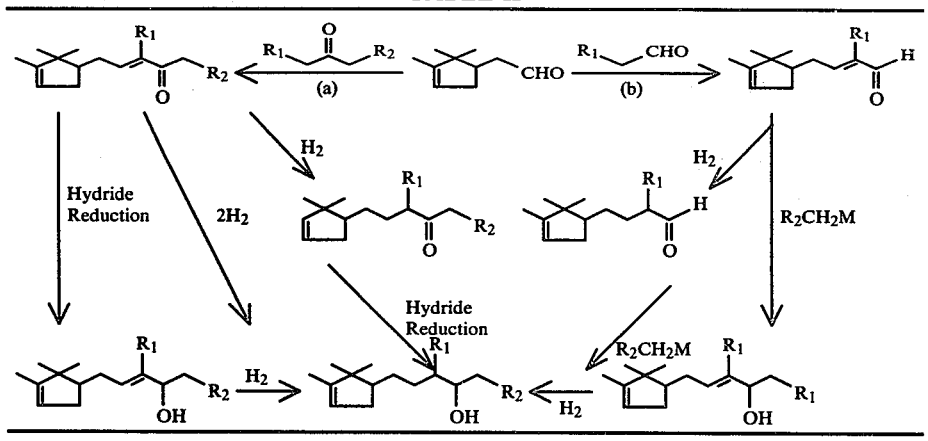

(a) $R_1$ = H, $CH_3, C_2H_5$
$R_2$ = H, $CH_3$

East Germany Patent No. 68,936 discloses for use in the sandalwood area a compound having the structure:

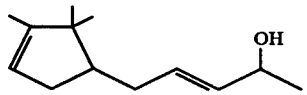

Furthermore, Chemical Abstracts Volume 72, 125008b sets forth a genus for the East German Pat. No. 68,936 encompassing the following group of compounds:

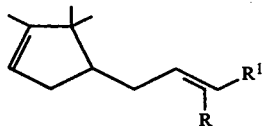

wherein R=$CH_2OH$, $CHCH_3OH$ and $R^1$=H,$CH_3$ or $C_2H_5$.

The processes of our invention using the zinc acetate catalyst provide a highly efficient advantages, unobvious route for a number of the aforementioned compounds and in addition provide certain novel compounds heretofore unavailable having the generic structure:

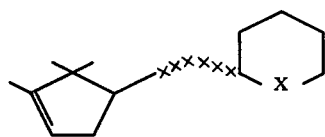

wherein one of the lines + + + + is a carbon-carbon single bond and the other of the lines + + + + is a carbon-carbon double bond and wherein X is one of the moieties

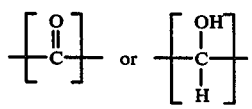

and these compounds have unobvious and unexpected properties insofar as their perfumery properties are concerned.

The use in zinc acetate in carrying out such reactions has heretofore been unknown and is not obvious from the teachings of the prior art. Thus, Houben-Weyl, "Methoden der organischen Chemie", volume 7/1, pages 77 et seq. and "Organic Reactions", volume 16, pages 27 to 47, 69 to 78 and 177 et seq. disclose the fact that aldehydes and ketones can be converted to $\alpha,\beta$-unsaturated ketones. Temperatures of from 5° C. up to 100° C. are preferred for this aldol condensation ("Organic Reactions," loc.cit., page 77). The numerous catalysts used in these methods, for example alkali and alkaline earth metal hydroxides, organic bases, alkali metal salts and alcoholates promote auto-condensation of the aldehydes and ketones and therefore cause the formation of large amounts of by-products in most cases.

Furthermore, the U.S. Pat. No. 4,005,147 discloses the production of alpha,beta-unsaturated ketones by reacting in the liquid phase an aldehyde with a ketone in the presence of a catalyst consisting essentially of zinc oxide.

It is furthermore known from U.S. Pat. No. 2,549,508 that aldehydes and ketones can be converted into unsaturated ketones of high molecular weight in the gas phase at temperatures of from 500° to 1000° C. in the presence of a catalyst consisting essentially of zinc oxide and from 1 to 15% by weight of zirconium oxide. In this process however only low conversions and low yields are achieved. Moreover high expenditure for equipment is required for reactions in the presence of hydrogen at the said temperature for safety reasons. Moreover cracking processes take place at the surface of the catalyst in such reactions and these have a negative effect on the life of the catalyst.

The reaction of two identical or different aldehydes or ketones in the liquid phase at elevated temperature and in the presence of a catalyst (obtained by calcining a mixture of molybdenum oxide, magnesium oxide with or without zinc oxide or compounds of these metals) to from alpha, beta-unsaturated aldehydes or ketones is known from German Patent No. 1,203,243.

According to the method described in the said patent good conversions and very good yields of alpha, beta-unsaturated aldehydes are obtained in the condensation of aldehydes with one another, particularly in the condensation of n-butyraldehyde or 2-ethylhexenal.

The process of German Patent No. 1,203,243 is not so suitable for the reaction of aldehydes with ketones to form alpha,beta-unsaturated ketones, considerably lower conversions and selectivities being achieved. This is particularly noticeable when not only isobutyraldehyde (i.e., and aldehyde which does not undergo autocondensation) is reacted with a ketone by the method of the said German patent, but also aldehydes are used which readily undergo autocondensation, as for example 3,3-dimethylacrolein and citral.

Nothing in the prior art, however, implies the process of our invention using zinc acetate catalyst whereby 2,2,3-trimethyl-3-cyclopenten-1-ylalkenyl and alkylidene secondary alkanols, alkanones, cycloalkanols and cycloalkanones may be produced in a convenient, sufficient and economical manner.

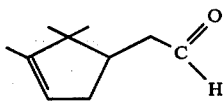

Figure 2:
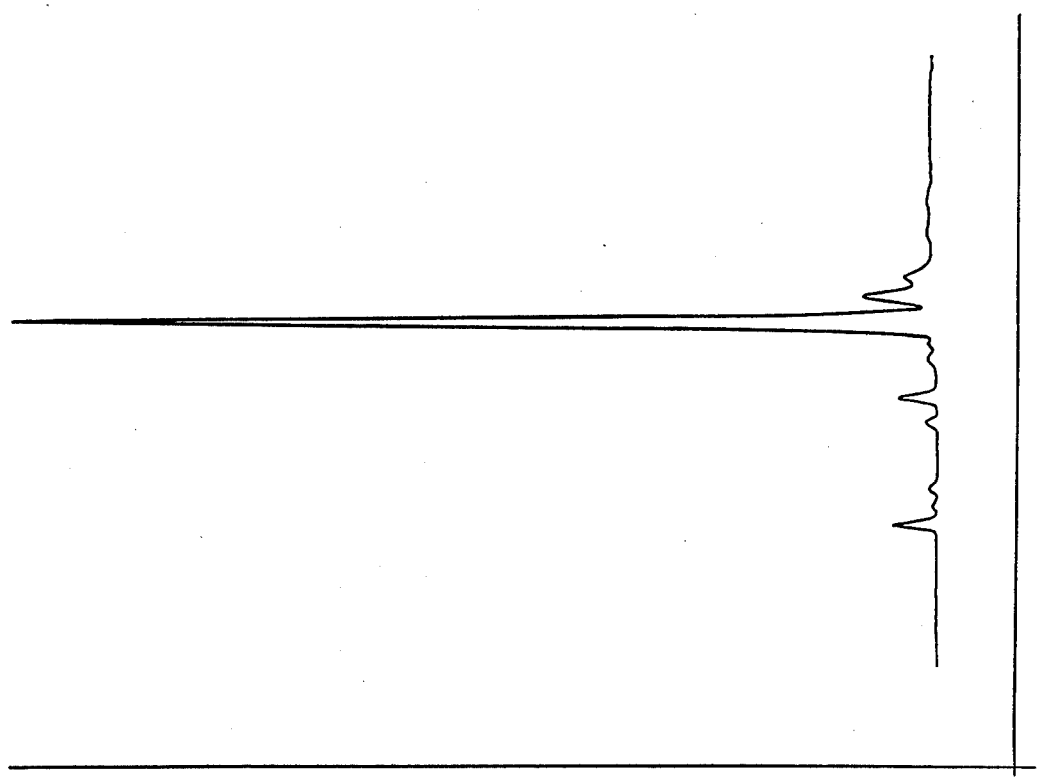

FIG. 2 is a GLC profile for a refined form of the compound having the structure:

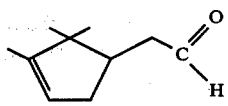

resulting from fractionation of the reaction mass.

Figure 3:
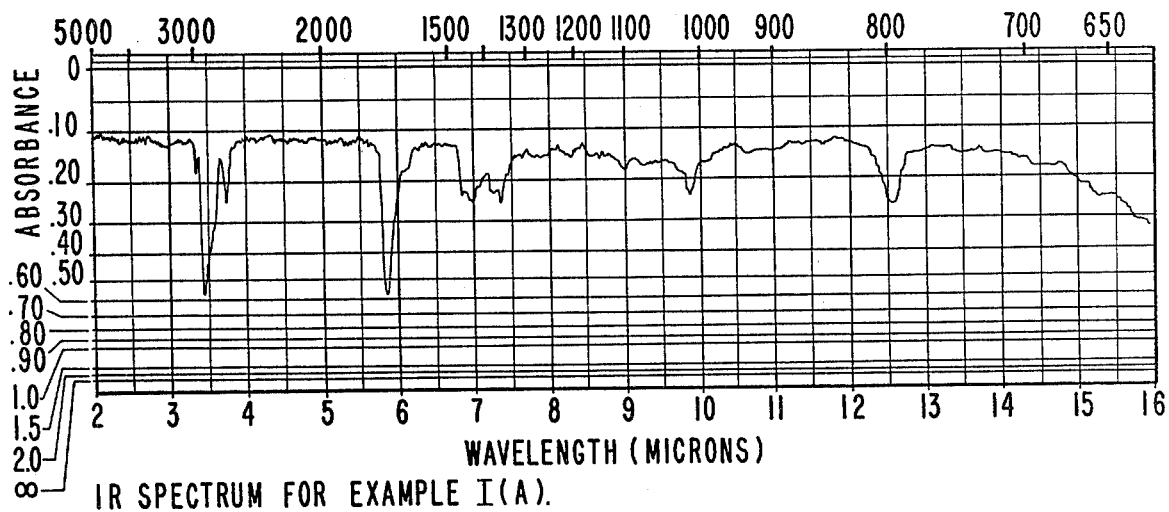

FIG. 3 is the infrared spectrum for the compound having the structure:

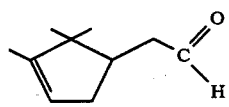

produced according to the process of Example IA.

Figure 4:
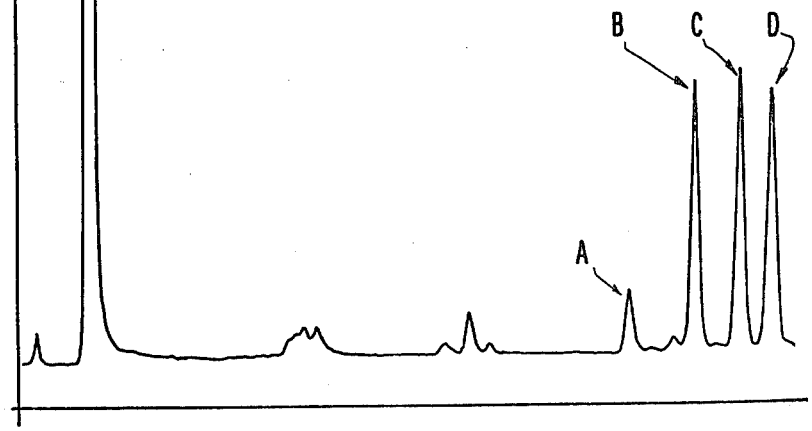

FIG. 4 is the GLC profile for the product produced according to Example IB which is a mixture defined by the structure:

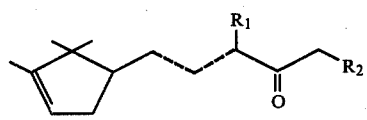

wherein either $R_1$ or $R_2$ is methyl and the other is hydrogen and one of the dashed lines is a carbon-carbon single bond and the other of the dashed lines is a caron-carbon double bond.

Figure 5:
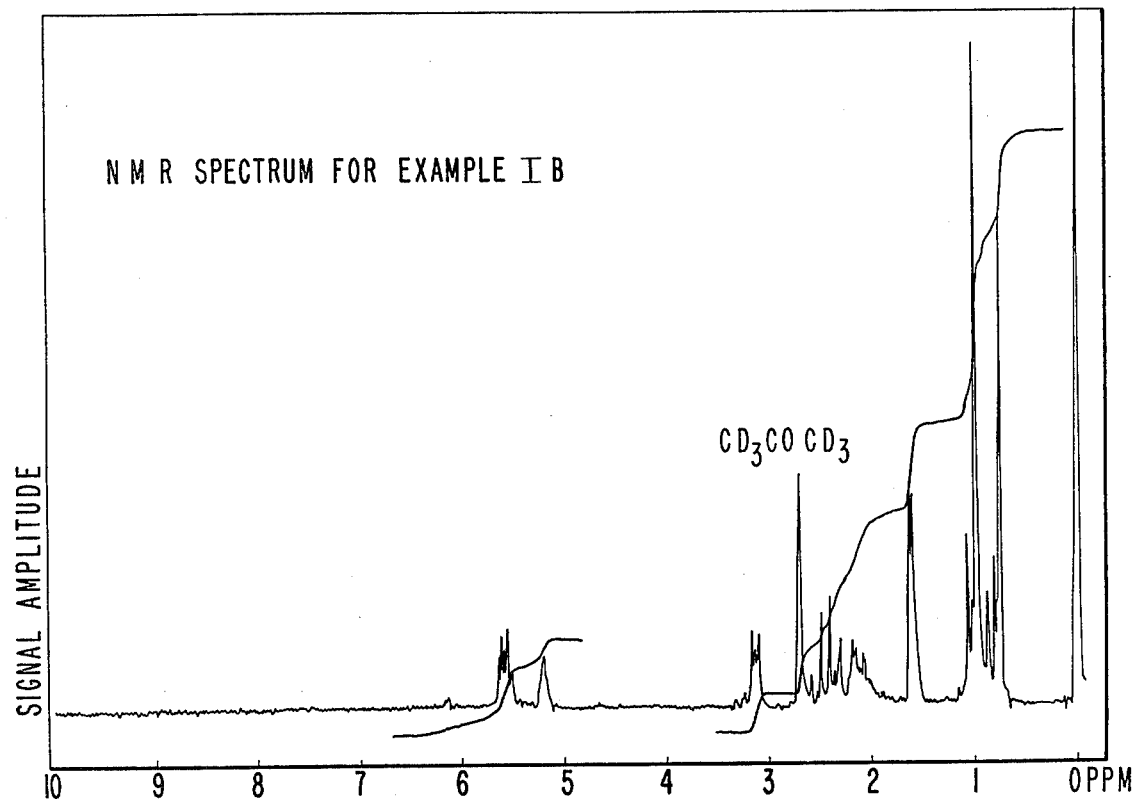

FIG. 5 is the NMR spectrum for the product produced according to Example IB containing compounds having the structures:

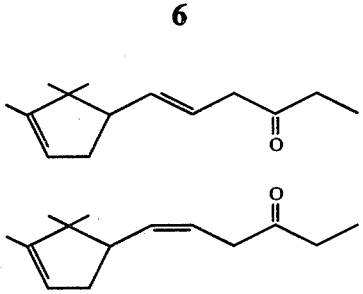

Figure 6:
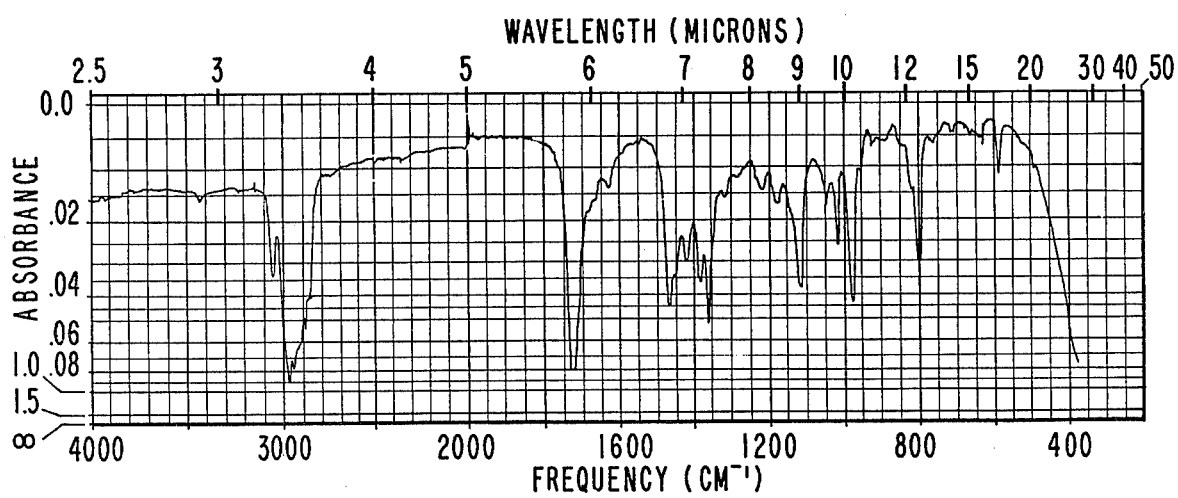

FIG. 6 is the infrared spectrum for the product produced according to Example IB containing compounds having the structures:

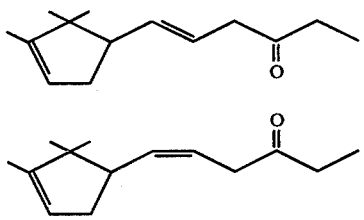

Figure 7:
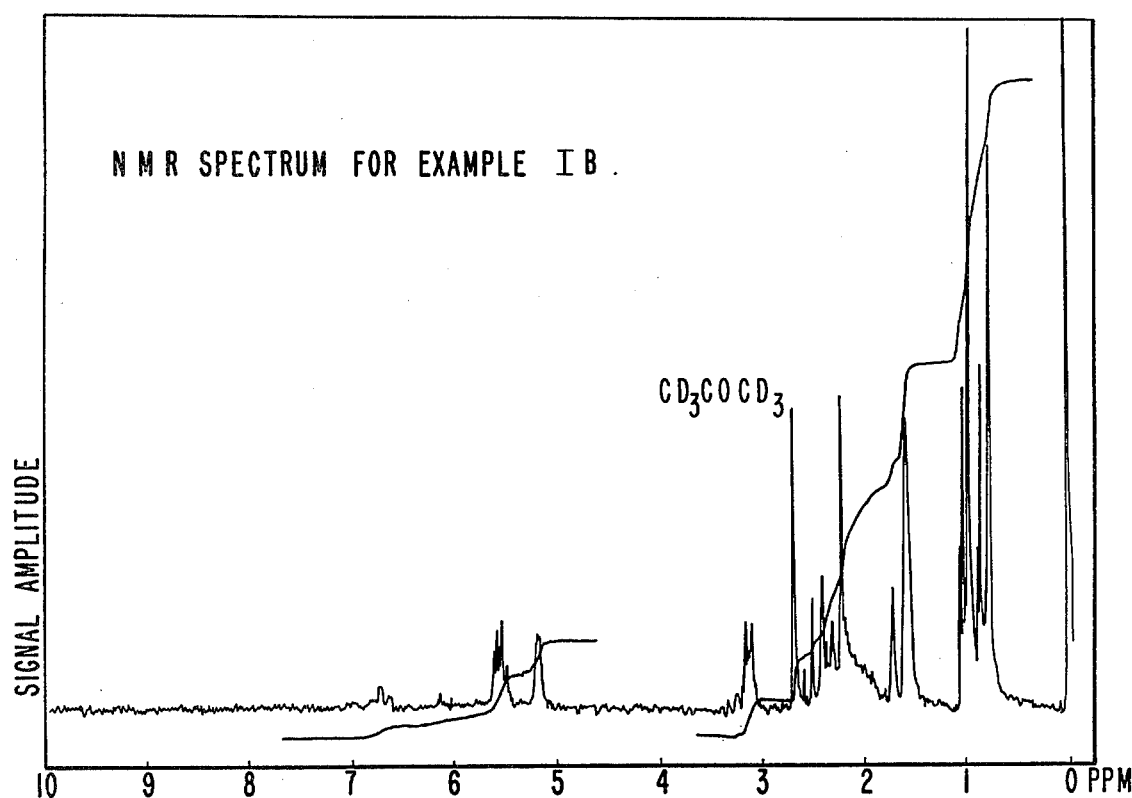

FIG. 7 is the NMR spectrum for the product produced according to Example IB having compounds having the structures:

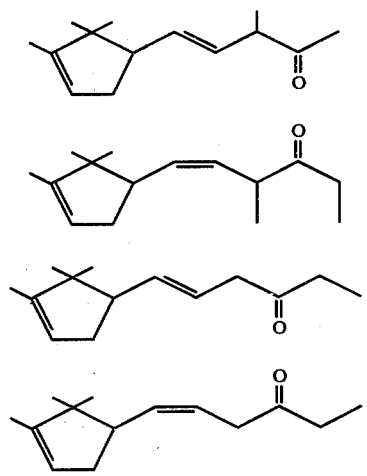

Figure 8:
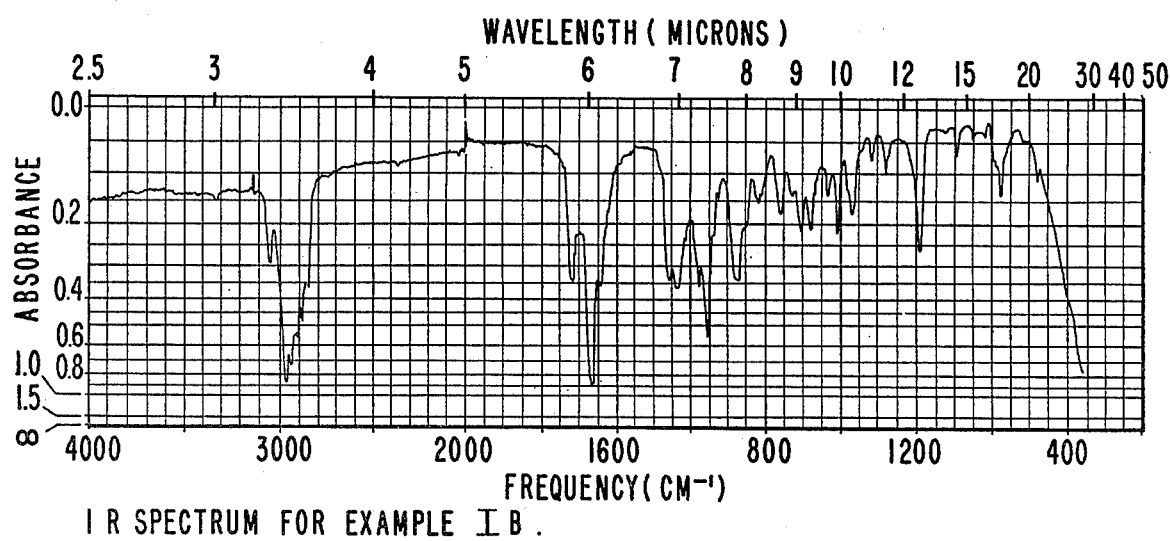

FIG. 8 is the infrared spectrum of the reaction product of Example IB containing compounds having the structures:

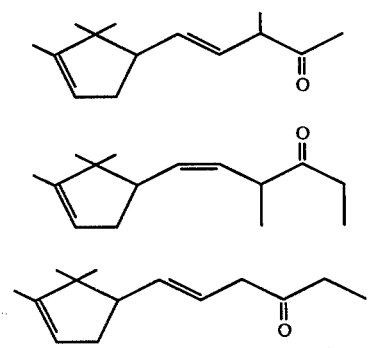

-continued

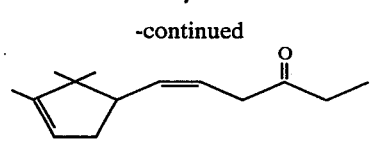

Figure 9:
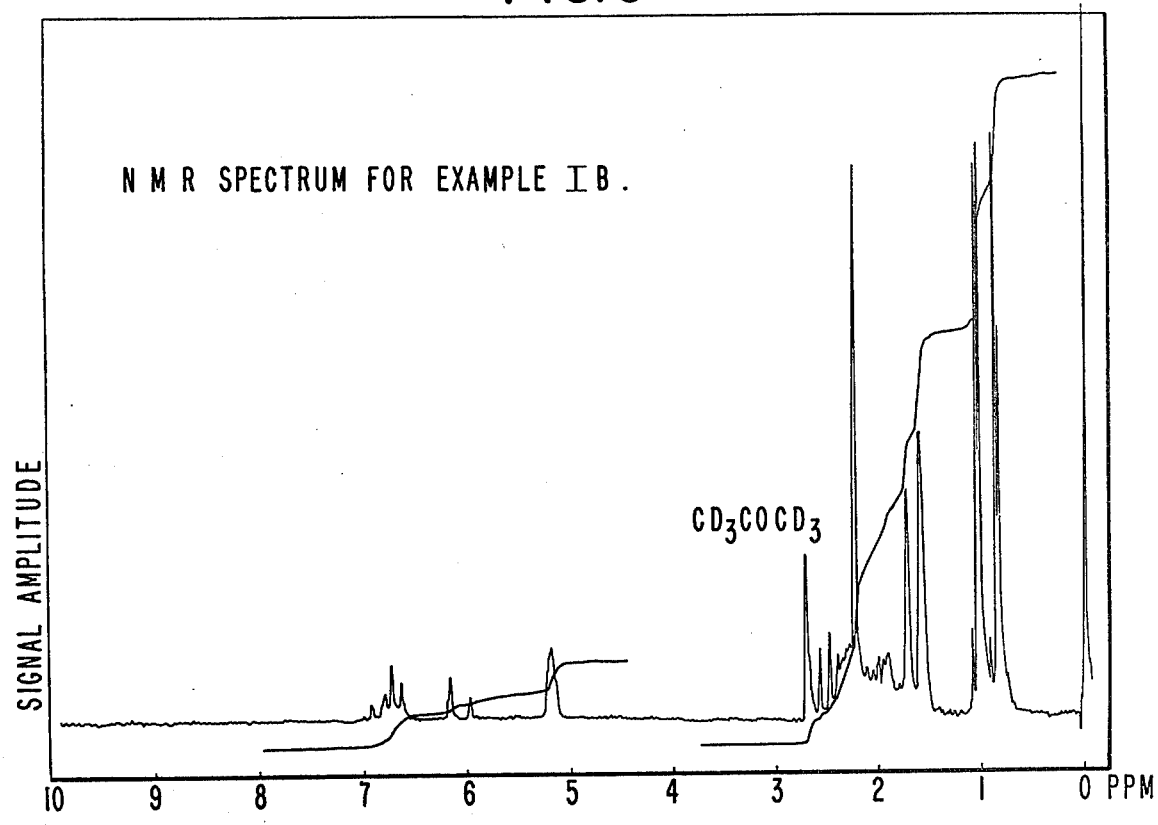

FIG. 9 is the NMR spectrum for the reaction product produced according to Example IB having compounds having the structures:

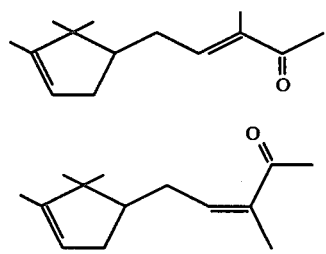

Figure 10:
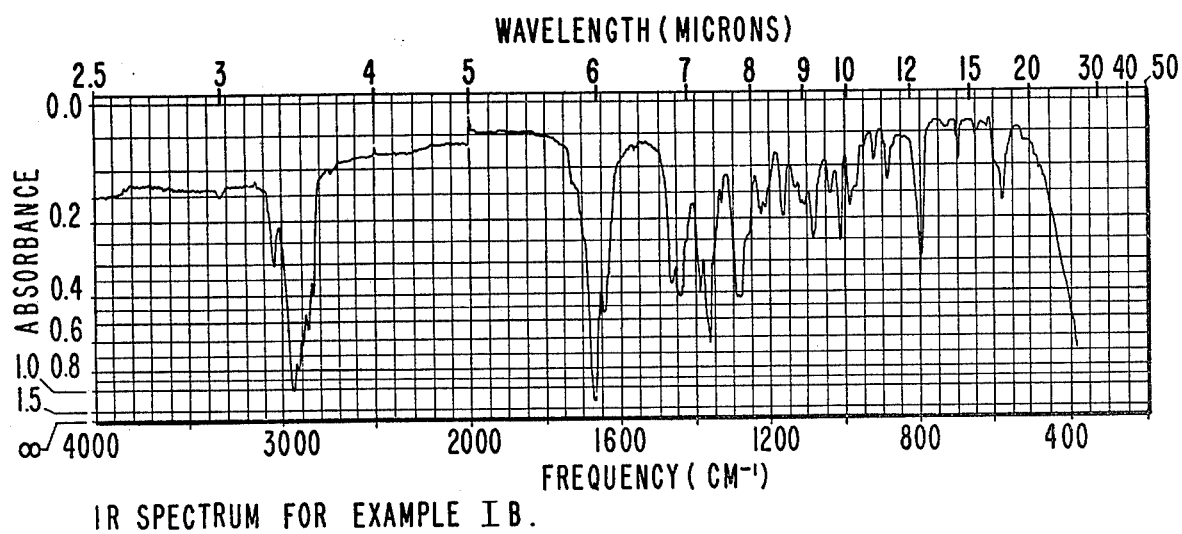

FIG. 10 is the infrared spectrum for the reaction product produced according to Example IB having compounds having the structures:

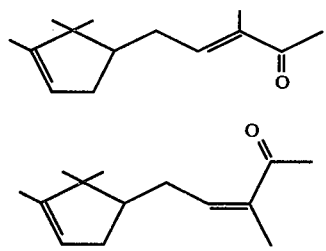

Figure 11:
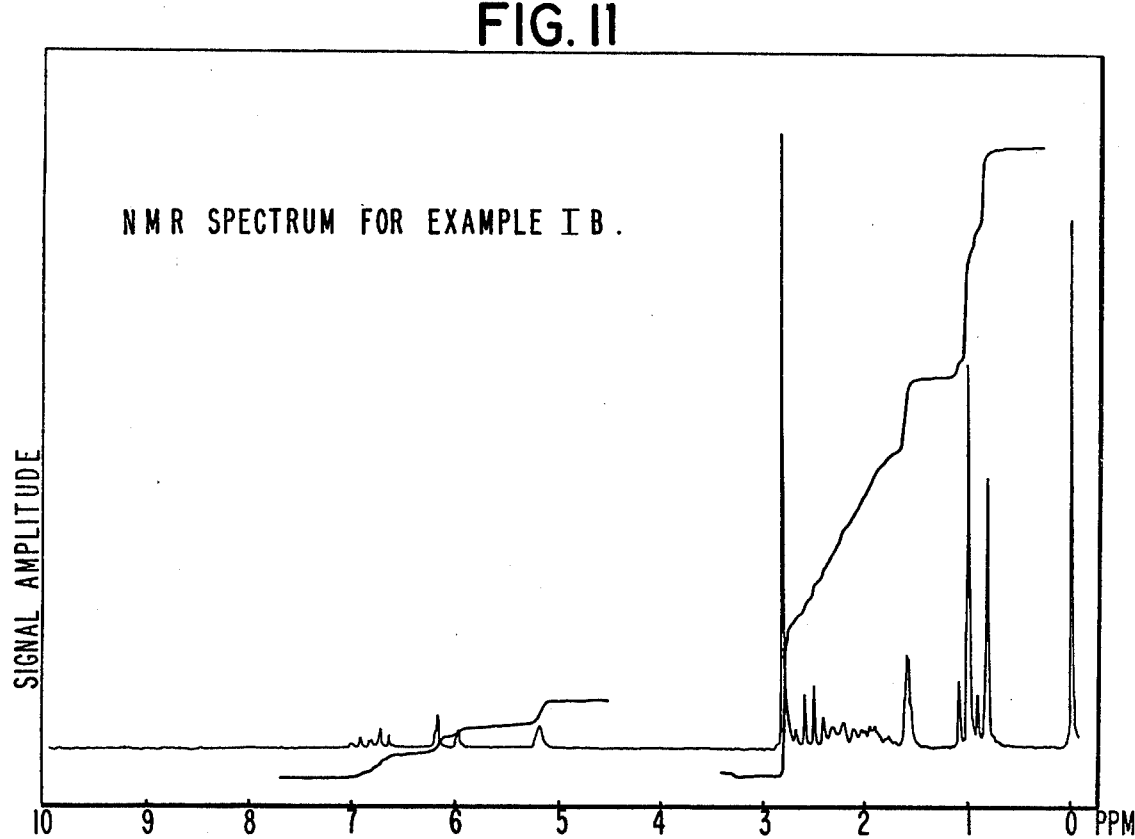

FIG. 11 is the NMR spectrum for the reaction product of Example IB having structures:

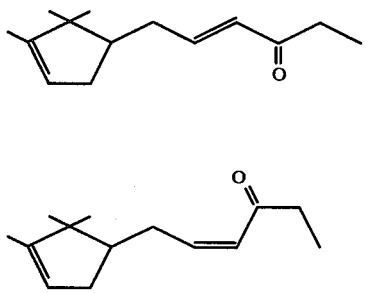

Figure 12:
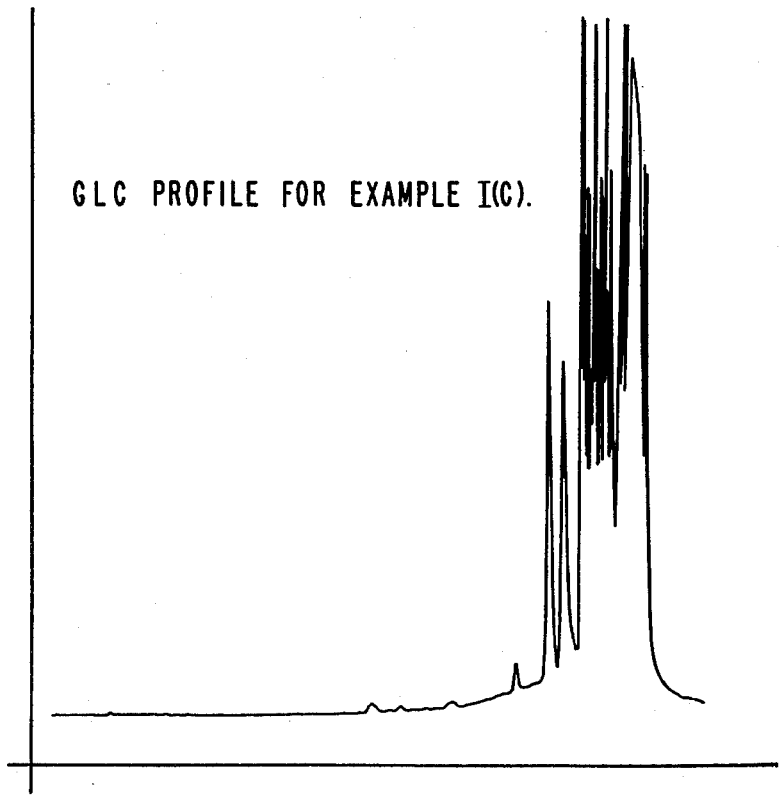

FIG. 12 is the GLC profile for the product produced according to the process of Example IC having a mixture of compounds contained therein having the generic structure:

($R_1$ or $R_2$ is methyl and the other of $R_1$ or $R_2$ is hydrogen and one of the dashed lines is a carbon-carbon double bond and the other of the dashed lines is a carbon-carbon single bond.

Figure 13:
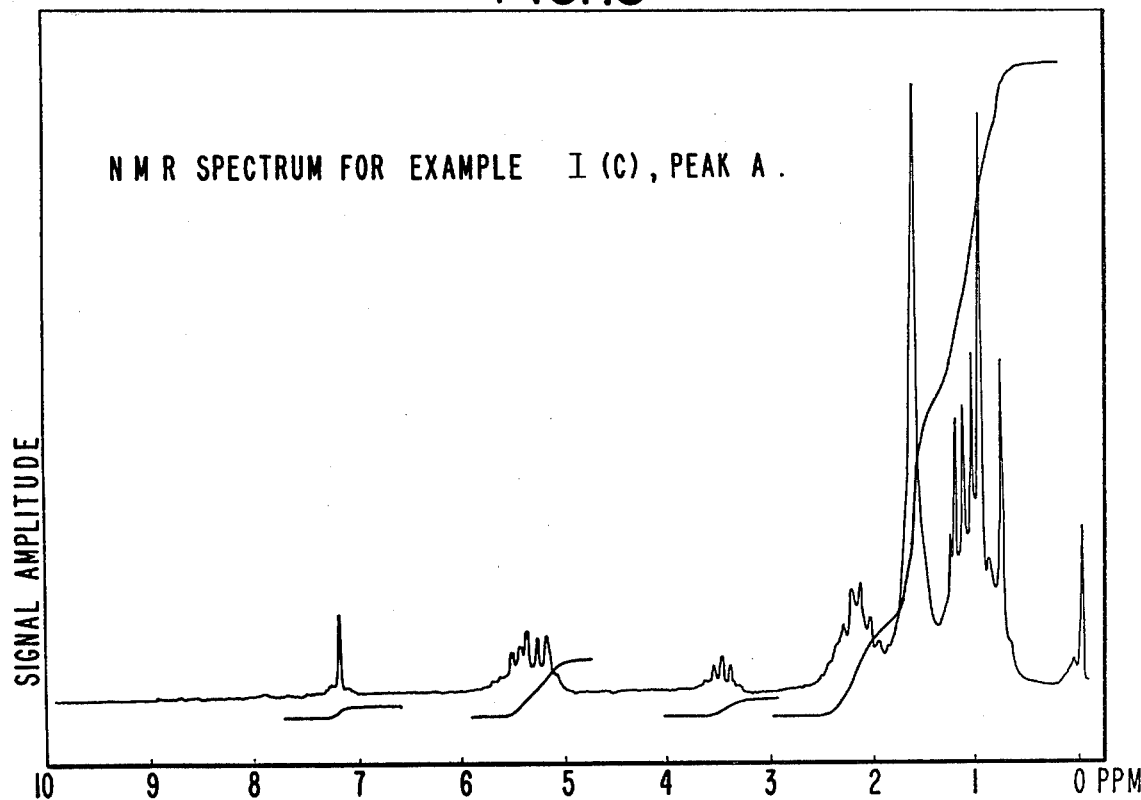

FIG. 13 is the NMR spectrum for the reaction product of Example IC, peak "A" of the GLC profile of FIG. 12.

Figure 14:
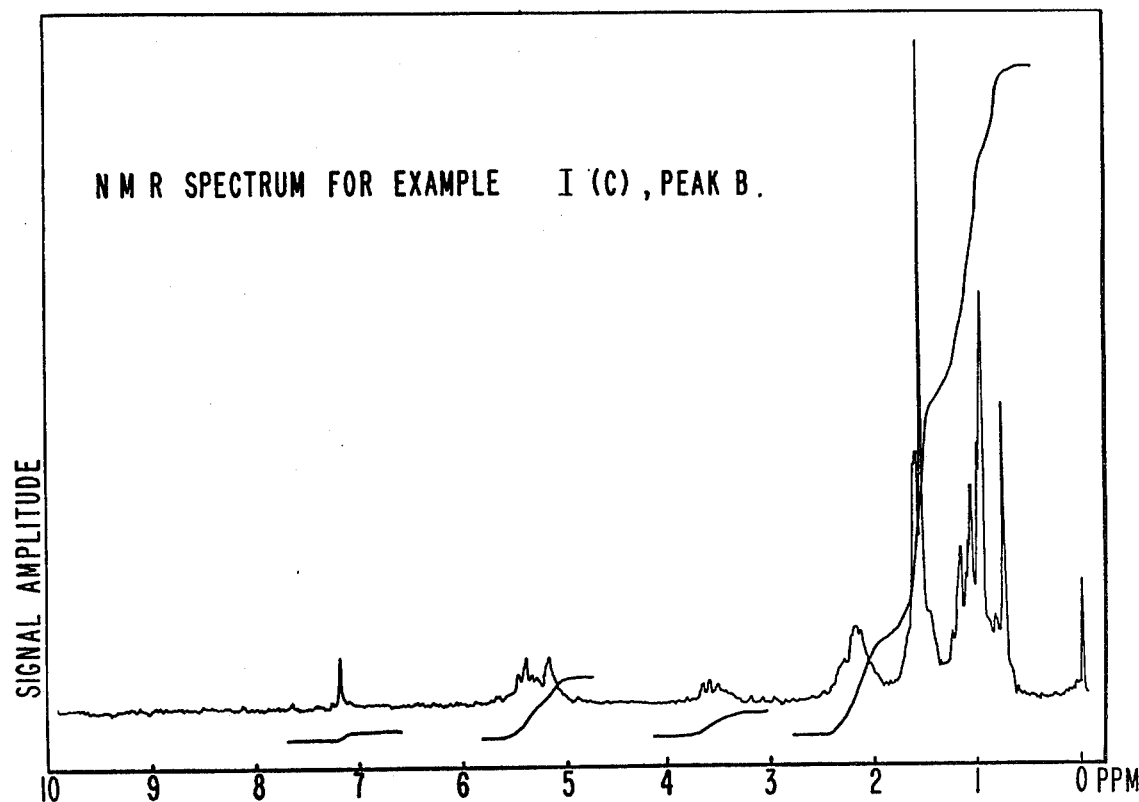

FIG. 14 is the NMR spectrum for the reaction product of Example IC, peak "B" of the GLC profile of FIG. 12.

Figure 15:
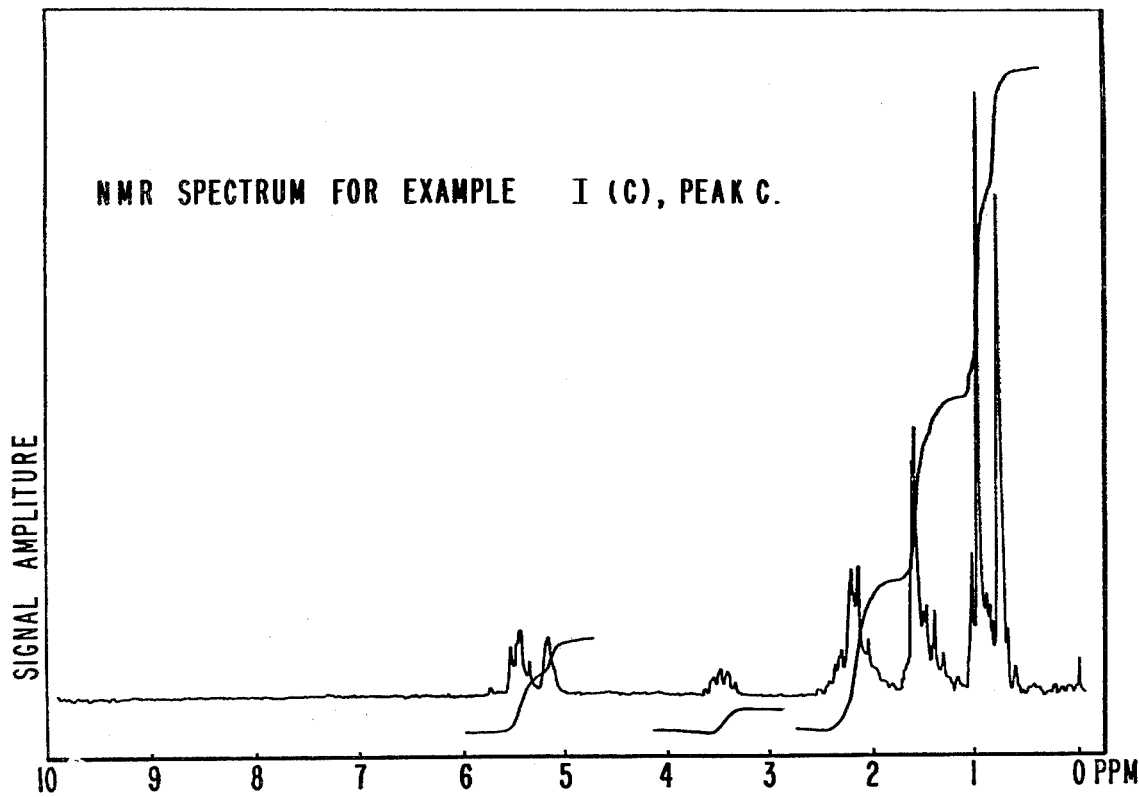

FIG. 15 is the NMR spectrum for the reaction product of Example IC, peak "C" of the GLC profile of FIG. 12.

Figure 16:
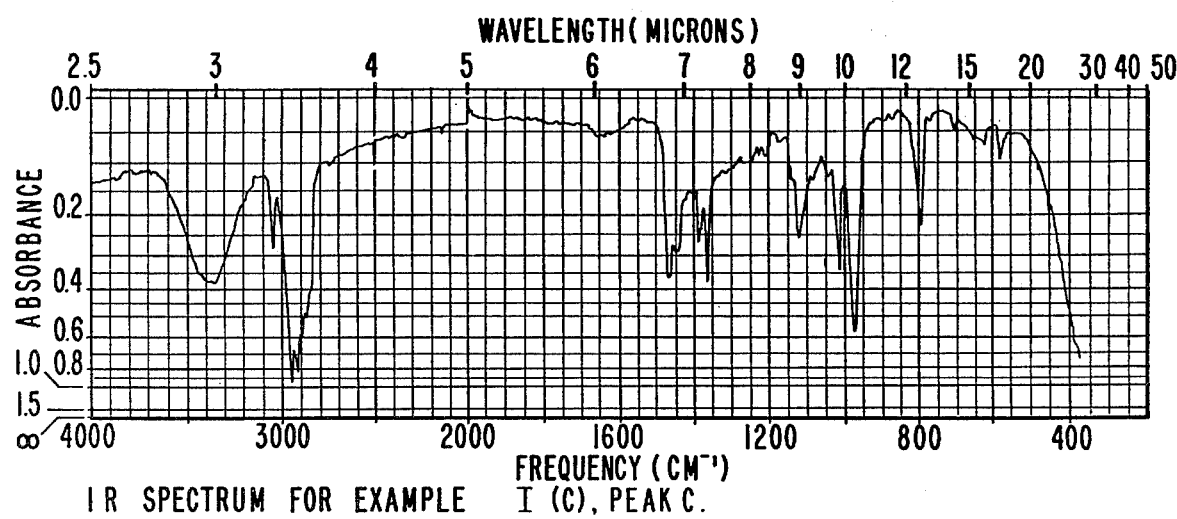

FIG. 16 is the infrared spectrum for the reaction product of Example IC, peak "C" of the GLC profile of FIG. 12.

Figure 17:
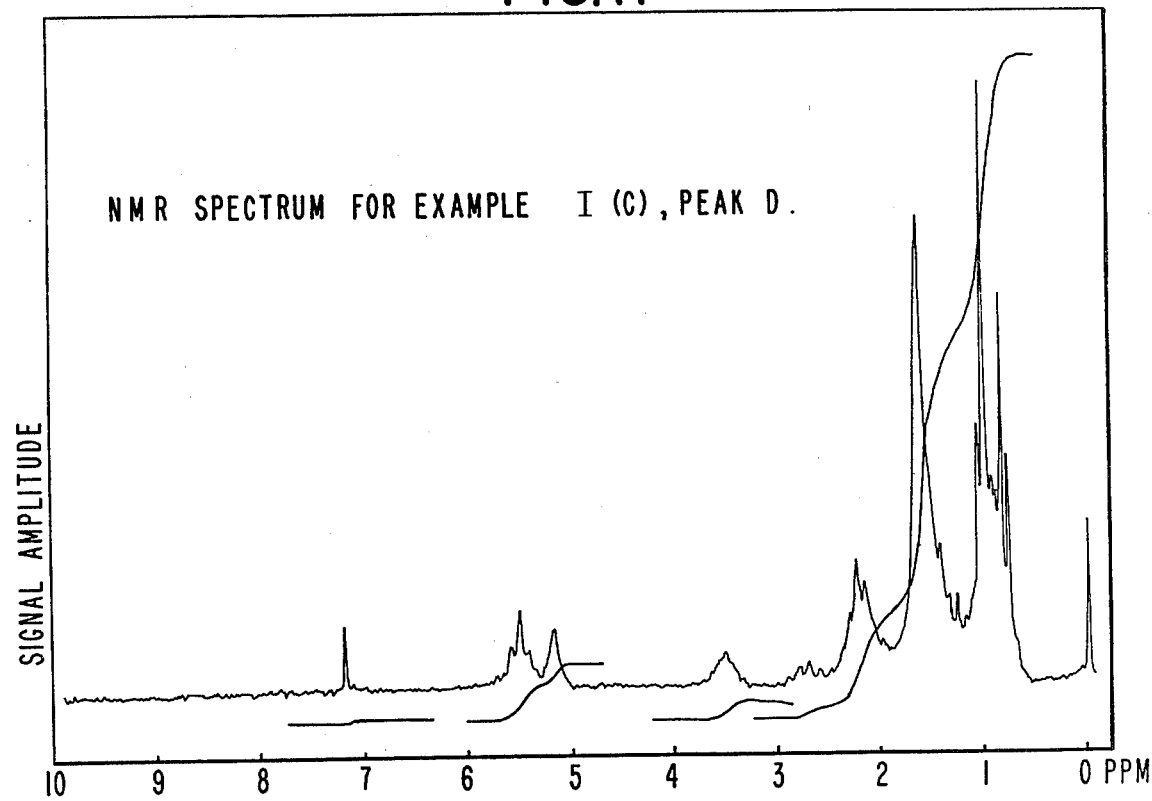

FIG. 17 is the NMR spectrum for the reaction product of Example IC, peak "D" of the GLC profile of FIG. 12.

Figure 18:
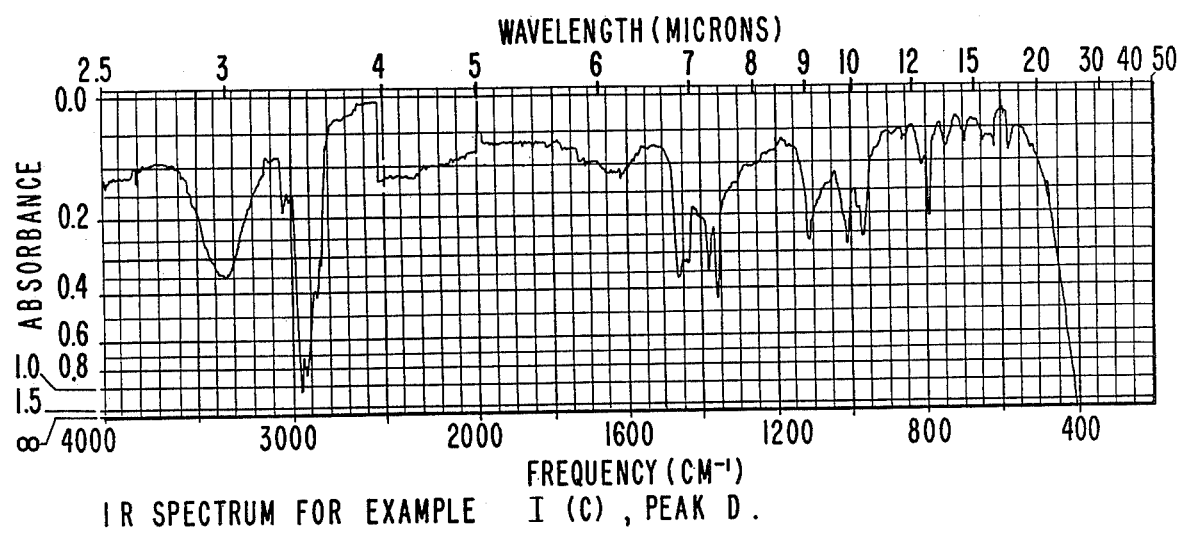

FIG. 18 is the infrared spectrum for the reaction product of Example IC, peak "D" of the GLC profile of FIG. 12.

Figure 19:
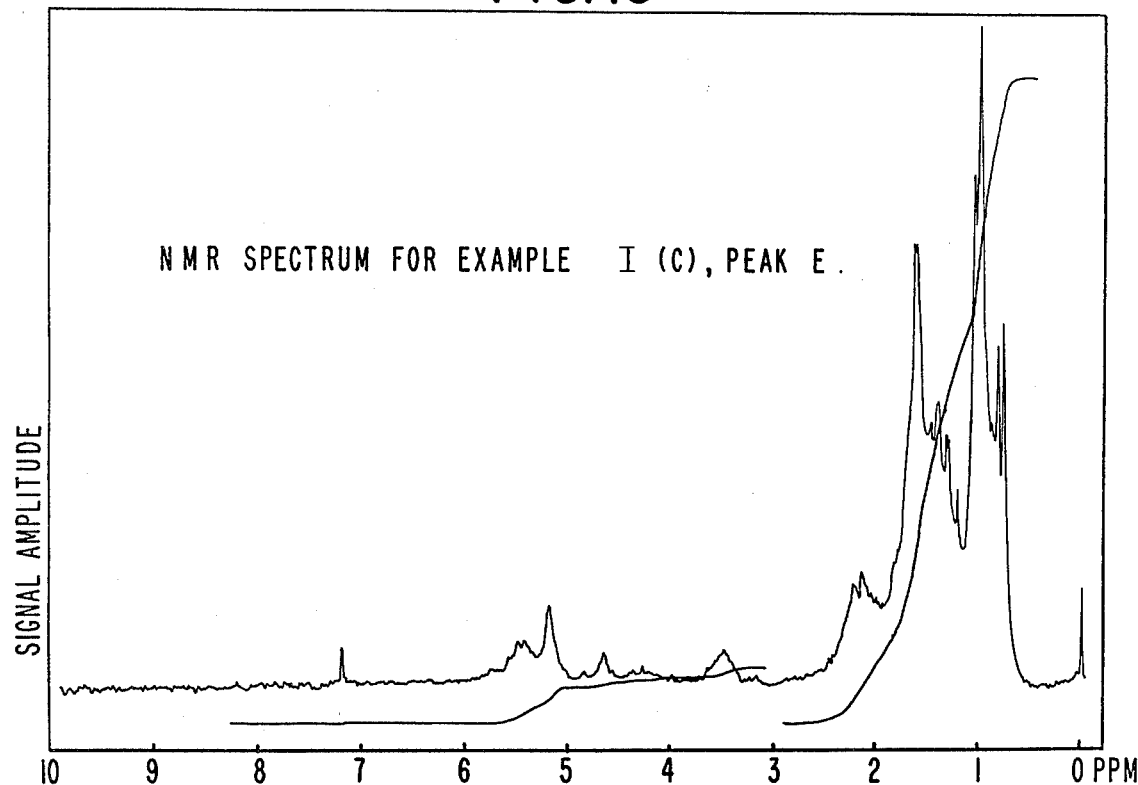

FIG. 19 is the NMR spectrum for the reaction product of Example IC, peak "E" of the GLC profile of FIG. 12.

Figure 20:
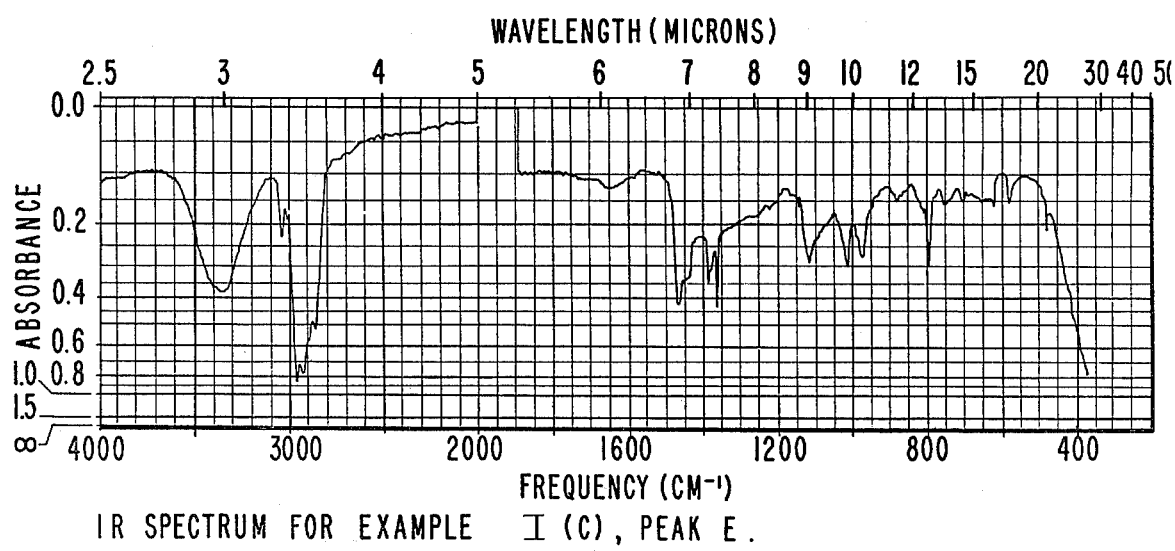

FIG. 20 is the infrared spectrum for the reaction product of Example IC, peak "E" of the GLC profile of FIG. 12.

Figure 21:
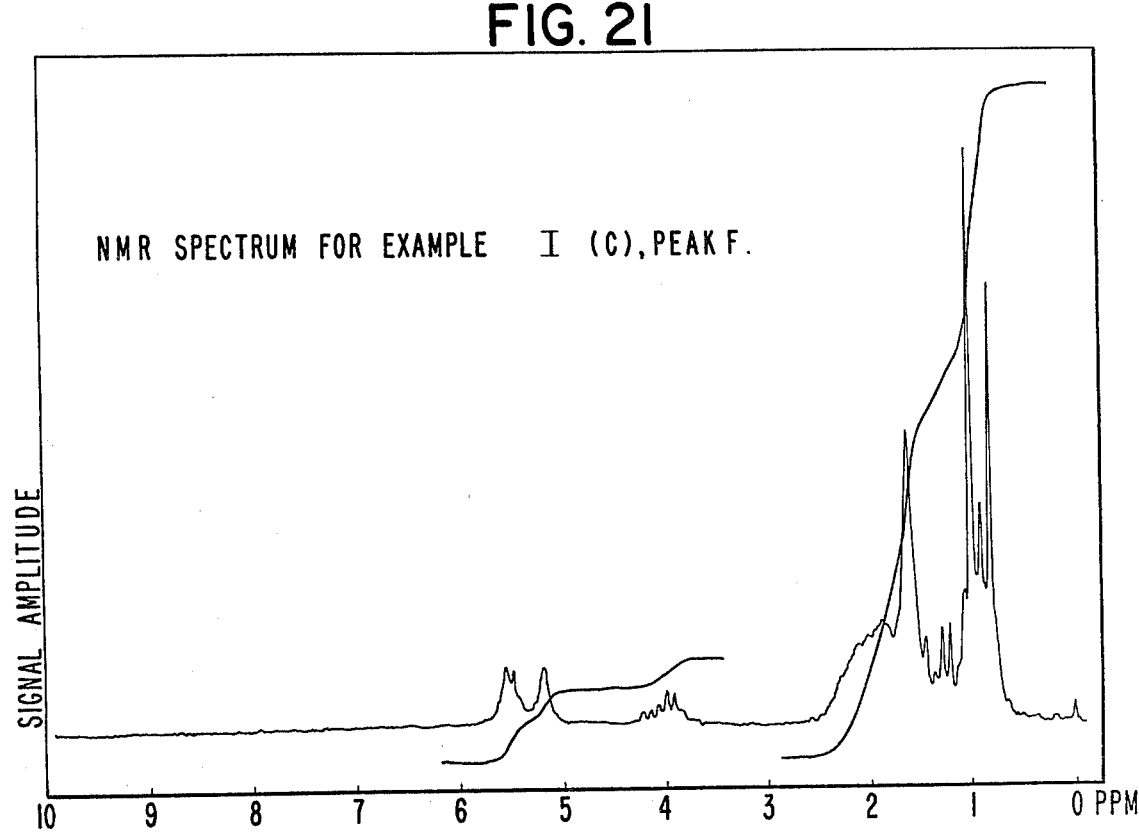

FIG. 21 is the NMR spectrum for the reaction product of Example IC, peak "F" of the GLC profile of FIG. 12.

Figure 22:
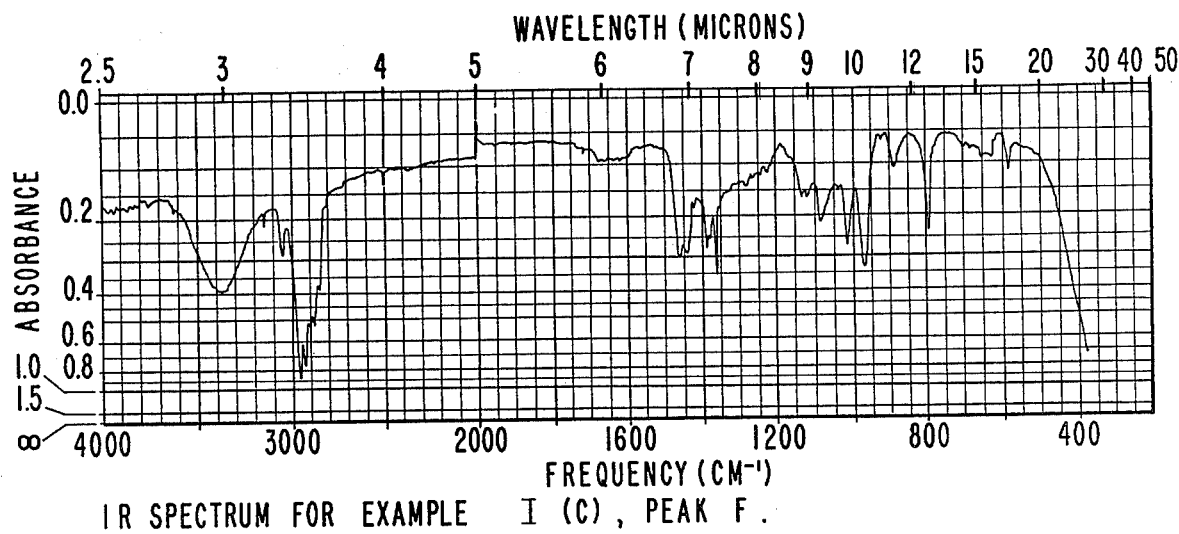

FIG. 22 is the infrared spectrum for the reaction product of Example IC, peak "F" of the GLC profile of FIG. 12.

Figure 23:
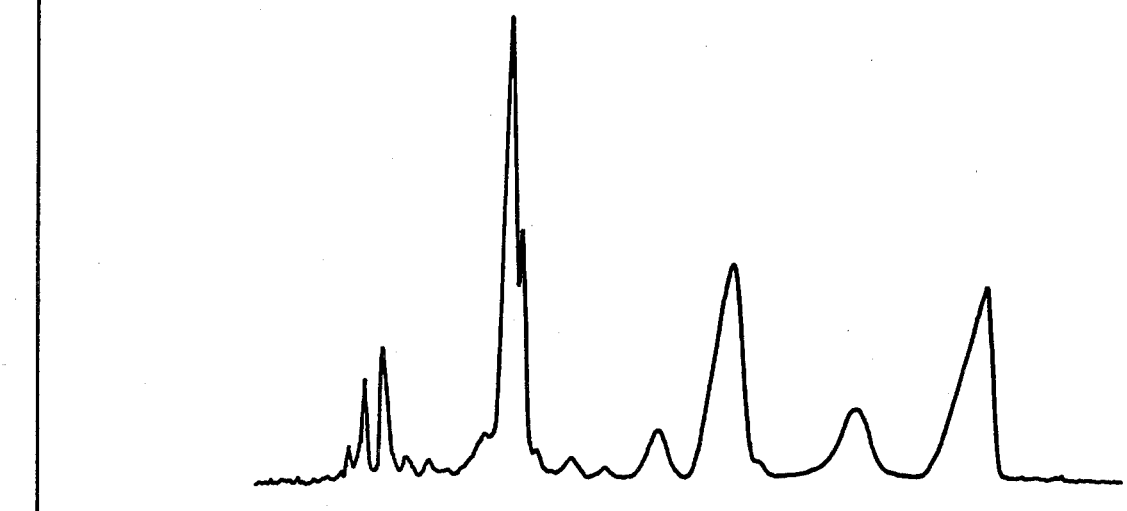

FIG. 23 is the GLC profile for the reaction product of Example IIA consisting of compounds having the structures:

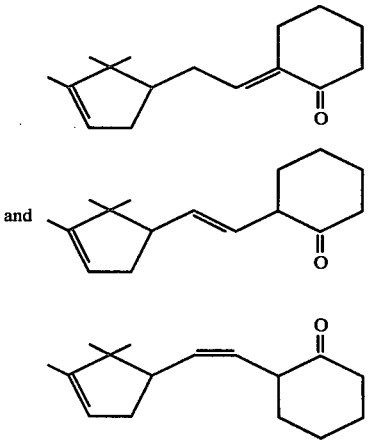

Figure 24:
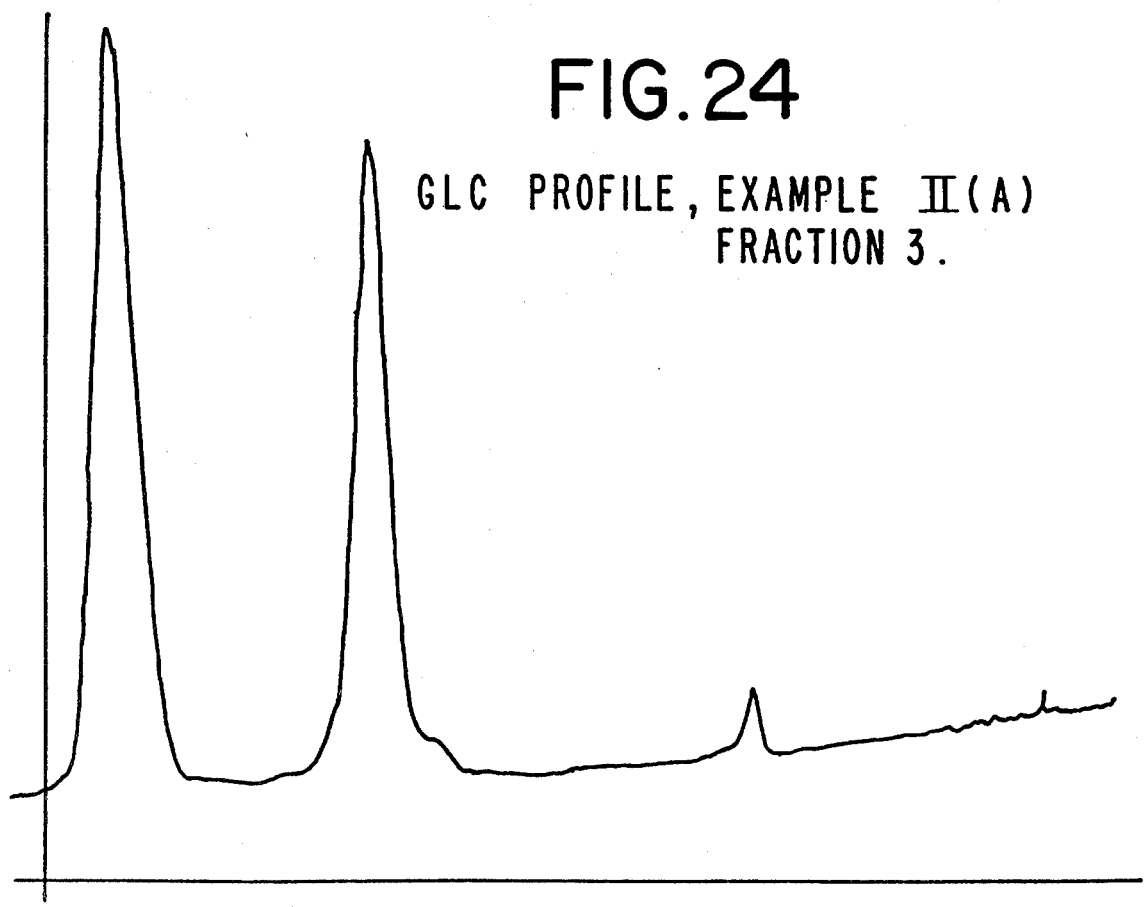

FIG. 24 is the GLC profile for fraction 3 resulting from the fractional distillation of the reaction product of Example IIA which contains compounds having the structures:

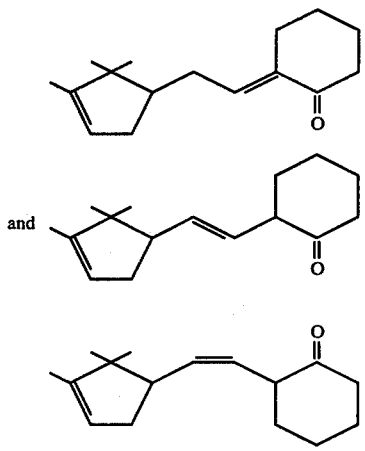

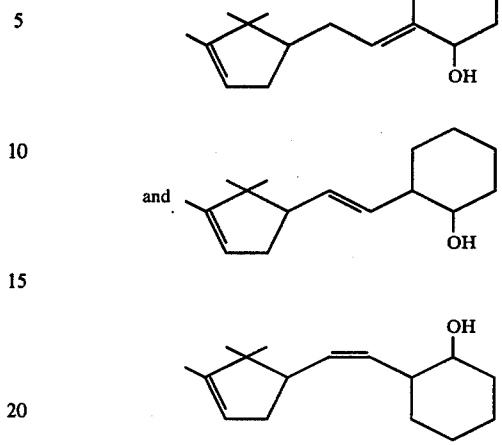

Figure 25:
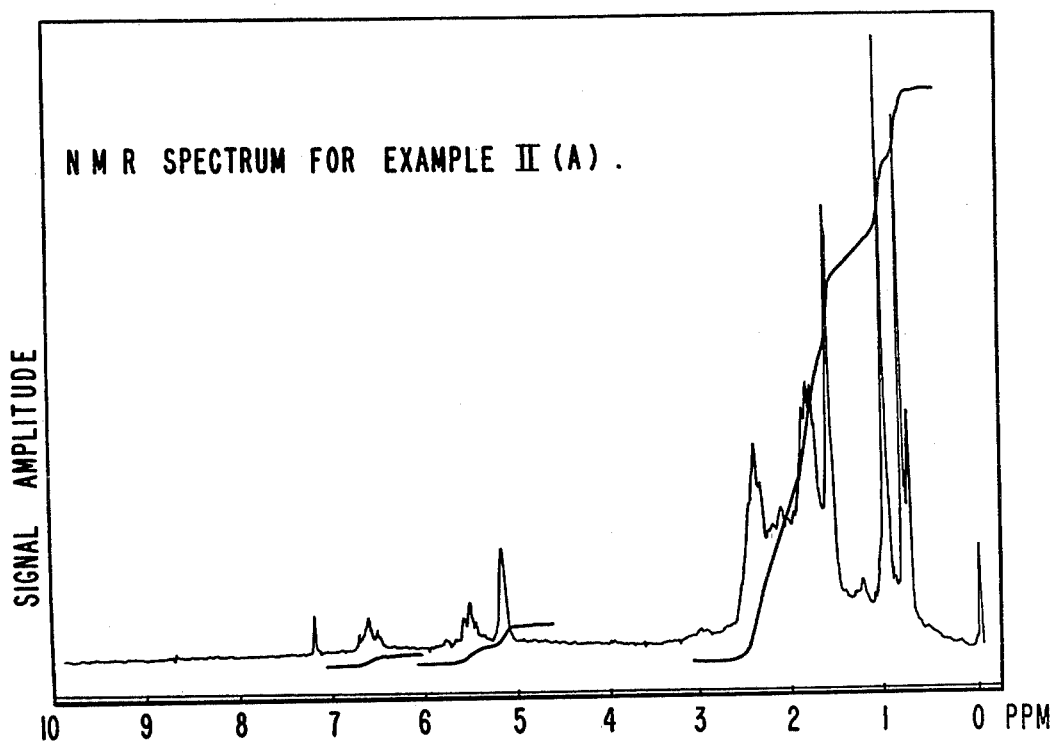
Figure 27:
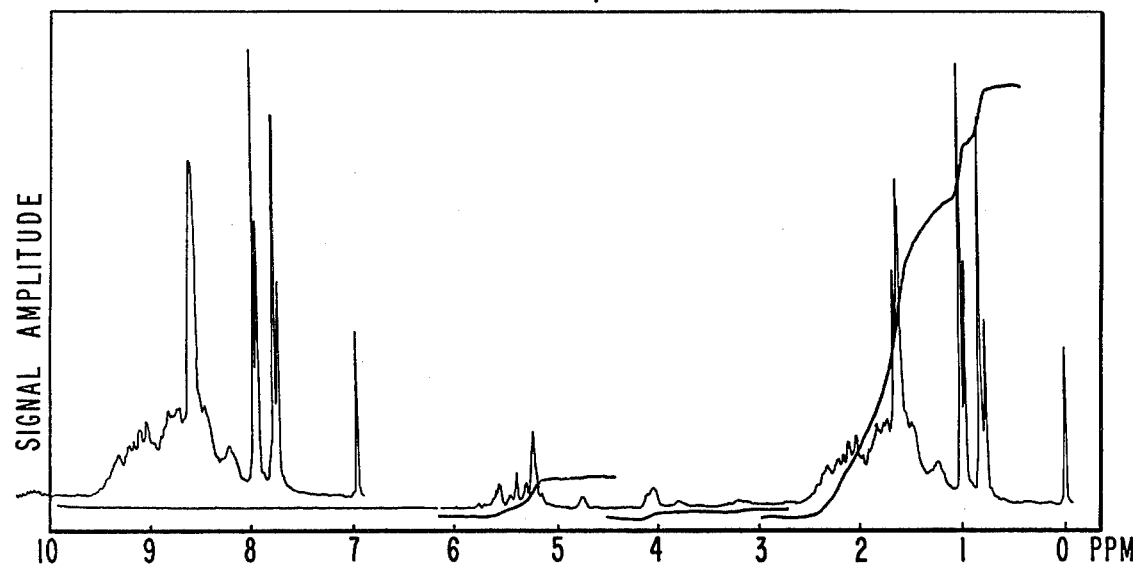

FIG. 27 is the NMR spectrum for fraction 2 resulting from a fractional distillation of the reaction product of Example IIB, having compounds having the structures:

FIG. 25 is the NMR spectrum for fraction 3 resulting from the fractional distillation of the reaction product of Example IIA having the compounds having the structures:

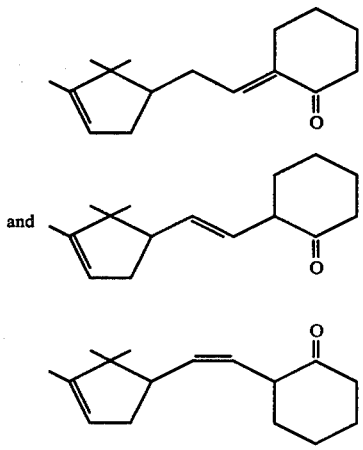

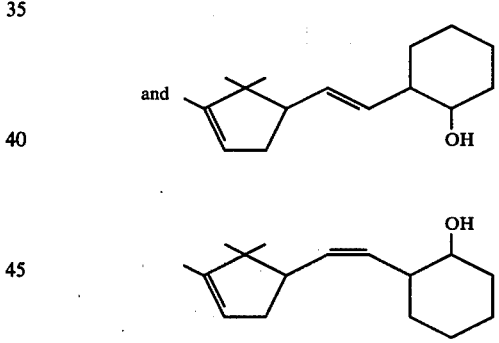

Figure 28:
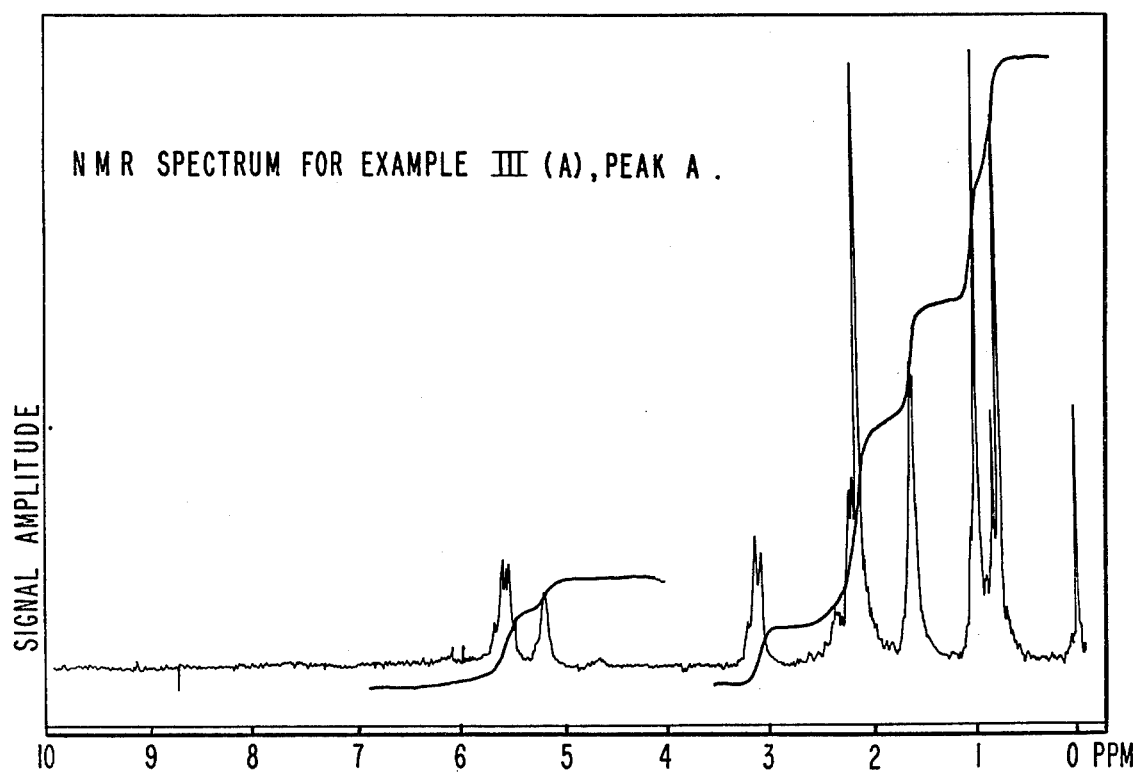

FIG. 28 is the NMR spectrum for peak "A" of the reaction product of Example IIIA containing compounds having the structures:

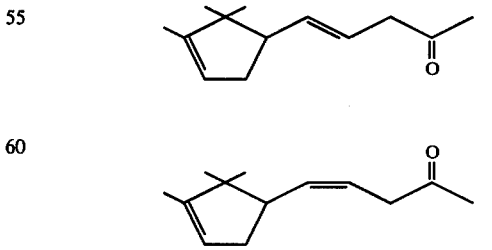

Figure 26:
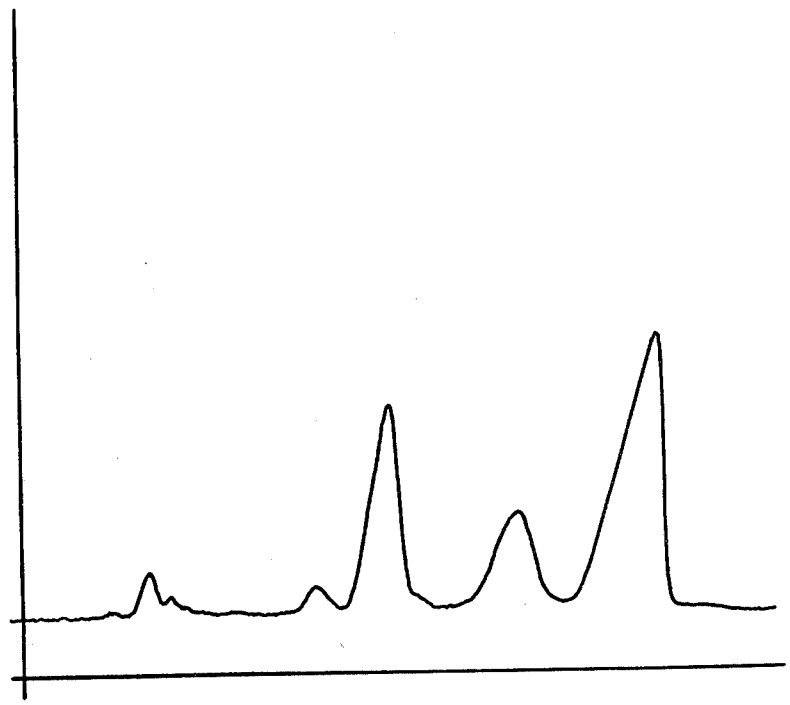

FIG. 26 is the GLC profile for the reaction product of Example IIB having the compounds having the structures:

FIG. 29 is the infrared spectrum for the reaction product of Example IIIA, peak "A" containing compounds having the structures:

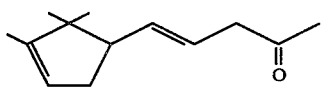

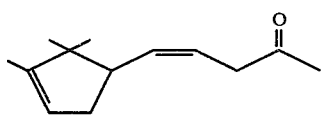

FIG. 30 is the NMR spectrum for peak "B" of the reaction product of Example IIIA containing compounds having the structures:

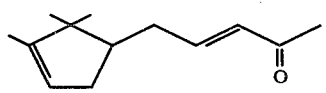

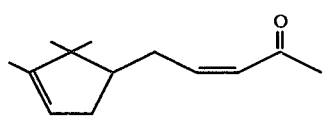

FIG. 31 is the infrared spectrum for peak "B" of the reaction product of Example IIIA containing compounds having the structures:

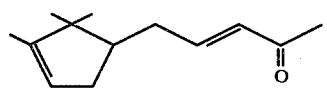

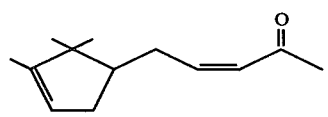

FIG. 32 is the NMR spectrum for peak "A" of the reaction product produced according to Example IIIB containing compounds having the structures:

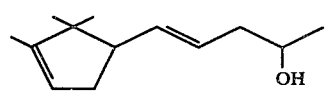

Figure 33:
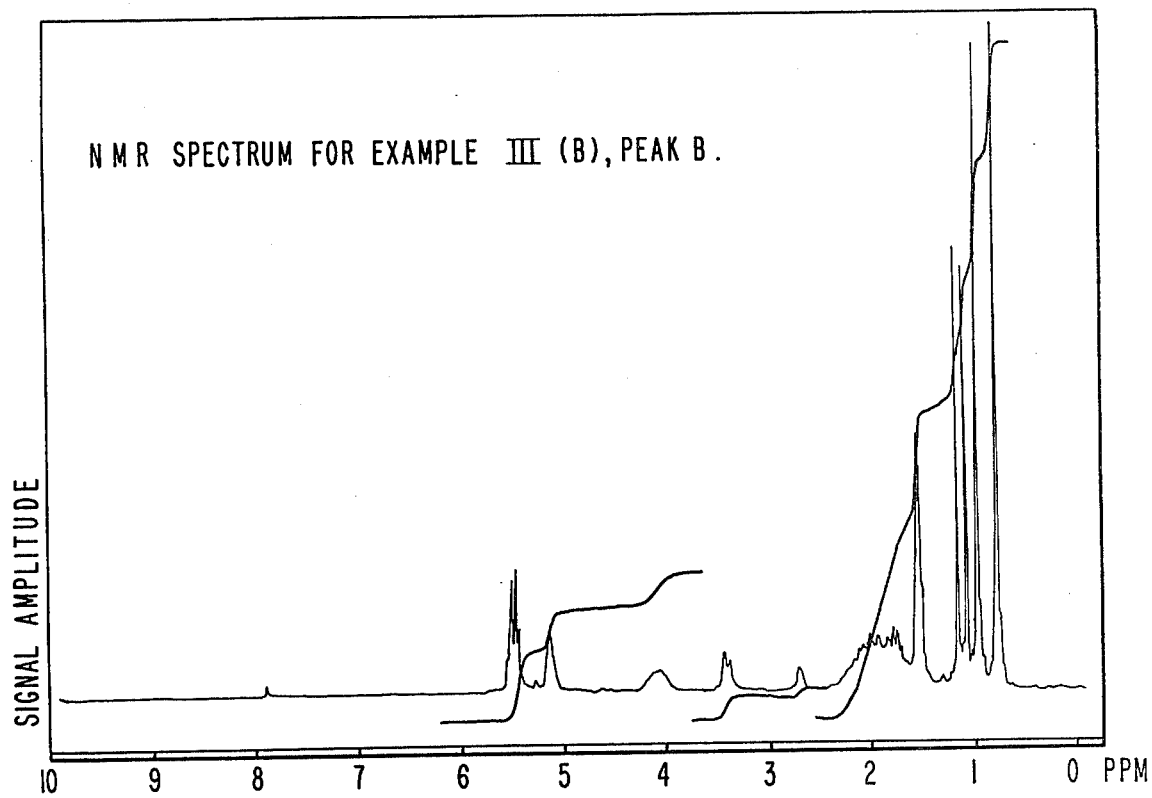

FIG. 33 is the NMR spectrum for peak "B" of the reaction product of Example IIIB containing compounds having the structures:

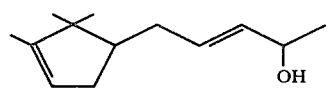

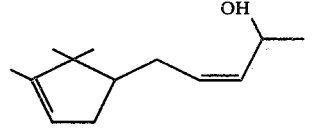

Figure 34:
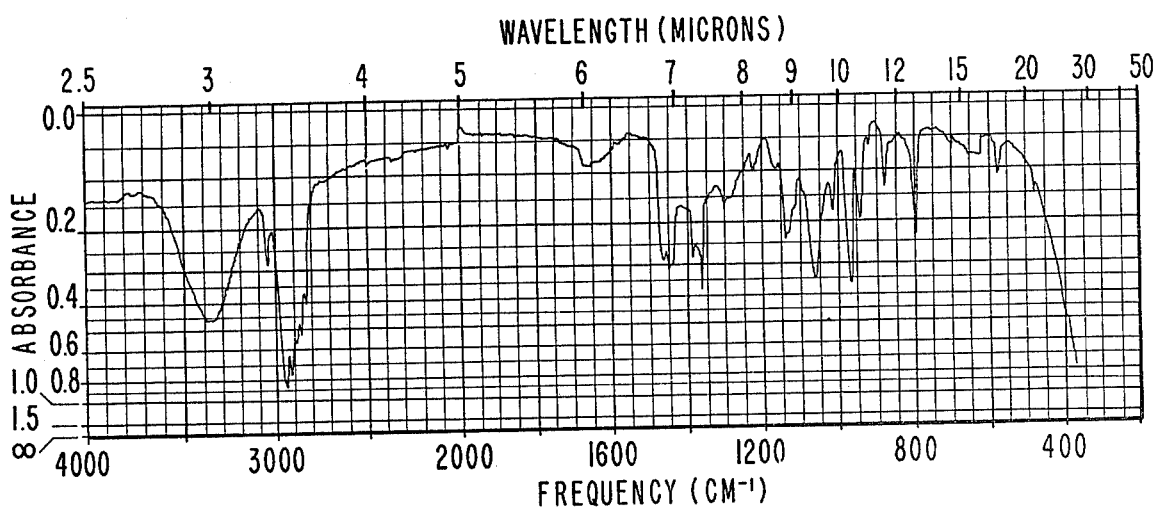

FIG. 34 is the infrared spectrum for peak "B" of the reaction product produced according to Example IIIB containing compounds having the structures:

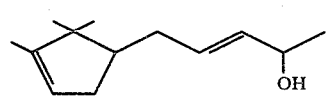

and

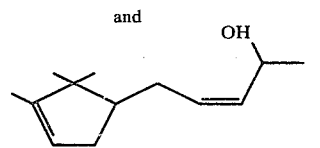

Figure 35:
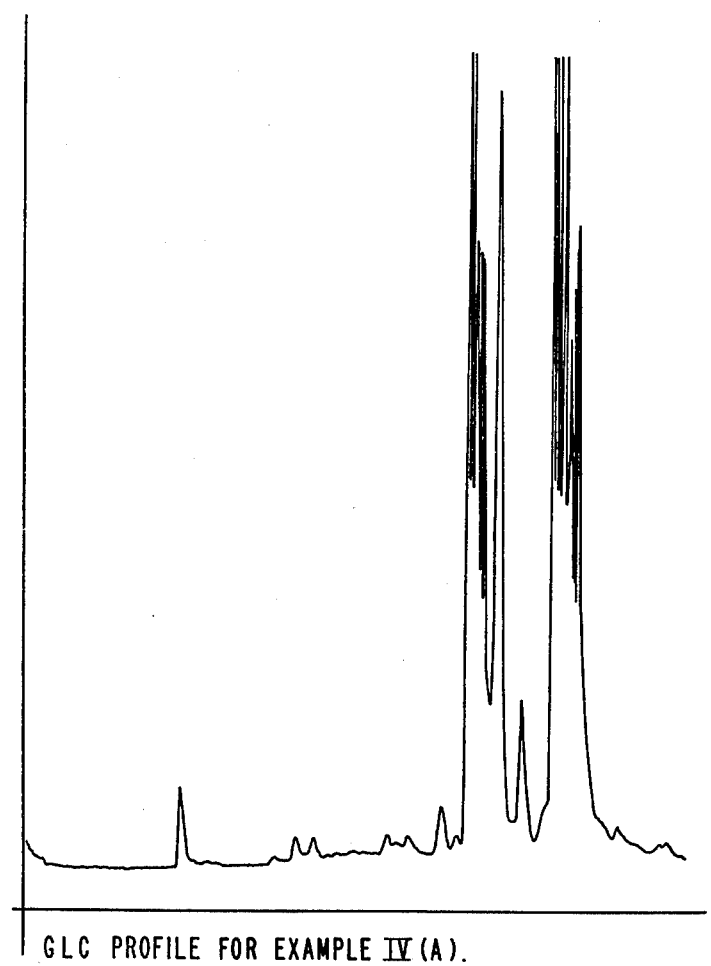

FIG. 35 is the GLC profile for bulked fractions 4–11 produced according to Example IVA wherein the two major peaks represent compounds having the structures:

Peak A 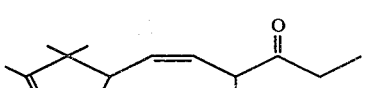

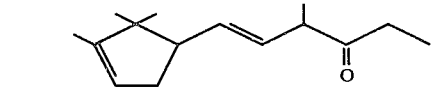

Peak B 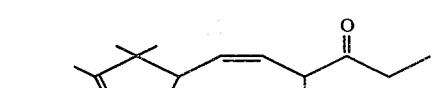

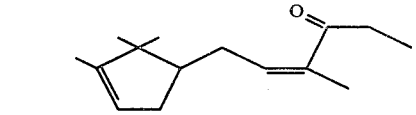

Figure 36:
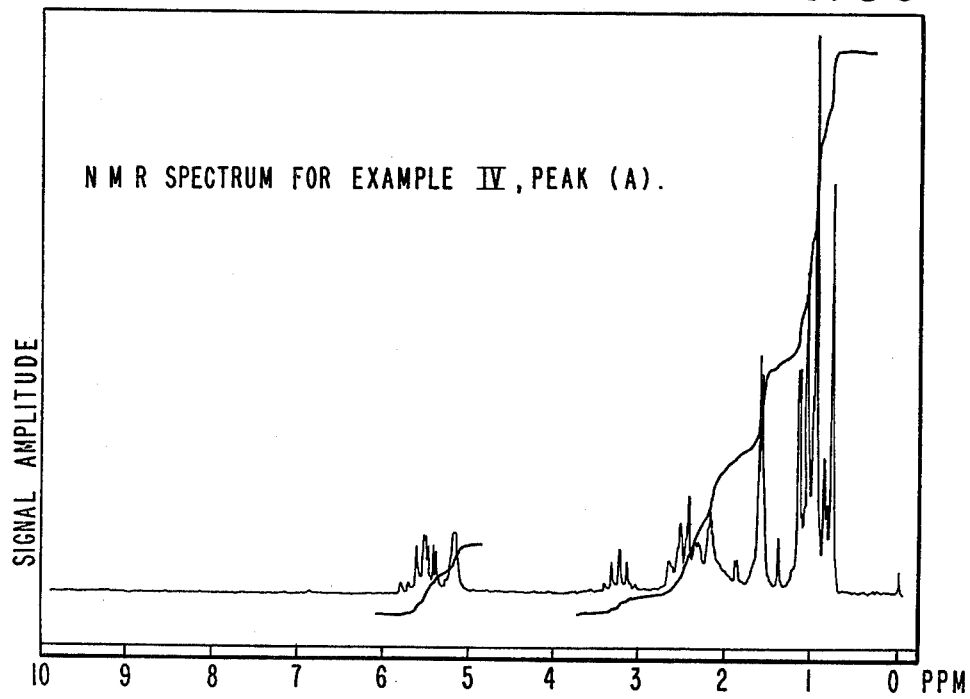

FIG. 36 is the NMR spectrum for Peak A of the reaction product according to Example IVA containing compounds having the structures:

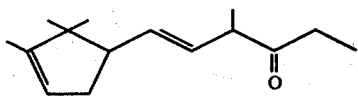

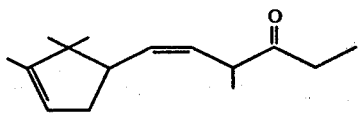

Figure 37:
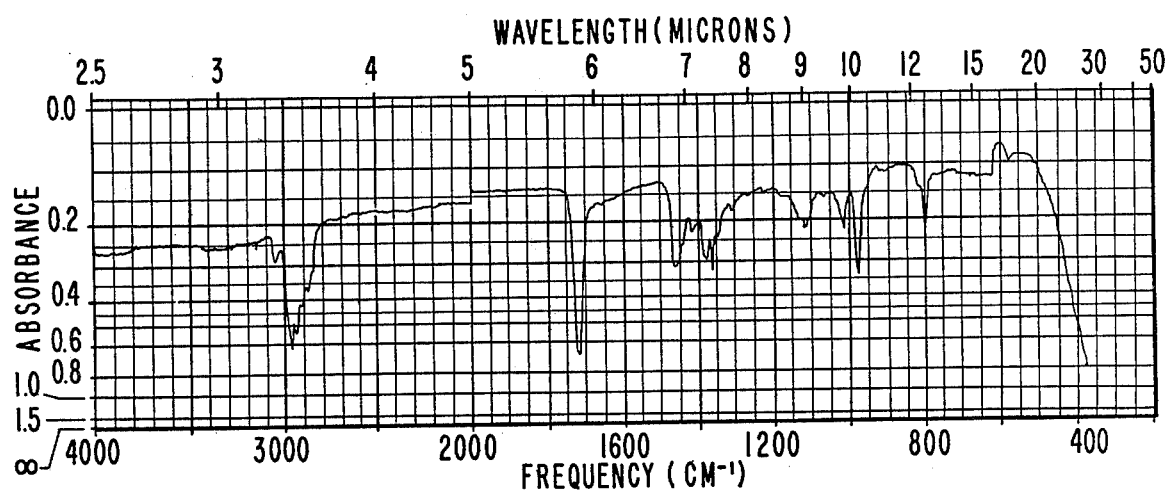

FIG. 37 is the infrared spectrum for peak A of the reaction product produced according to Example IVA.

Figure 38:
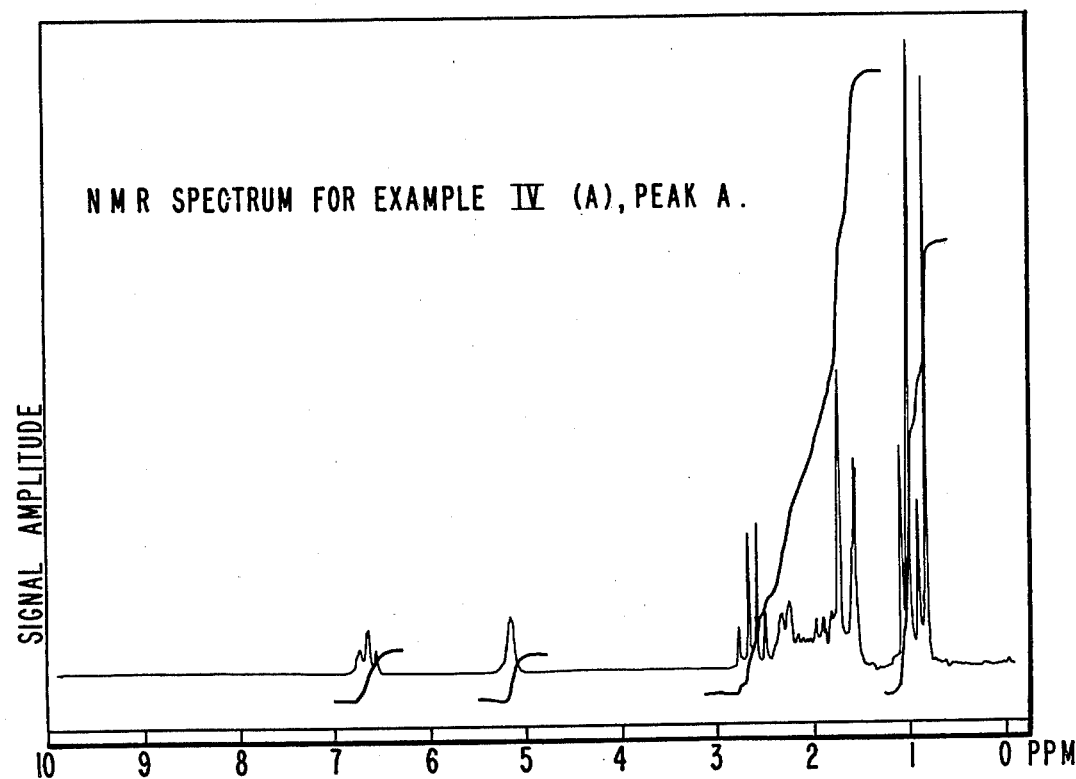

FIG. 38 is the NMR spectrum for peak B of the reaction product produced according to Example IVA.

Figure 39:
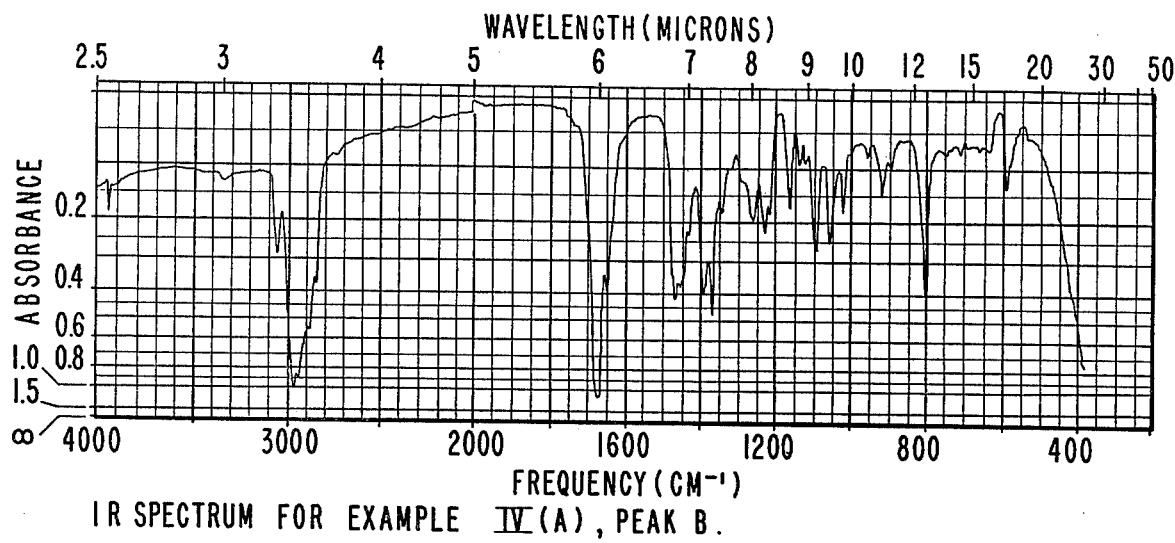

FIG. 39 is the infrared spectrum for peak B of the reaction product produced according to Example IVA containing compounds having the structures:

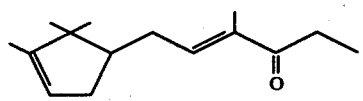

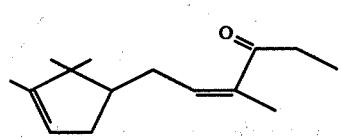

Figure 40:
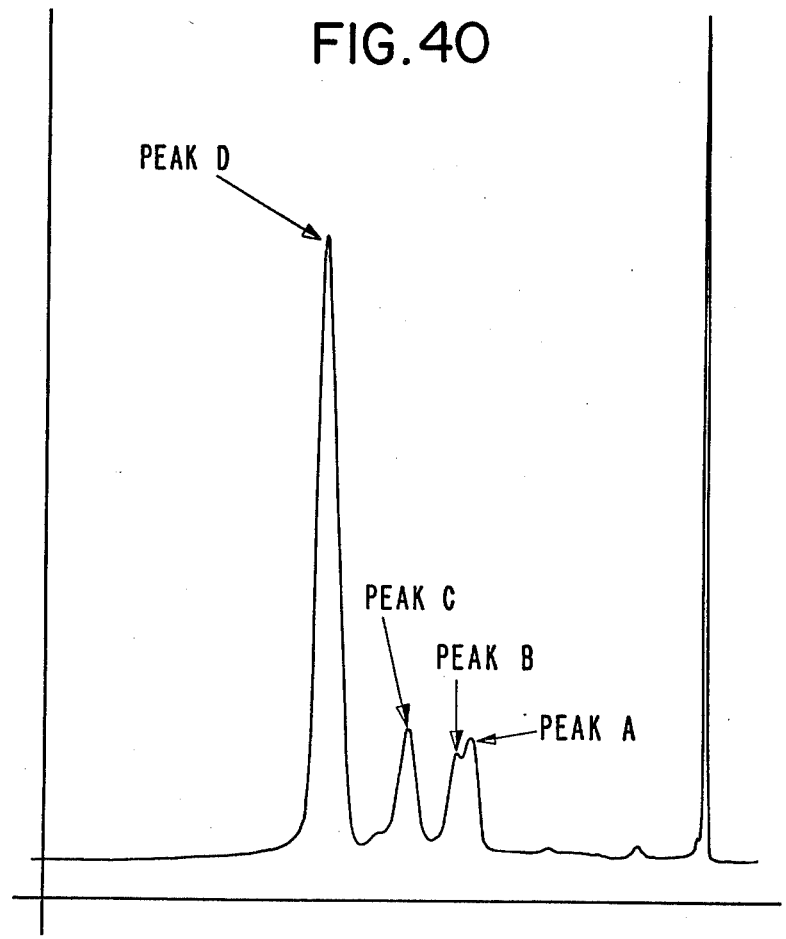

FIG. 40 is the GLC profile for the reaction product produced according to Example IVB wherein peaks A and B are four compounds having the structures:

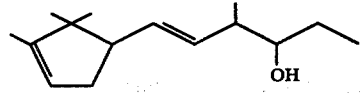

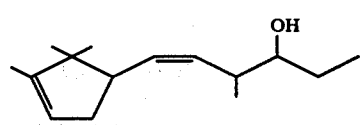

Peak C is for a compound having the structure:

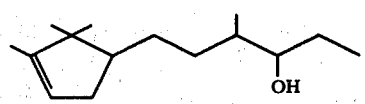

and peak D is for compounds having the structures:

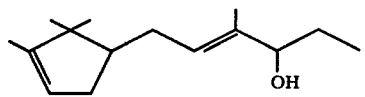

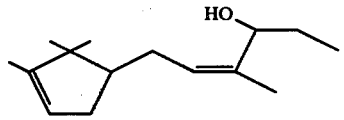

Figure 41:
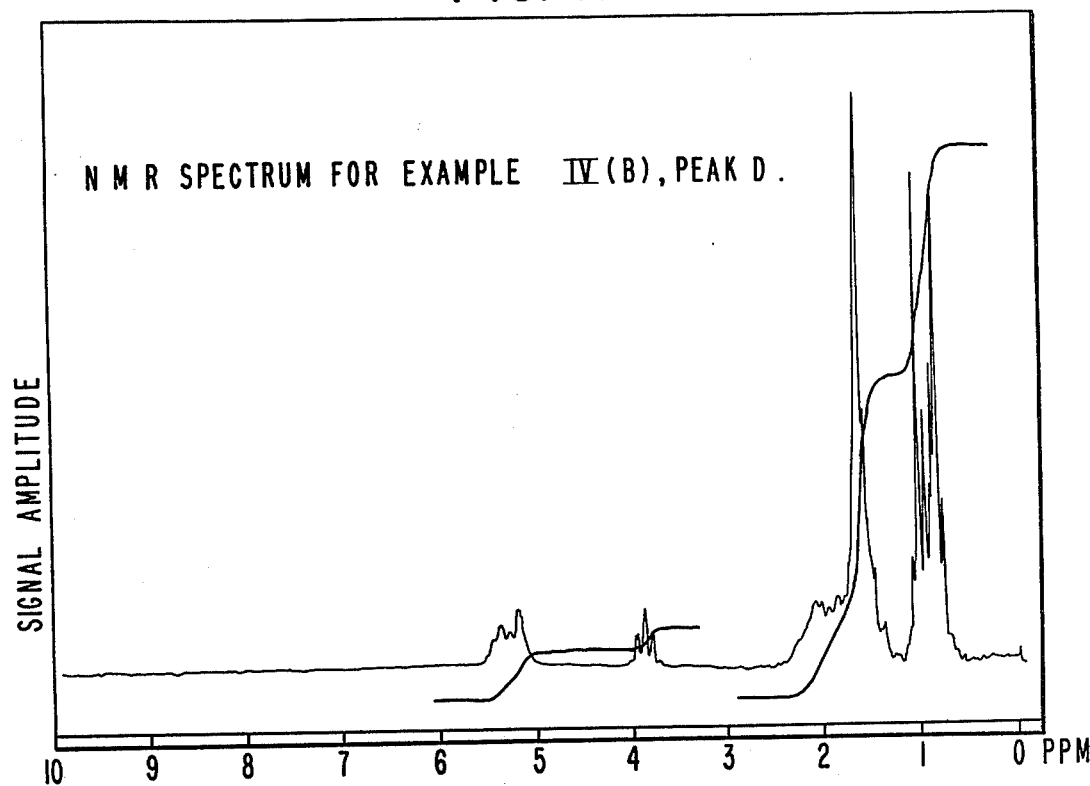

FIG. 41 is the NMR spectrum for peak D produced according to Example IVB containing compounds having the structures:

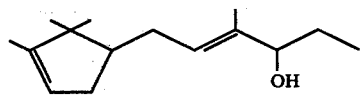

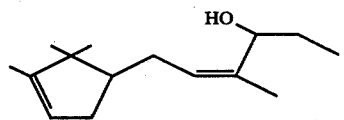

Figure 42:
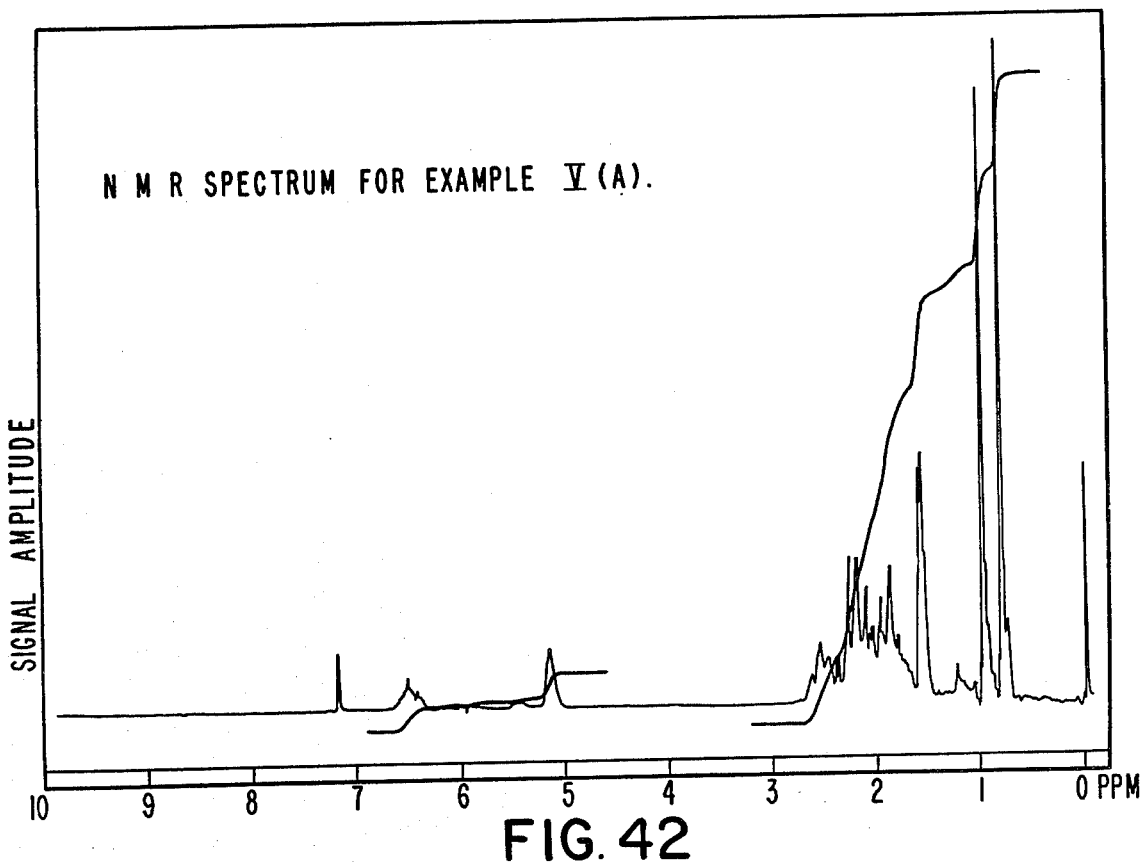

FIG. 42 is the NMR spectrum for the reaction product produced according to Example VA containing compounds having the structures:

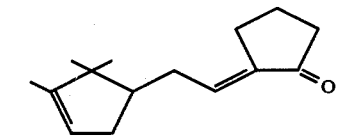

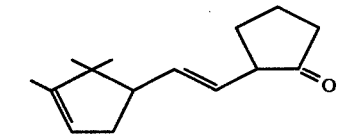

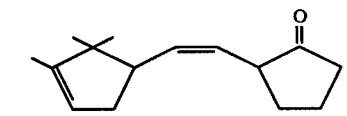

FIG. 43 is the infrared spectrum for the product produced according to Example VA containing compounds having the structures:

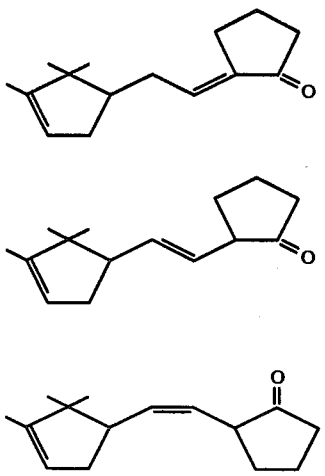

FIG. 44 is the NMR spectrum for the reaction product produced according to Example IVB containing compounds having the structures:

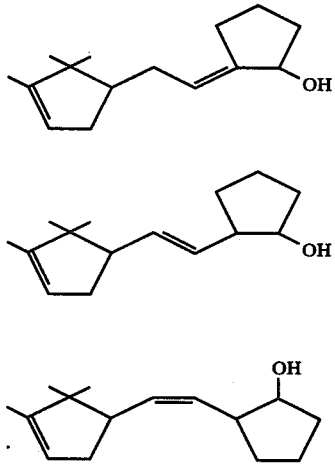

Figure 45:
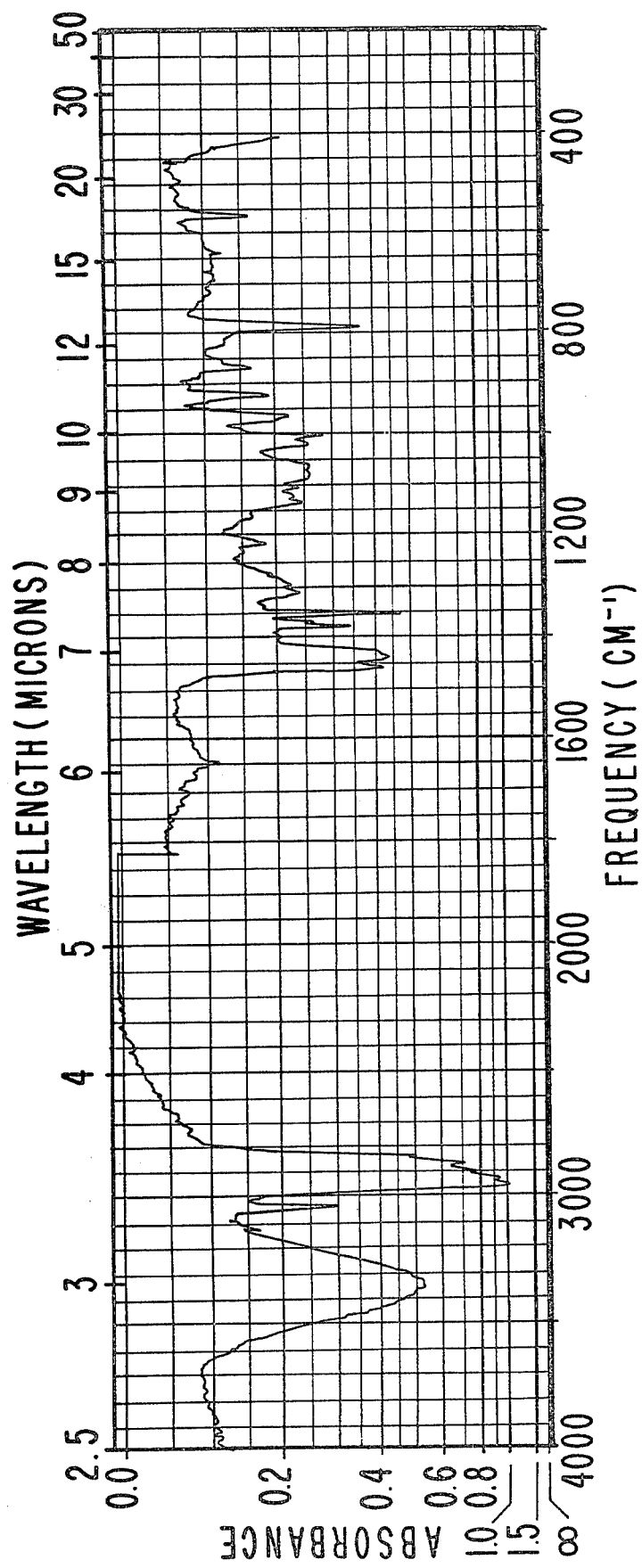

FIG. 45 is the infrared spectrum for the reaction product produced according to Example VB containing compounds having the structures:

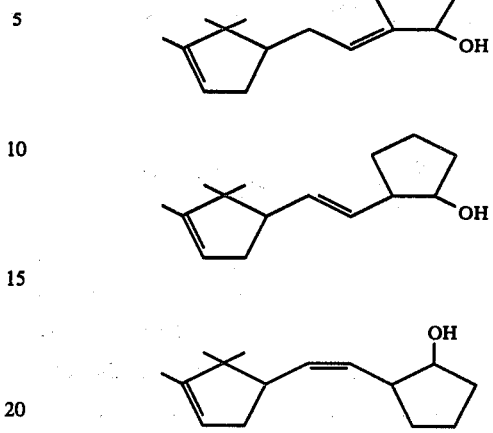

THE INVENTION

The invention comprises a novel process for preparing chemicals useful in formulating perfume compositions, perfumed articles and colognes, which chemicals have the generic structure:

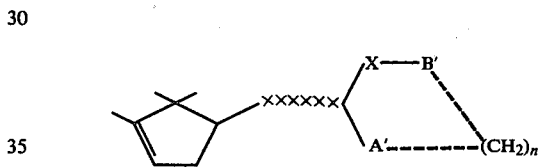

wherein one of the lines +++++ is a carbon-carbon double bond and the other of the lines +++++ is a carbon-carbon single bond; wherein X is carbinol having the structure:

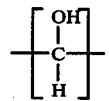

or carbonyl having the structure:

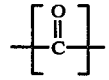

wherein A' is one of hydrogen, $CH_3$, $C_2H_5$ or $—CH_2—$; wherein B' is hydrogen, $CH_3$, $C_2H_5$ or $—CH_2—$; wherein n=0, 1 or 2; wherein each of the dashed lines are the same and each represents a single bond or no bond; wherein A' and B' are each $—CH_2—$ when n=1 or n=2 and the dashed line represents a single bond; or A' is hydrogen and B' is $C_2H_5$ or $CH_3$ or A' is $CH_3$ and B' is $CH_3$ or $C_2H_5$ when n=0 and each of the dashed lines represents no bond, the process comprising the first or both of the following reaction schemes:

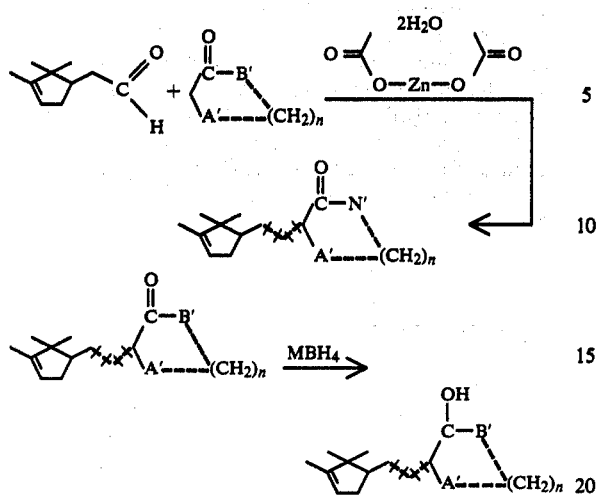

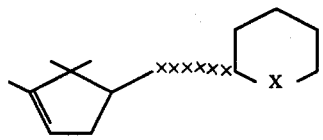

wherein M represents alkaline metal. The invention also comprises certain novel compounds, novel perfume compositions, novel perfumed articles and novel colognes prepared according to the above process and having the generic structure:

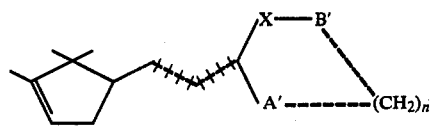

wherein one of the lines + + + + represents a carbon-carbon bond and the other of the lines + + + + represents a carbon-carbon double bond; and wherein X represents carbonyl having the structure:

or carbinol having the structure:

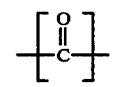

The specific embodiments of the foregoing invention are described hereinafter by way of example in accordance with which it is now preferred to practice the invention.

The 2,2,3-trimethyl-3-cyclopenten-1-ylalkenyl and alkylidene secondary alkanols, alkanones, cycloalkanols and cycloalkanones of our invention as defined by the structure:

are obtained by first carrying out an "aldol" condensation of campholenic aldehyde with an acyclic ketone containing three of four carbon atoms or a cyclic ketone containing six carbon atoms in the prsence of zinc acetate thereby forming a mixture of isomers of ketones wherein in the above generic structure X is carbonyl having the structure:

This reaction may be generically illustrated by the following reaction scheme:

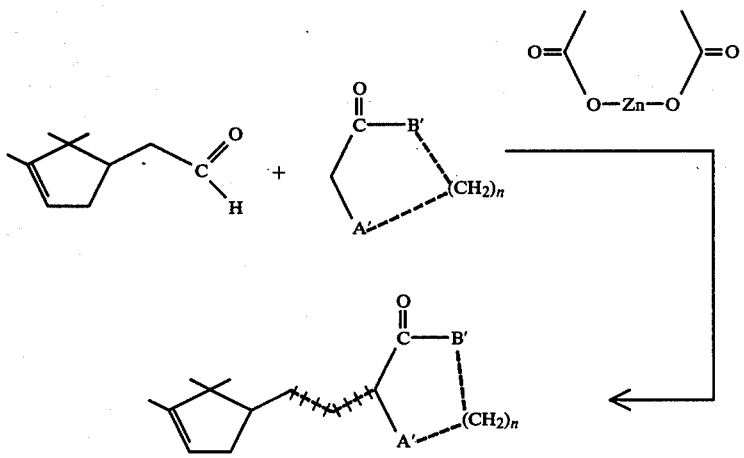

The campholenic aldehyde itself may be prepared by means of treatment of alpha pinene epoxide with Lewis acids, such as zinc bromide and zinc chloride thereby causing a rearrangement according to the reaction scheme:

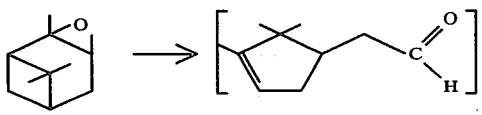

More specifically, the first step of the process of our invention may be specifically illustrated by the following reaction schemes:

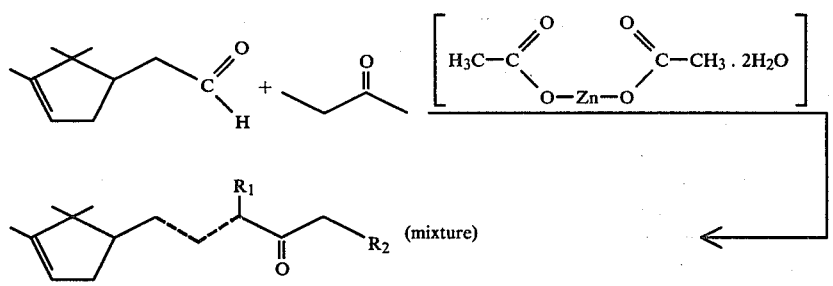

wherein either of $R_1$ or $R_2$ is methyl and the other of $R_1$ or $R_2$ is hydrogen and one of the dashed lines is a carbon-carbon double bond and the other of the dashed lines is a carbon-carbon single bond;

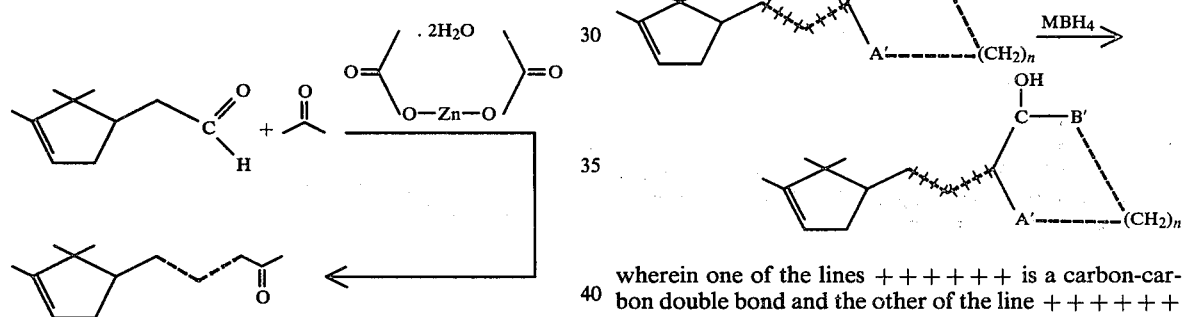

wherein one of the dashed lines is a carbon-carbon double bond and the other of the dashed lines is a carbon-carbon single bond; and

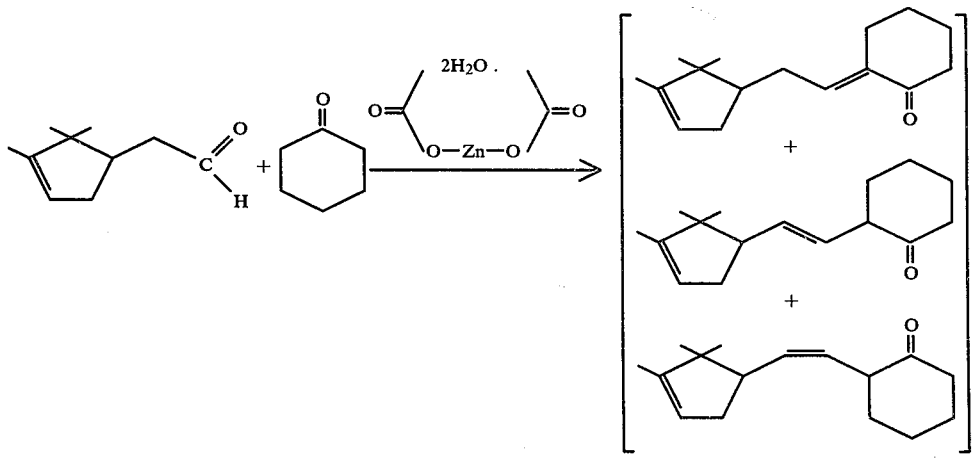

The resulting ketone mixture may then be subjected to reduction using alkaline metal borohydrides such as sodium borohydride to produce a mixture of alcohols or the resulting mixture may be used as is in perfumery for perfume mixtures or perfumed articles or colognes or the resulting mixture of ketones may be separated into their respective component isomers and used as is or individually reduced using alkaline metal borohydrides.

In the event that it is desired to reduce said ketone mixture or said individual ketones to the corresponding mixture of alcohols or individual alcohols, the reaction utilized may be illustrated by the following reaction scheme:

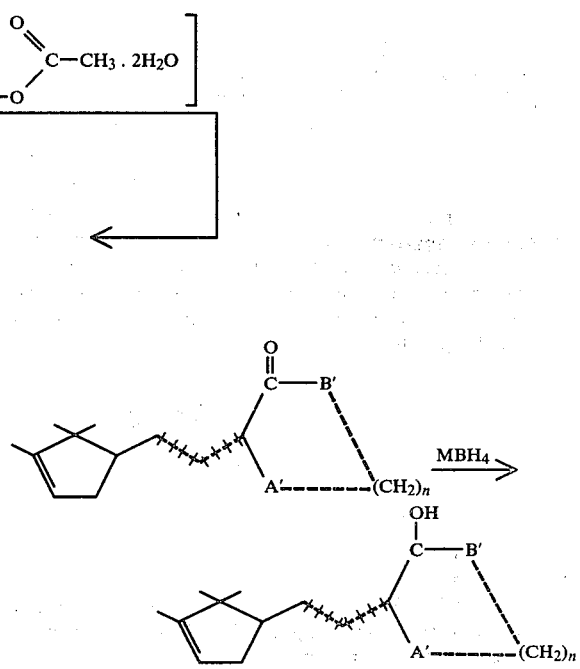

wherein one of the lines ++++++ is a carbon-carbon double bond and the other of the line ++++++ is a carbon-carbon single bond; wherein A' is hydrogen, methyl or —$CH_2$—; wherein B' is hydrogen, $CH_3$, $C_2H_5$ or —$CH_2$—; where n is 0, 1 or 2; wherein each of the dashed lines are the same and each represents a single bond or no bond at all; wherein A' and B' each represent —$CH_2$— when n=1 or n=2 and each of the dashed lines represents a single bond; or A' is hydrogen and B' is C₂H₅ or CH₃ or A' is CH₃ and B' is CH₃ or C₂H₅ when n=0 and the dashed line represents no bond at all. More specifically, the reduction reaction may be illustrated by the following reaction sequences:

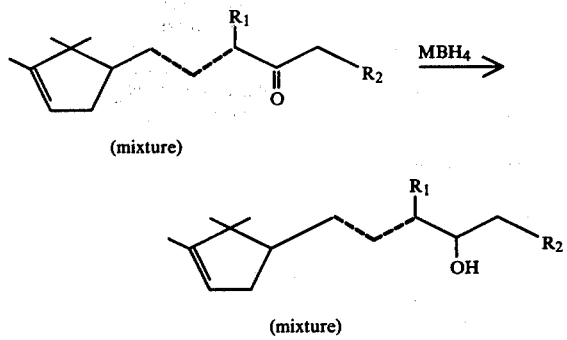

(mixture)

wherein one of R₁ or R₂ is methyl and the other of R₁ or R₂ is hydrogen and wherein one of the dashed lines is a carbon-carbon single bond;

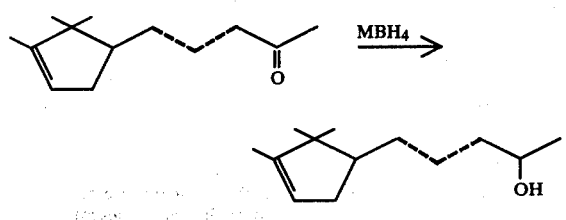

wherein one of the dashed lines is a carbon-carbon single bond and the other of the dashed lines is a carbon-carbon double bond; and

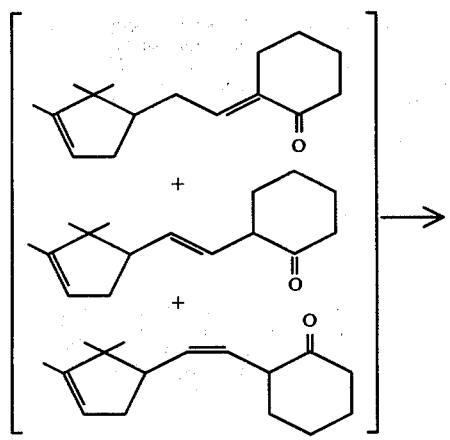

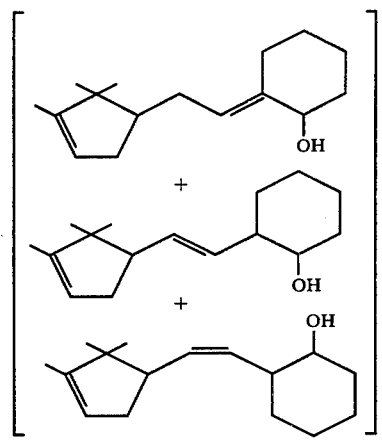

wherein M is alkaline metal such as sodium or potassium.

In carrying out the first step of the process of our reaction forming ketones by means of reacting campholenic aldehyde with C₃ or C₄ ketone, the catalyst contemplated herein are zinc acetate and zinc acetate dihydrate. The zinc acetate dihydrate is preferred since it gives rise to a higher yield of desired product useful in perfumery, perfumed articles and colognes.

The mole ratio of catalyst: ketone reactant is in the range of 0.05 up to 1.0 mole per mole of ketone reactant; preferably about 0.2 moles of catalyst per mole of ketone reactant.

The range of mole ratio of ketone reactant: campholenic aldehyde reactant is in the range of from about 10:1 to about 1:1, with a preferred mole ratio range of ketone: campholenic aldehyde of 3:1 up to 5:1.

The temperature of the aldol condensation reaction using the zinc acetate or zinc acetate dihydrate is between 100° C. and 250° C., preferably in the range of from about 130° C. up to about 200° C.

Although atmospheric pressure may be used, it is preferred to operate the aldol condensation reaction at pressures in the range of from about 100 psig up to about 400 psig depending on the scale and size of the autoclave used and correspondingly it is preferred to carry out the reaction in an autoclave suited for pressures up to about 500 psig.

The reaction may be monitored using vapor phase chromotography techniques. At the end of the reaction the reaction mass is "worked up" using standard techniques, for example, filtration, neutralization, drying and fractional distillation. The individual isomers may be also separated using preparative GLC, if desired. Usually if the ketone mixture is to be further reacted such separation is not commercially feasible.

The step of reducing the ketone(s) to the corresponding alcohol without reduction of double bonds contained in cyclopentenyl ring or in the alkenyl side-chain is carried out using an alkaline metal borohydride catalyst, for example, sodium borohydride or potassium borohydride.

The reaction also is to take place in the presence of an inert solvent such as anhydrous methanol, anhydrous ethanol or anhydrous isopropylalcohol. The temperature of reaction is between 0° C. and 40° C.; preferably between 15° C. and 30° C. The most convenient pressure to use is one atmosphere, however, higher pressures may be used without reduction in yield or conversion.

The concentration of alkaline metal borohydride in the reaction mass may vary from 10 grams per liter up to 200 grams per liter with a preferred range of catalyst concentration of between 40 and 80 grams per liter of alkaline metal borohydride.

The concentration of ketone reactant in the reaction mass may vary from 500 grams per liter up to 1000 grams per liter with a preferred range of from 700 up to 800 grams per liter.

The ratio of alkaline metal borohydride catalyst to ketone reactant may vary from 0.05:1 up to 0.3:1 with a preferred range of weight ratios of catalyst: ketone reactant being from 0.08:1 up to about 0.12:1.

The reduction reaction may be monitored using GLC techniques, if desired. At the end of the reaction, the reaction mass is "worked up" using standard physical "work up" procedures including extraction, neutralization, drying and fractional distillation. Furthermore, if desired, a fractionally distilled material which conveniently is a mixture of isomers of alcohols, may be further separated using preparative GLC techniques.

Specific examples of 2,23-trimethyl-3-cyclopenten-1-ylalkenyl and alkylidene secondary alkanols, alkanones, cycloalkanols and cycloalkanones produced using the aforementioned process and their perfumery properties are as follows, as set forth in Table II below.

TABLE II

| Structure of 2,2,3-trimethyl-3-cyclopenten-1-ylalkenyl and alkylidene secondary alkanols, alkanones, cycloalkanols and cycloalkanones in mixtures | Aroma of Mixtures |
|---|---|
| Mixture of compounds each of which is defined within the genus having the structure:<br />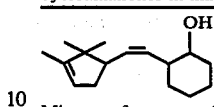 wherein one of the dashed lines is a carbon-carbon single bond and the other of the dashed lines is a carbon-carbon double bond and wherein one of $R_1$ or $R_2$ is methyl and the other of $R_1$ or $R_2$ is hydrogen | At 10% in food grade ethanol, a sweet, woody, (sandalwood) ionone-like aroma with green, melony nuances. |
| Mixture of compounds defined by the generic structure:<br />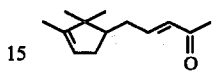 wherein one of the dashed lines is a carbon-carbon single bond and the other of the dashed lines is a carbon-carbon double bond and one of $R_1$ or $R_2$ is methyl and the other of $R_1$ or $R_2$ is hydrogen. | A powerful sandalwood note, with nutty, oily nuances having intense musky nuances also. |
| Mixture of compounds having the structures:<br />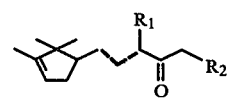<br />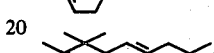 | A cedarwood, sandalwood sweet aroma |

TABLE II-continued

| Structure of 2,2,3-trimethyl-3-cyclopenten-1-ylalkenyl and alkylidene secondary alkanols, alkanones, cycloalkanols and cycloalkanones in mixtures | Aroma of Mixtures |
|---|---|
| Mixture of compounds having the structures:<br />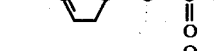<br />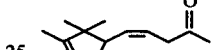<br />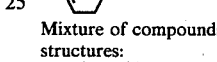<br />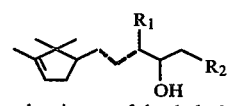 | At 10% in foodgrade ethanol, a sweet floral, ionone-like soft fruity (apricot) aroma with nutty, woody and slight sandalwoody nuances |
| Mixture of compounds having the structures:<br />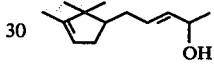<br /><br />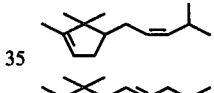<br />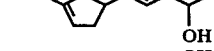 | A sandalwoody aroma with resinous topnote. |
| Compound defined by the structure:<br />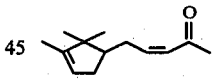 | A fruity, ionony, green, somewhat buttery aroma |
| Compound defined by the structure:<br />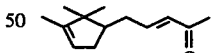 | A floral ionone, violets-like aroma with a slightly fatty rue oil note. |
| Mixture of compounds having the structures:<br />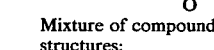<br />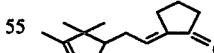<br />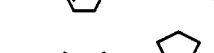 | A low-keyed woody, amber aroma with a slight spiciness |
| Mixture of compounds having the structures:<br />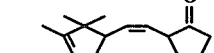<br />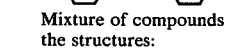<br />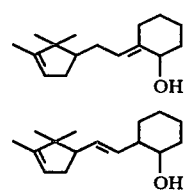 | A low-keyed woody, sandlewood-like note with "cyclamal/lilial" type character. |

TABLE II-continued

| Structure of 2,2,3-trimethyl-3-cyclopenten-1-ylalkenyl and alkylidene secondary alkanols, alkanones, cycloalkanols and cycloalkanones in mixtures | Aroma of Mixtures |
| --- | --- |
| 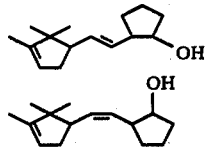 | |

One or more of the above-mentioned 2,2,3-trimethyl-3-cyclopenten-1-ylalkenyl and alkylidene secondary alkanols, alkanones, cycloalkanols and cycloalkanones or mixtures of 2,2,3-trimethyl-3-cyclopenten-1-ylalkenyl and alkylidene secondary alkanols, alkanones, cycloalkanols and cycloalkanones defined according to the generic structure:

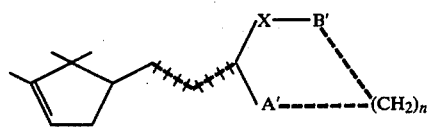

wherein one of the lines + + + + + + is a carbon-carbon double bond and the other of the lines + + + + + + is a carbon-carbon single bond; wherein X is carbinol having the structure:

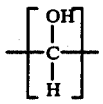

or carbonyl having the structure:

wherein A' is hydrogen, $CH_3$ or $-CH_2-$; wherein B' is H, $CH_3$, $C_2H_5$ or $-CH_2-$; wherein n=0 or 2; wherein the dashed line is a carbon-carbon single bond or represents no bond; wherein when A' and B' are each $-CH_2-$, n=2 and the dashed lines are each carbon-carbon single bonds; or when A' is hydrogen and B' is $C_2H_5$ or $CH_3$, or when A' is methyl and B' is methyl or $C_2H_5$, n=0 and the dashed line represents no bond is an olfactory agent and can be incorporated into a wide variety of compositions each of which will be enhanced or augmented by its rich, musky and/or cedar woody and/or sandalwood and/or green, earthy and/or ionone-like and/or sweet, fruity and/or sweet floral notes. The 2,2,3-trimethyl-3-cyclopenten-1-ylalkenyl and alkylidene secondary alkanols, alkanones, cycloalkanols and cycloalkanones can be added to perfume compositions as pure compounds or can be added to mixtures of materials in fragrances imparting compositions to provide a desired fragrance character to a finished perfume material. The perfume and fragrance compositions obtained according to our invention are suitable in a wide variety of perfume articles and can be also used to enhance, modify or reenforce natural fragrance materials. It will thus be appreciated that the 2,2,3-trimethyl-3-cyclopenten-1-ylalkenyl and alkylidene secondary alkanols, alkanones, cycloalkanols and cycloalkanones of our invention is (are) useful as olfactory agent(s) and fragrance(s).

The term "perfume composition" is used herein to mean a mixture of compounds including, for example, natural oils, synthetic oils, alcohols other than those covered by the alcohols produced according to this invention, aldehydes, alcohols other than those alcohols produced according to the processes of our invention, ketones other than those ketones produced according to the processes of our invention, esters, lactones, nitriles and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh-smelling materials. Such perfume compositions of our ivnention can be used in conjunction with carriers, vehicles, solvents, dispersants, emulsifiers, surface-active agents, aerosol propellants and the like.

In perfume compositions the individual components contribute their particular olfactory characteristics, but the overall effect of the perfume composition will be the sum of the effect of each ingredient. Thus, one or more of the 2,2,3-trimethyl-3-cyclopenten-1-ylalkenyl and alkylidene secondary alkanols, alkanones, cycloalkanols and cycloalkanones of our invention can be used to alter, augment, modify or enhance the aroma characteristics of a perfume composition or a perfumed article, for example by highlighting or moderating the olfactory reaction contributed by another ingredient of the composition.

The amount of one or more of the 2,2,3-trimethyl-3-cyclopenten-1-ylalkenyl and alkylidene secondary alkanols, alkanones, cycloalkanols and cycloalkanones of our invention which will be effective in perfume compositions depends upon many factors, including the other ingredients, their amounts and the effects which are desired. It has been found that perfume compositions containing as much as 40% or as little as 0.1 ppm (0.00001%) by weight of the mixtures or compounds produced according to the process of our invention or the mixtures or compounds of this invention or even less can be used to impart a rich musky and/or cedar-woody and/or sandalwood and/or green earthy and/or ionone-like and/or sweet floral aroma to soaps, cosmetics and other products. The amount employed will depend upon considerations of cost, nature of the end product, the effect desired in the finished product and the particular fragrance sought.

One or more of the 2,2,3-trimethyl-3-cyclopenten-1-yl-alkenyl and alkylidene secondary alkanols, alkanones, cycloalkanols and cycloalkanones of our invention as disclosed herein can be used alone, in a fragrance modifying composition or in a perfume composition as an olfactory component in detergents (anionic detergents, cationic detergents and nonionic detergents) and soaps; space deodorants; perfumes; colognes, bath preparations such as bath oil, bath salts; hair preparations such as lacquers, brilliantines, pomades, and shampoos; cosmetic preparations such as cremes, deodorants, hand lotions, sun screens; powders such as talcs, dusting powders, face powders and the like. When one or more of the 2,2,3-trimethyl-3-cyclopenten-1-ylalkenyl and alkylidene secondary alkanols, alkanones, cycloalkanols and cycloalkanones of our invention is used in perfumed articles such as the foregoing, it can be used in amounts of 0.5 ppm (0.00005%) or lower. Generally it is preferred not to use less than about 0.2% no more than about 25% in the finished perfumed article, since the use of too much will tend unbalance the total aroma and will needlessly raise the cost of the article.

The following examples serve to illustrate embodiments of the invention as it is now preferred to practice it. It will be understood that these examples are illustrative and the invention is to be restricted thereto only as indicated in the appended claims.

EXAMPLE IA

PREPARATION OF CAMPHOLENIC ALDEHYDE

REACTION:

| Fr. | Vapor Temp(°C.) | Liquid Temp(°C.) | Vac (mmHg) | Weight (g) | Product (g) |
|---|---|---|---|---|---|
| 1 | 35–46 | 51–100 | 90 | 2284 | 62 |
| 2 | 46–83 | 86–96 | 10 | 188 | 156 |
| 3 | 83–84 | 96–153 | 10 | 549 | 510 |
| 4 | 84–90 | 153–202 | 10 | 50 | 40 |

Figure 1:
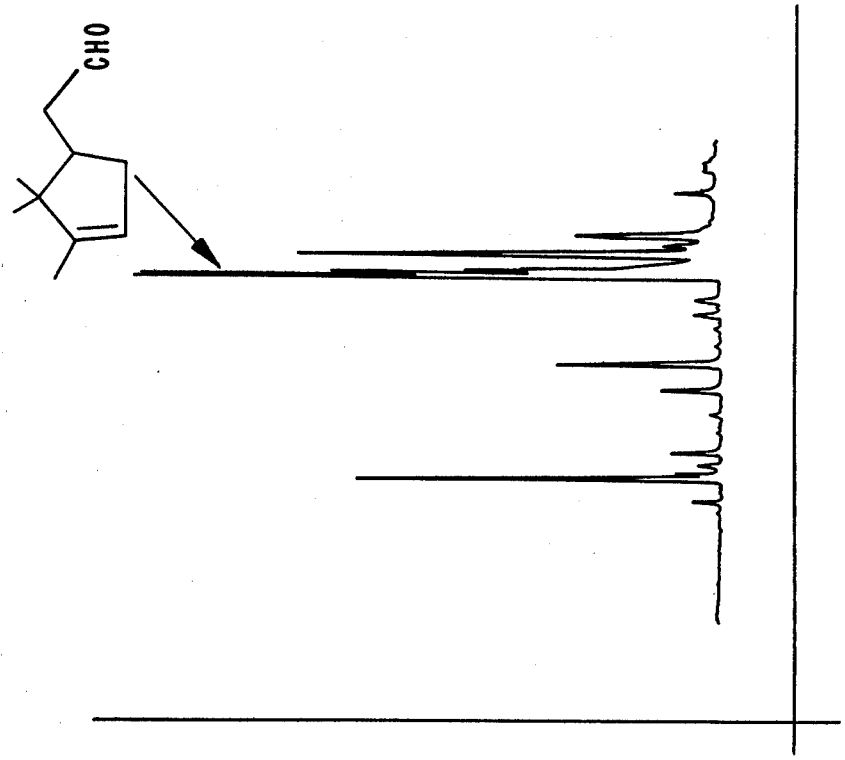
FIG. 1 is the GLC profile for the product produced according to the process of Example IA having the structure.

FIG. 1 is the GLC profile for the reaction product of this example prior to fractional distillation.

FIG. 2 is the GLC profile of fraction 3 subsequent to the rush over distillation which includes campholenic aldehyde.

FIG. 3 is the infrared spectrum for campholenic aldehyde produced according to this example.

EXAMPLE IB

PREPARATION OF MIXTURE OF 3-METHYL-5-(2,2,3-TRIMETHYL-3-CYCLOPENTENE-1-YL)-3(OR 4)-PENTENE-2-ONE AND 6-(2,2,3-TRIMETHYL-3-CYCLOPENTENE-1-YL)-4(OR 5)-HEXENE-3-ONE

REACTION:

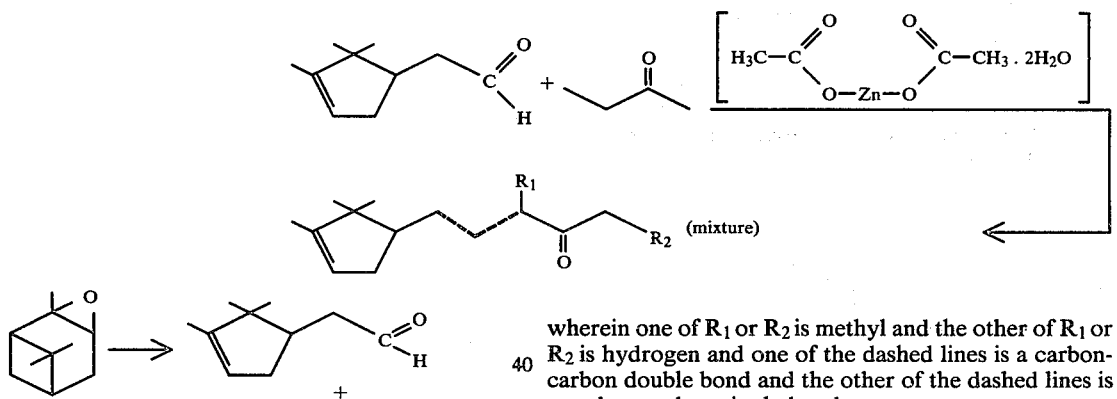

wherein one of $R_1$ or $R_2$ is methyl and the other of $R_1$ or $R_2$ is hydrogen and one of the dashed lines is a carbon-carbon double bond and the other of the dashed lines is a carbon-carbon single bond.

Into a 5 liter flask reaction vessel equipped with reflux condenser thermometer stirrer and heating mantle and addition funnel is added 15.9 grams of zinc metal (0.21 moles) and 86 ml tetrahydrofuran. 40.3 grams of 1,2-dibromoethane is added at reflux dropwise over a period of 1 hour (reflux temperature=73° C.). After the addition is completed, the reaction mass is stirred at reflux for a period of 3 hours (76° C.). 430 ml toluene is then added and the reaction system is set up for tetrahydrofuran/toluene recovery.

The reaction mass is then transferred to a 5 liter flask and 2145 grams of toluene are added. Alpha-pinene epoxide (1086 grams, 7.1 moles) is then added over a period of 1 hour while maintaining the reaction mass temperature below 53° C. using dry-ice/isopropanol bath in order to control exotherm. The reaction mass is then stirred for an additional 2 hours after addition is complete. The reaction mass is then intimately admixed with a 10% acetic acid solution to a pH of 4.3 followed by neutralization with sodium bicarbonate and sodium chloride solutions. The toluene is then recovered and the reaction mass crude material is "rush over" distilled whereby 785.3 grams of product is collected. (Chemical yield=74%). The rush over distillation fractions are collected using a 2 inch rush over column packed with saddle stones yielding the following fractions:

Into a 2 liter autoclave are charged 152 grams of 2,2,3-trimethyl-3-cyclopetene-1-yl acetaldehyde produced according to example IA, 220 grams of methyl ethyl ketone and 44 grams of zinc acetate dihydrate. The reaction mixture is heated at 180° C. for a period of 10 hours. After cooling, the reaction mixture is filtered to remove the zinc acetate dihydrate catalyst and washed with 200 ml of saturated sodium chloride solution. Distillation at 4.0 mmHg pressure yields 172 grams of crude product. Redistillation at 3.0 mmHg pressure gives 142 grams of pure product, boiling point 115°-122° C. at 3.0 mmHg pressure.

The fractionation data resulting from the redistillation is as follows:

| No. | Vapor Temp(°C.) | Liquid Temp(°C.) | Vac. mmHg | Fraction Weight (grams) |
|---|---|---|---|---|
| 1 | 50–64 | 111–120 | 3 | 11.1 |
| 2 | 64–115 | 120–139 | 3 | 20.7 |
| 3 | 115 | 139 | 3 | 20.5 |
| 4 | 115–116 | 139 | 3 | 17.2 |
| 5 | 116–118 | 139 | 3 | 18.9 |
| 6 | 118 | 139–141 | 3 | 21.8 |
| 7 | 118–120 | 141–143 | 3 | 19.3 |
| 8 | 120–122 | 143–150 | 3 | 19.8 |
| 9 | 122 | 150–175 | 3 | 10.3 |

FIG. 4 is the GLC profile for the reaction product (conditions: 10′×¼ inch carbowax column programmed at 10° C. per minute).

FIG. 5 is the NMR spectrum for the reaction product which contains compounds having the structures:

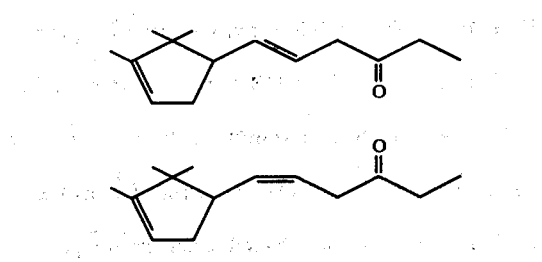

FIG. 6 is the infrared spectrum for the reaction product containing compounds having the structures:

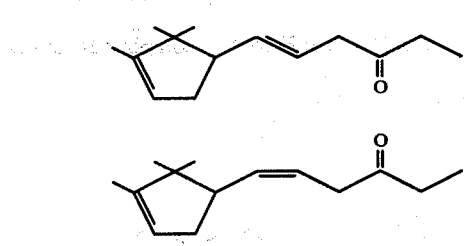

FIG. 7 is the NMR spectrum for the reaction product having the structures:

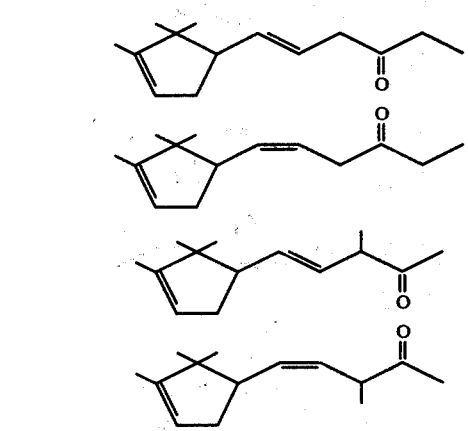

FIG. 8 is the infrared spectrum for the reaction product having the structures:

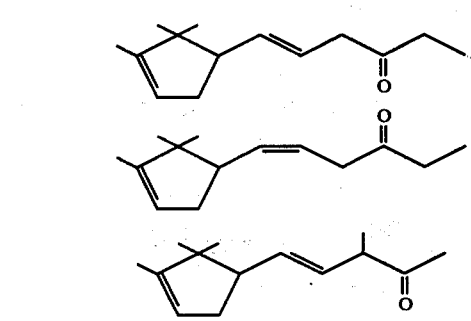

-continued

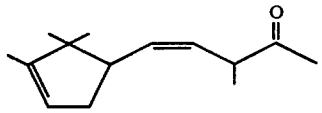

FIG. 9 is the NMR spectrum for the reaction product having compounds having the structures:

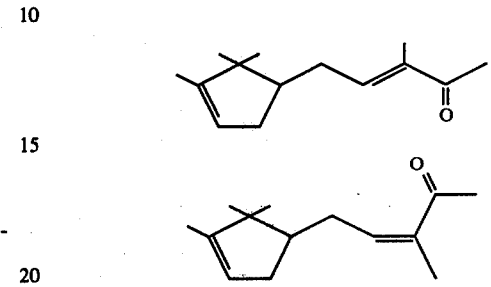

FIG. 10 is the infrared spectrum of the reaction product containing compounds having the structures:

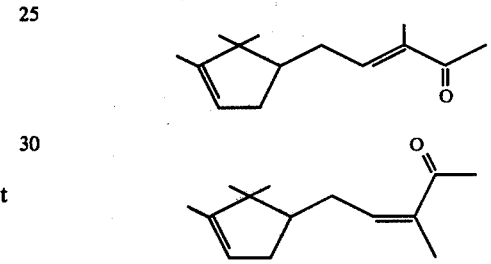

FIG. 11 is the NMR spectrum for that fraction of the reaction product having compounds having the structures:

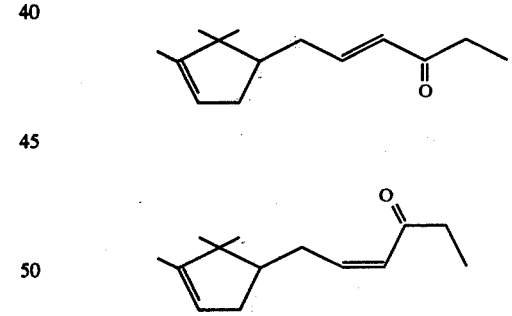

EXAMPLE IC

PREPARATION OF MIXTURE OF 3-METHYL-5-(2,2,3-TRIMETHYL-3-CYCLOPENTENE-1-YL)-3(OR 4)-PENTEN-2-OL AND 6-(2,2,3-TRIMETHYL-3-CYCLOPENTENE-1-YL)-4(OR 5)-HEXENE-3-OL

REACTION:

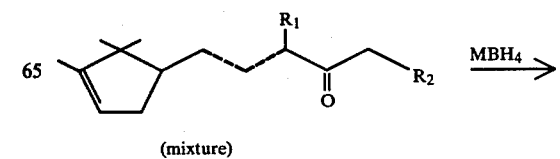

(mixture)

-continued

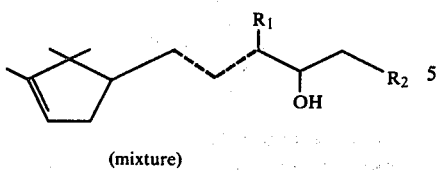

(mixture)

wherein one of the dashed lines represents a carbon-carbon double bond and the other of the dashed lines represents a carbon-carbon single bond and one of $R_1$ or $R_2$ is methyl and the other of $R_1$ or $R_2$ is hydrogen and M is sodium.

In a 250 ml three-necked reaction flask is placed a solution of 71 grams of a mixture of 3-methyl-5-(2,2,3-trimethyl-3-cyclopenten-1-yl)-3(or 4)-pentene-2-one and 6-(2,2,3-trimethyl-3-cyclopenten-1-yl)-4(or 5)-hexene-3-one prepared according to Example IB in 80 ml of anhydrous methanol. To this material is added a solution of 6.5 grams of sodium borohydride in 20 ml of methanol over a period of 10 minutes while maintaining the reaction mixture at 20°-23° C. The reaction mixture is then stirred at room temperature for a period of 2 hours, and after stirring 50 ml of a 10% aqueous acetic acid solution is added while maintaining the reaction mass at a temperature of about 25° C. The resulting organic layer is separated from the reaction mass and washed with saturated sodium bicarbonate solution and saturated sodium chloride solution. Distillation at 3 mmHg pressure yields 56 grams of a crude product which is redistilled at 2.0 mmHg pressure to obtain 54 grams (76% yield of theory) of pure product having a boiling point 115°-122° C. at 2.0 mm Hg pressure.

The fractionation data is as follows:

| No. | Vapor Temp(°C.) | Liquid Temp(°C.) | Vac. mm Hg | Fraction weight (grams) |
|---|---|---|---|---|
| 1 | 100-114 | 100-120 | 2.0 | 2.6 |
| 2 | 114-115 | 120 | 2.0 | 6.1 |
| 3 | 115-116 | 120 | 2.0 | 5.2 |
| 4 | 116-117 | 120-122 | 2.0 | 5.7 |
| 5 | 117 | 122 | 2.0 | 5.5 |
| 6 | 117-118 | 122-123 | 2.0 | 6.0 |
| 7 | 118-120 | 123-125 | 2.0 | 6.5 |
| 8 | 120 | 125 | 2.0 | 6.4 |
| 9 | 120 | 125-130 | 2.0 | 6.2 |
| 10 | 120-121 | 130-150 | 2.0 | 2.9 |
| 11 | 121-122 | 150-180 | 2.0 | 1.2 |

Preparative GLC yields 6 peaks, designated "A", "B", "C", "D", "E" and "F".

FIG. 13 sets forth the NMR spectrum for peak A.

FIG. 14 sets forth the NMR spectrum for peak B.

FIG. 15 sets forth the NMR spectrum for peak C.

FIG. 16 sets forth the infrared spectrum for peak C.

FIG. 17 sets forth the NMR spectrum for peak D.

FIG. 18 sets forth the infrared spectrum for peak D.

FIG. 19 sets forth the NMR spectrum for peak E.

FIG. 20 sets forth the infrared spectrum for peak E.

FIG. 21 sets forth the NMR spectrum for peak F.

FIG. 22 sets forth the infrared spectrum for peak F.

Peaks A, B, C, D, E and F contain compounds having the structures as follows:

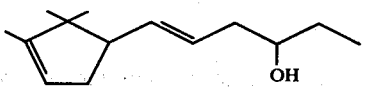

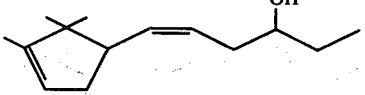

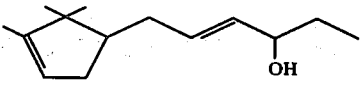

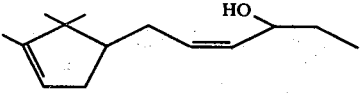

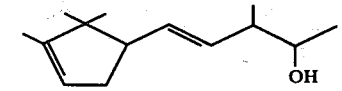

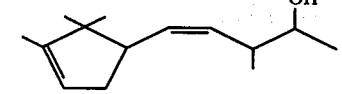

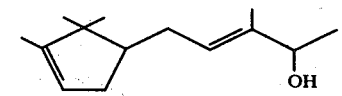

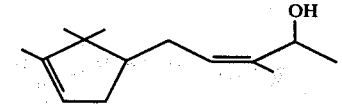

EXAMPLE IIA

PREPARATION OF CAMPHOLENYLIDENE CYCLOHEXANONE

REACTION:

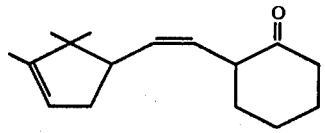

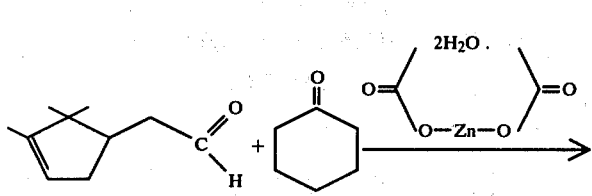 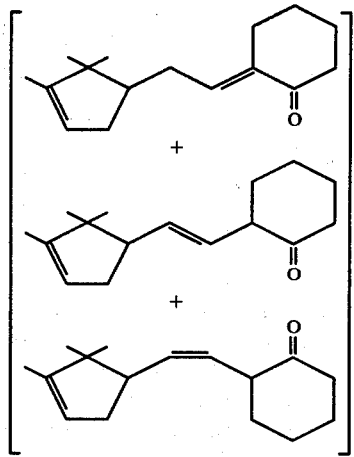

Into a 2 liter autoclave capable of being pressurized to 20 atmospheres are charged 152 grams of (1.0 moles) campholenic aldehyde, 490 grams (5.0 moles) of cyclohexanone and 44 grams (0.2 moles) of zinc acetate dihydrate. The contents of the autoclave are heated to 180° C. and at a pressure of 160–170 psig for a period of 10 hours. At the end of the 10 hour period, the reaction mass is cooled and solids are filtered and washed neutral with sodium bicarbonate and aqueous sodium chloride.

The resulting reaction product is distilled through a splash column containing saddle stones yielding the following fractions:

| No. | Vapor Temp (°C.) | Liquid Temp (°C.) | Vac. mm Hg | Weight of Fraction |
|---|---|---|---|---|
| 1 | 31–94 | 70–157 | 3.0 | 22.7 |
| 2 | 94–128 | 157–168 | 3.0 | 5.1 |
| 3 | 128–130 | 168–200 | .8 | 53.5 |
| 4 | 130–195 | 200–227 | .8 | 59.8 |

53.5 grams of product is collected. The GLC profile for this product is set forth in FIG. 23. Fraction 3 resulting from the fractional distillation has a GLC profile as set forth in FIG. 24. The NMR spectrum for fraction 3 is set forth in FIG. 25. Fraction 3 contains the isomers:

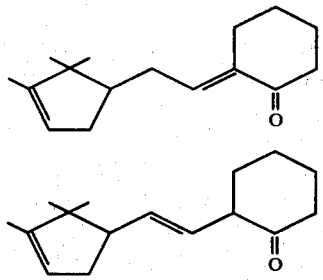

EXAMPLE IIB

PREPARATION OF CAMPHOLENYLIDENE CYCLOHEXANOL

REACTION:

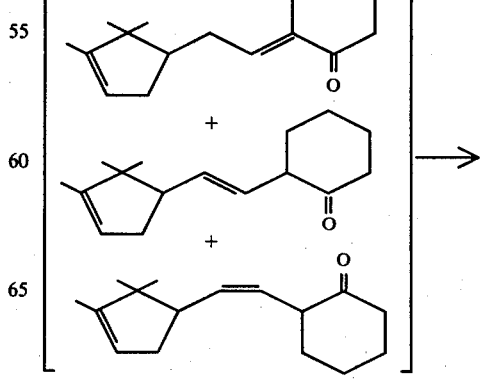

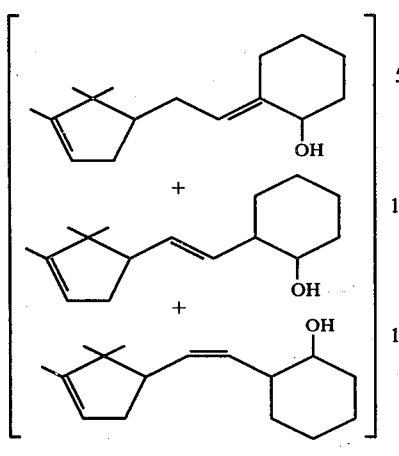

In a 250 ml three-necked reaction flask is placed a solution of 52 grams of campholenylidene cyclohexanone, fraction 3 according to Example IIA (0.22 moles) in 50 ml of anhydrous methanol. To this solution 3.5 grams (0.092 moles) of sodium borohydride dissolved in 20 ml of anhydrous methanol is added over a period of 30 minutes while maintaining the reaction mixture at 20°–23° C. The reaction mass is then stirred at room temperature for a period of 4 hours. 10% acetic acid is added dropwise (100 ml) over a period of 5 minutes at about 15° C. The reaction mass is then stirred for another 10 minutes and the aqueous layer is separated from the organic layer. The organic layer is washed with 100 ml 10% acetic acid and washed neutral with saturated sodium bicarbonate. The reaction mass is then distilled on a micro-vigreaux column yielding the following fractions:

| No. | Vapor Temp (°C.) | Liquid Temp (°C.) | Vac. mm Hg | Wt. of Fraction |
|---|---|---|---|---|
| 1 | 121–135 | 149–149 | 3 | 2 |
| 2 | 135–143 | 149–158 | 3 | 14.9 |
| 3 | 143 | 158–162 | 3 | 11.8 |
| 4 | 143 | 162–173 | 3 | 7.1 |
| 5 | 143 | 173–230 | 3 | 6 |

FIG. 26 is the GLC profile for fracton 2 of the reaction product.

FIG. 27 is the NMR spectrum for fraction 2.

Fraction 2 contains the following compounds having the structures:

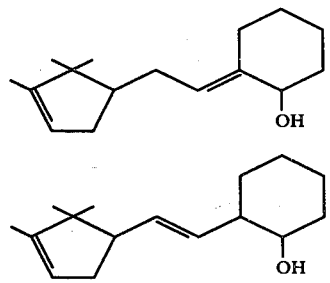

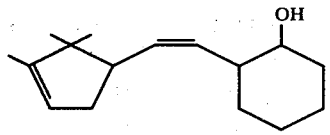

EXAMPLE IIIA

PREPARATION OF ALPHA-CAMPHOLENYLIDENE ACETONE

REACTION:

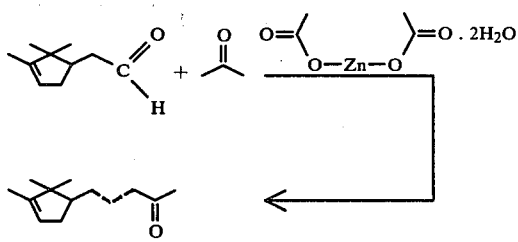

wherein one of the dashed lines is a carbon-carbon single bond and the other of the dashed lines is a carbon-carbon double bond.

Into a 2 liter autoclave equipped with heater and stirrer are placed 76 grams (0.5 moles) of campholenic aldehyde, 290 grams (5.0 moles) of acetone and 22 grams (0.1 moles) of zinc acetate dihydrate. The autoclave is sealed and heated at a temperature of 180° C. for 10 hours wherein the pressure rises and is maintained at between 320 and 340 psig. At the end of the 10 hour period the autoclave contents are cooled and filtered through Supercel. The filtrate is washed with 100 ml saturated sodium chloride solution and the crude is distilled (rushed over) through a "micro distillation column" yielding the following fractions:

| No. | Vapor Temp (°C.) | Liquid Temp (°C.) | Vac. mm Hg | Wt. of Fraction |
|---|---|---|---|---|
| 1 | 31–33 | 42–82 | 30 | 4.5 |
| 2 | 33–45 | 82–110 | 30 | 4.9 |
| 3 | 45–68 | 110 | 2.5 | 5.0 |
| 4 | 68–104 | 110–118 | 3.0 | 18.4 |
| 5 | 104–108 | 118–125 | 3.0 | 13.4 |
| 6 | 108 | 128–142 | 3.0 | 14.3 |
| 7 | 108–118 | 142–182 | 3.0 | 7.0 |
| 8 | 118–137 | 182–205 | 2.0 | 2.3 |

The reaction product is then subjected to gas liquid chromotography and the GLC profile exists in two major peaks, peak A and peak B. The NMR spectrum for peak A is set forth at FIG. 28. The infrared spectrum for peak A is set forth in FIG. 29. The NMR spectrum for peak B is set forth in the FIG. 30. The IR spectrum for peak B is set forth in FIG. 31. Peak A contains compounds having the structures:

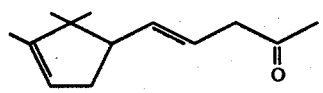

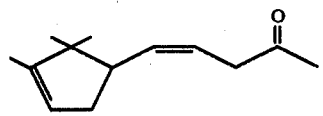

and has the following NMR assignments:

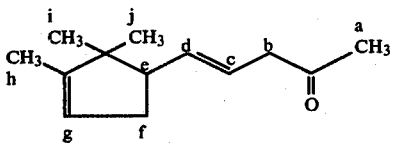

| a - 2.10 ppm (s) | | 6 H |
|---|---|---|
| e,f - 2.10 (m) | | |
| b - 3.14 (d) | | 2 H |
| c,d - 5.59 (m) | | 2 H |
| g - 5.23 (broad) | | 1 H |
| h - 1.59 (allylic coupling) | | 3 H |
| i,j - 0.98, (2 singlets) 0.78 | | 6 H |

Peak B contains compounds having the structures:

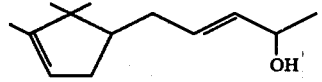

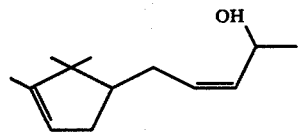

and has the following NMR assignments:

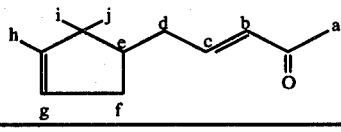

| a - 2.20 ppm (s) | | 8 H |
|---|---|---|
| d,e,f - 1.75-2.0 (m) | | |
| b,c - 5.8-7.0 (m) | | 2 H |
| g - 5.35 (broad) | | 1 H |
| h - 1.59 (allyllic coupling) | | 3 H |
| i,j - 0.98, 0.78 (2 singlets) | | 6 H |

EXAMPLE IIIB

PREPARATION OF 5(2,2,3-TRIMETHYL-3-CYCLOPENTEN-1-YL)-3-PENTEN-2-OL

REACTION:

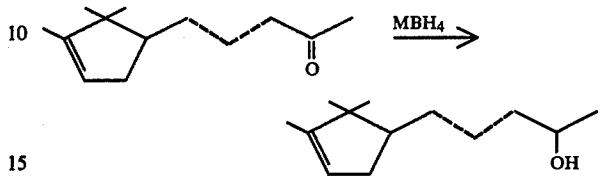

wherein one of the dashed lines is a carbon-carbon single bond and the other of the dashed lines is a carbon-carbon double bond and wherein M is sodium.

Into a 250 ml reaction flask equipped with stirrer thermometer reflux condenser are placed fractions 4, 5 and 6 resulting from the distillation of the reaction product of Example IIIA (46 grams or 0.24 moles); a mixture of ketones having the structures:

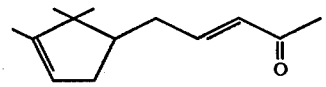

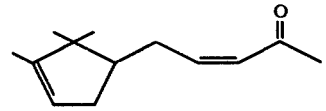

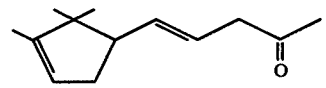

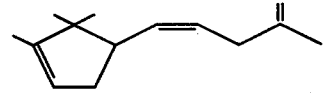

dissolved in 50 ml anhydrous methanol. To this solution is added a solution of 4.6 grams (0.12 moles) of sodium borohydride dissolved in 15 ml anhydrous methanol over a period of 8 minutes while maintaining the reaction mass at a temperature of 25°-40° C. The reaction mass is then stirred at 13°-19° C. for a period of one hour. The reaction mass is then maintained for a period of 12 hours at room temperature. At the end of the 12 hour period 50 ml 10% acetic acid solution is added while maintaining the reaction temperature at 5° C. The resulting organic layer is then washed with saturated sodium bicarbonate followed by saturated sodium chloride solution. The resulting product is then distilled yielding the following fractions:

| No. | Vapor Temp (°C.) | Liquid Temp (°C.) | Vac. mm Hg | Wt. of Fraction |
|---|---|---|---|---|
| 1 | 95-98 | 107-112 | 2 | 2.3 |
| 2 | 98-106 | 112-117 | 2 | 5.7 |
| 3 | 160-110 | 117-120 | 2 | 8.8 |
| 4 | 110 | 120 | 2 | 6.2 |
| 5 | 110-112 | 120-147 | 2.7 | 7.2 |
| 6 | 112-98 | 147-144 | 2.6 | 3.7 |

The total weight of product is 31.6 grams.

The GLC profile contains two major peaks, peak A and peak B. FIG. 32 is the NMR spectrum for peak A. FIG. 33 is the NMR spectrum for peak B. FIG. 34 is the infrared spectrum for peak B.

Peak A is given the following NMR assignments:

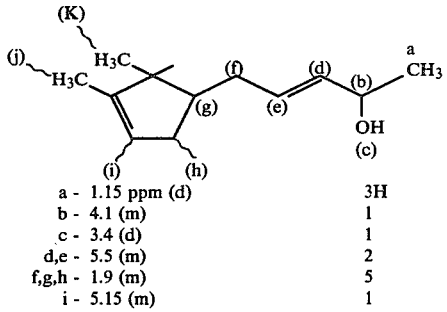

| a - 1.15 ppm (d) | 3H |
| b - 4.1 (m) | 1 |
| c - 3.4 (d) | 1 |
| d,e - 5.5 (m) | 2 |
| f,g,h - 1.9 (m) | 5 |
| i - 5.15 (m) | 1 |
| j - 1.55 (allylic coupling) | 3 |
| k,l 0.80, 0.95 (singlets) | 6 |

The NMR assignments for peak B are as follows:

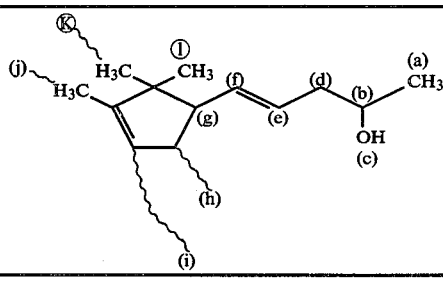

| a - 1.1 ppm (d) | 3H |
| k,l - 0.75, 0.94 (singlets) | 6H |
| j - 1.55 (allylic coupling) | 3H |
| d,g,h - 2.15 (m) | 5H |
| c - 3.25 (d) | 1H |
| b - 3.7 (m) | 1H |
| i - 5.15 (m) | 1H |
| e,f - 5.47 (m) | 2H |

EXAMPLE IVA

PREPARATION OF 6(2,2,3-TRIMETHYL-3-CYCLOPENTEN-1-YL)-4-METHYL-4 (AND 5) HEXEN-3-ONES

REACTION:

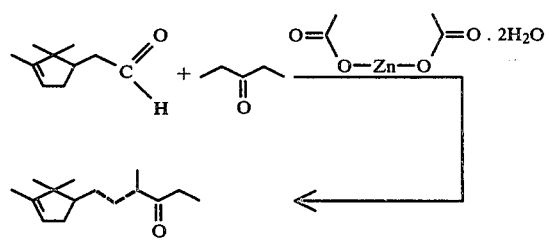

Into an autoclave are charged the following ingredients:
Campholenic aldehyde (76 grams; 0.5 moles)
3-pentanone (430 grams; 5.0 moles)
Zinc acetate dihydrate (22 grams; 0.1 moles)

The autoclave is sealed and heated to 190° C. for a period of 10 hours maintaining the pressures thereof at 160-185 psig. After cooling, solids in the reaction mass are filtered and the crude product is washed neutral with saturated sodium bicarbonate and saturated sodium chloride. After the recovery of unreacted 3-pentanone, the reaction mass product residue is distilled under 3 mm Hg pressure yielding 78.8 grams of crude product.

Redistillation using a 6 inch micro-vigreux column yielded the following fractions:

| No. | Vapor Temp (°C.) | Liquid Temp. (°C.) | Vac. mm Hg | Wt. of Fraction |
|---|---|---|---|---|
| 1 | 25-58 | | 3 | 1.4 |
| 2 | 58 | 97 | 3 | 6.8 |
| 3 | 58-73 | 97-121 | 3 | 1.9 |
| 4 | 73-109 | 121-130 | 2.8 | 11.5 |
| 5 | 109-118 | 130-133 | 2.8 | 8.1 |
| 6 | 118-119 | 133 | 2.8 | 12.7 |
| 7 | 119 | 133-134 | 2.8 | 7.3 |
| 8 | 119 | 134 | 2.8 | 13.2 |
| 9 | 119-123 | 134-135 | 2.8 | 8.4 |
| 10 | 123 | 135-136 | 2.8 | 5.9 |
| 11 | 123-124 | 136-187 | 2.8 | .5 |

FIG. 35 is the GLC profile for bulked fractions 4-11. The two major peaks represent compounds having the following structures:

Peak A

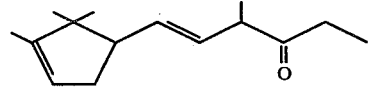

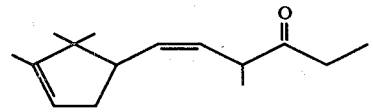

Peak B

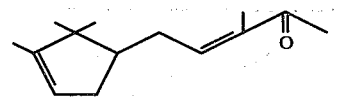

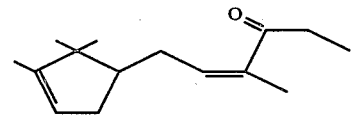

FIG. 36 is the NMR spectrum for peak A of the reaction product produced according to Example IVA containing compounds having the structures:

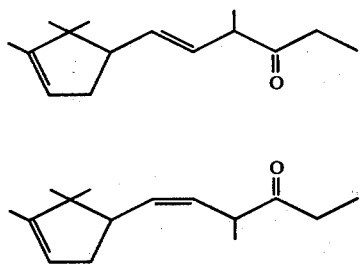

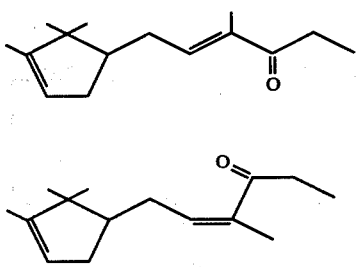

FIG. 37 is the infrared spectrum for peak A of the reaction product produced according to Example IVA.

FIG. 38 is the NMR spectrum for the reaction product of Example IVA peak B.

FIG. 39 is the infrared spectrum for peak B of the reaction product of Example IVA containing the compounds:

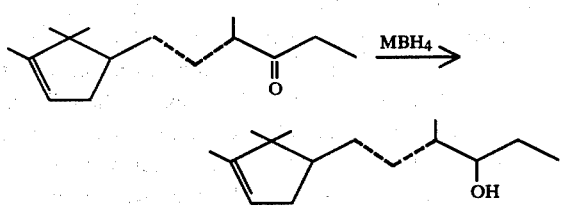

EXAMPLE IVB

PREPARATION OF 6-(2,2,3-TRIMETHYLCYCLOPENTEN-1-YL)-4-METHYL-4 (AND 5)HEXEN-3-OL

REACTION:

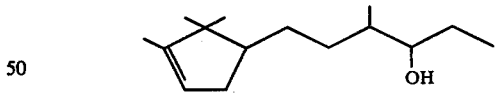

wherein one of the dashed lines is a carbon-carbon single bond and the other of the dashed lines is a carbon-carbon double bond and M is sodium.

Into a 150 ml flask equipped with stirrer, thermometer, reflux condenser and heating mantle are placed 5.7 grams (0.15 moles) of sodium borohydride in 10 ml of anhydrous isopropanol. The ketone reaction product (fractions 4-11 resulting from the fractionation) produced according to Example IVA (66.5 grams; 0.3 moles) admixed with 70 ml isopropyl alcohol is then added to the sodium borohydride isopropyl alcohol solution while maintaining the temperature thereof at 7°-10° C. The reaction mass is then stirred at a temperature of between 7° and 26° C. for a period of 9.5 hours. At the end of the 9.5 hour period the reaction mass is quenched with a 10% aqueous acetic acid solution (50 ml) while maintaining the temperature at 0° C. The reaction mass is then washed neutral with aqueous sodium bicarbonate followed by aqueous sodium chloride and then distilled yielding the following fractions:

| No. | Vapor Temp. (°C.) | Liquid Temp. (°C.) | Vac. | Wt. of Fraction |
|---|---|---|---|---|
| 1 | 90-125 | 130-133 | 2.5-2.2 | 1.6 |
| 2 | 112-126 | 133 | 2.2 | 3.8 |
| 3 | 126 | 133-134 | 2.2 | 5.4 |
| 4 | 126-127 | 134-135 | 2.2 | 5.0 |
| 5 | 127-128 | 135 | 2.2 | 5.8 |
| 6 | 128 | 135-137 | 2.2 | 6.3 |
| 7 | 128 | 137-138 | 2.2 | 6.8 |
| 8 | 128-129 | 138-140 | 2.2 | 6.3 |
| 9 | 129-130 | 140-160 | 2.2 | 6.6 |
| 10 | 130 | 160-175 | 2.2 | 0.4 |

The reaction mass is then analyzed using GLC (carbowax 10 ft.×¼ inch column at 220° C., isothermal) and NMR, IR, mass spectral analyses yield the information that the resulting product has the structures:

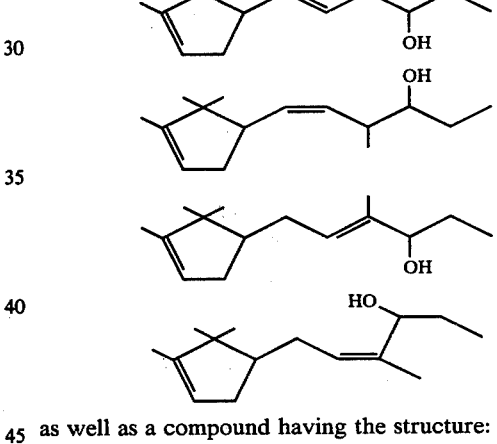

as well as a compound having the structure:

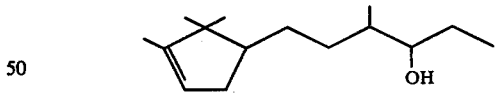

according to the GLC profile the reaction mass contains 21% by weight of compounds having the structures:

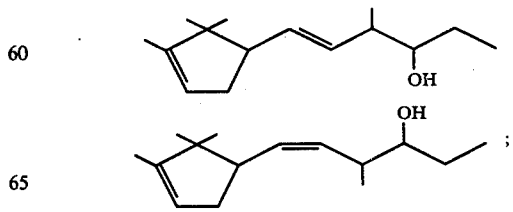

62.0% by weight of compounds having the structures:

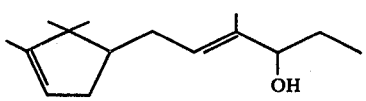

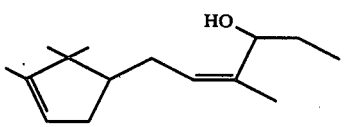

and 14.0% by weight of compound having the structure:

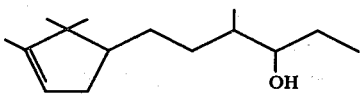

The GLC profile is set forth in FIG. 40 wherein peak A and peak B are for compounds having the structures:

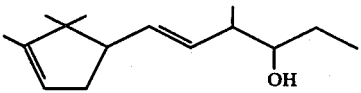

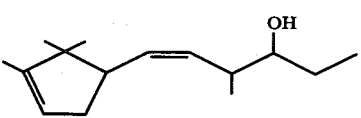

and peak C is for compound having the structure:

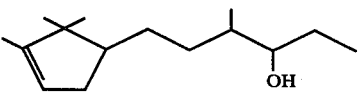

and peak D is for compounds having the structures:

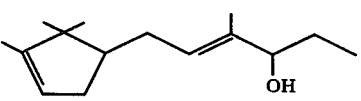

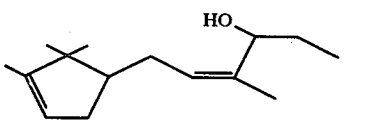

FIG. 41 is the NMR spectrum for peak D containing compounds having the structures:

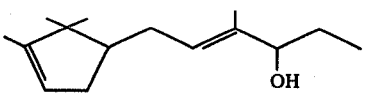

EXAMPLE VA

PREPARATION OF CAMPHOLENYLIDENE CYCLOPENTANONE

REACTION:

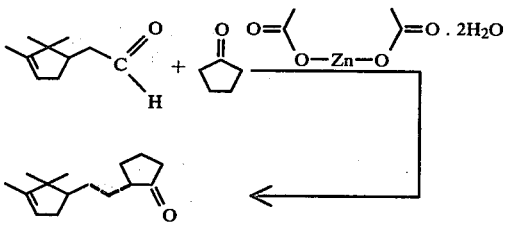

wherein one of the dashed lines is a carbon-carbon single bond and the other of the dashed lines is a carbon-carbon double bond.

Into an autoclave are charged the following ingredients:

Campholenic aldehyde (76 grams:0.5 moles)
Cyclopentanone (425 grams; 5.0 moles)
Zinc acetate dihydrate (22 grams; 0.1 moles) The autoclave is sealed and heated to 190° C. for a period of 10 hours maintaining the pressures thereof at 160–185 psig. After cooling, the solids in the reaction mass are filtered and the crude product is washed neutral with saturated sodium bicarbonate and saturated sodium chloride. After recovery of unreacted cyclopentanone, the reaction mass product residue is distilled under 3 mm Hg pressure. Redistillation using a 6 inch micro-vigreux column yielded the following fractions:

| No. | Vapor Temp. (°C.) | Liquid Temp (°C.) | Vac. mm Hg |
| --- | --- | --- | --- |
| 1 | 105–105 | 155–169 | 4.8 |
| 2 | 125 | 155 | 2.5 |
| 3 | 132 | 161 | 1.2 |
| 4 | 170 | 161 | 1.8 |
| 5 | 203 | 170 | 1.8 |

FIG. 42 is the NMR spectrum for the reaction product of this Example containing compounds having the structures:

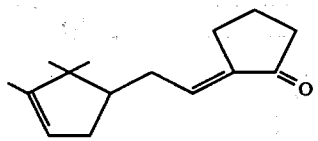

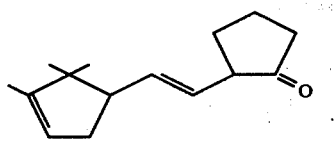

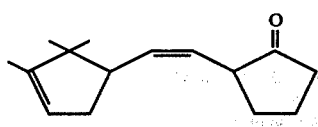

FIG. 43 is the infrared spectrum for the reaction product of this Example containing compounds having the structures:

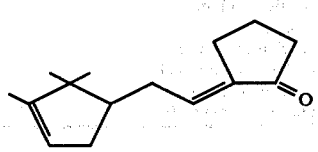

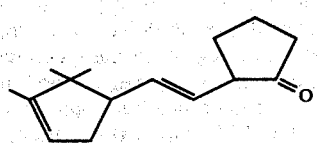

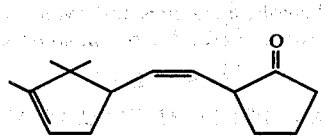

EXAMPLE VB

PREPARATION OF CAMPHOLENYLIDENE CYCLOPENTANOL

REACTION:

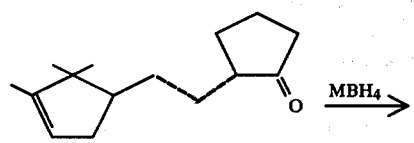

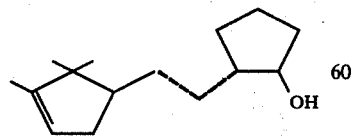

wherein one of the dashed lines is a carbon-carbon single bond and the other of the dashed lines is a carbon-carbon double bond and M is sodium.

Into a 150 ml flask equipped with stirrer, thermometer, reflux condenser and heating mantle are placed 1.52 grams (0.04 moles) of sodium borohydride in 20 ml of anhydrous isopropanol. The ketone reaction product (fractions 3, 4 and 5 resulting from the fractionation) produced according to Example VA (21 grams; 0.1 moles) is then added to the sodium borohydride/isopropyl alcohol solution while maintaining the temperature at 20° C. The reaction mass is then stirred at room temperature for a period of 8 hours. At the end of the 8 hours period the reaction mass is quenched with 10% aqueous acetic acid solution (25 ml). The reaction mass is then washed neutral with aqueous sodium bicarbonate followed by toluene in order to aid separation. The reaction mass is then microdistilled at 124° C. vapor temperature (144° C. liquid temperature) at 2.2 mm Hg pressure yielding 33 grams of reaction product containing compounds having the structures:

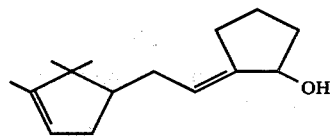

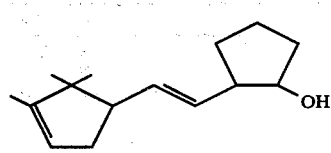

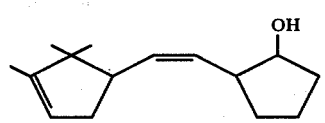

FIG. 44 is the NMR spectrum for the reaction product of Example VB containing compounds having the structures:

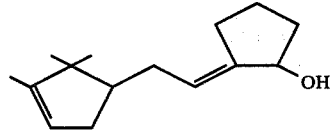

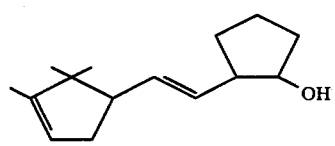

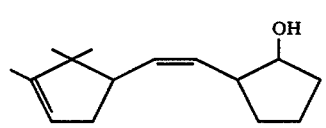

FIG. 45 is the infrared spectrum for the reaction product of Example VB containing compounds having the structures:

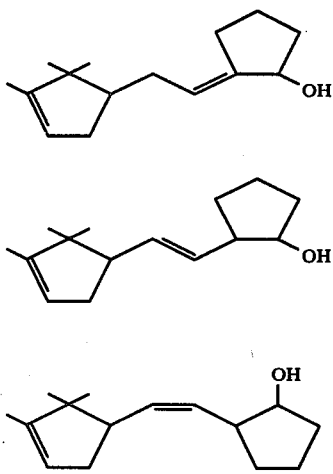

EXAMPLE VI

The following four synthetic sandalwood oil formulations are produced:

| Ingredient | VIA | VIB | VIC | VID |
|---|---|---|---|---|
| Amyrus Oil | 100 | 100 | 100 | 100 |
| Amyrus Acetate | 220 | 220 | 220 | 220 |
| Cedarwood Oil | 150 | 150 | 150 | 150 |
| Trans decahydro beta-naphthol Formate | 100 | 100 | 100 | 100 |
| Guaiophene (1% in diethyl phthalate) | 50 | 50 | 50 | 50 |
| Eugenol (10% in diethyl phthalate) | 50 | 50 | 50 | 50 |
| Galaxolide ® (2.5% in diethyl phthalate) | 30 | 30 | 30 | 30 |
| Geranyl Phenyl Acetate | 50 | 50 | 50 | 50 |
| Mixture of generic compounds defined by the generic structure 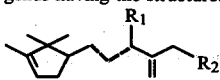 OH (wherein one of the dashed lines is a carbon-carbon single bond and the other of the dashed lines is a carbon-carbon double bond and one of $R_1$ or $R_2$ is methyl and the other of $R_1$ or $R_2$ is hydrogen) produced according to Example IC. | 250 | | | |
| Mixture of compounds having having the structures: 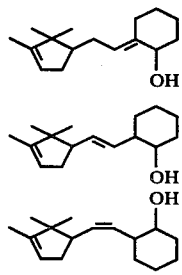 produced according to Example IIB | | 250 | | |
| Mixture of compounds having the having the structures: | | | 250 | |

-continued

| Ingredient | VIA | VIB | VIC | VID |
|---|---|---|---|---|
| produced according to Example IIIB | | | | |
| Mixture of compounds each of which is defined within the genus having the structure:  wherein one of the dashed lines is a carbon-carbon single bond and the other of the dashed lines is a carbon-carbon double bond wherein one $R_1$ or $R_2$ is methyl and the other of $R_1$ or $R_2$ is hydrogen produced according to Example IB. | | | | 250 |

The addition of 25% of the 2,2,3-trimethyl-3-cyclopentene-1-ylalkenyl and alkylidene secondary alkanols, alkanones and cycloalkanols to the sandalwood formulation contributes the main sandalwood note to the fragrance. The odor of the fragrance in each of the cases VIA, VIB, VIC and VID without said 2,2,3-trimethyl-3-cyclopentene-1-ylalkenyl and alkylidene secondary alkanols, alkanones and cycloalkanols is far distant from the desired odor of sandalwood.

EXAMPLE VII

SANDAL PERFUME FORMULATION

The following mixture is prepared:

| Ingredients | Parts by Weight |
|---|---|
| 1',2',3',4',5',6',7',8'-octahydro-2',3',8',8',-tetramethyl-2'-aceto-naphthone isomer mixture produced according to the process of Example VII of Application for U.S. Letters Pat. No. 434,948 filed on January 21, 1974 (now U.S. Pat. No. 3,911,018 issued on October 7, 1975). | 540 |
| Cedrenal - (A tricyclic sesquiterpinic aldehyde derived from cedrene, having the structure:  produced according to the process of U.S. Pat. Application 260,537 filed on June 7, 1972 (now U.S. Pat. No. 3,869,516, issued on March 4, 1975) (corresponding to published Dutch Appln. 7,307,849 laid open for public inspection on December 11, 1973). | 90 |

| Ingredients | Parts by Weight |
|---|---|
| Eugenol (1% in ethyl alcohol) | 54 |
| 2,5,5-trimethyl acetyl cycloheptane produced according to Example I of U.S. Pat. Application 349,180 filed on April 9, 1973 (now U.S. Pat. No. 3,869,411 issued on March 4, 1975). | 180 |
| Borneol (1% in ethyl alcohol) | 18 |
| Hexahydro-4,7-methanoindane-2-carboxaldehyde | 18 |
| Mixture of compounds having the structures: 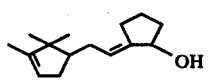 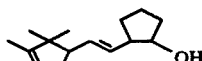 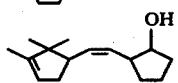 produced according to Example VB. | 100 |

The mixture of compounds produced according to Example VB imparts the woody, sandalwood-like note to the instant formulation, also lending to it some "cyclamal ®-like" and "lilial ®-like character".
®Registered trademark of Givaudan Corporation. Cyclamal is 2-methyl-3-(paraisopropylphenal)propenyl aldehyde described in monograph numbers 758 of "Perfume and Flavor Chemicals" (aroma chemicals) Vol. 1 by Steffen Arctander. Lilial is paratertiary butyl alpha-methyl hydrous synamic aldehyde and is described in monograph 496 of "Perfume and Flavor Chemicals" (aroma chemicals) Vol. I by Steffen Arctander.

EXAMPLE VIII

PREPARATION OF A SOAP COMPOSITION

A total of 100 grams of soap chips produced from unperfumed sodium base toilet soap made by tallow and coconut oil are mixed with 1 gram of the perfume composition produced according to Example VIA until a substantially homogeneous composition is obtained. The soap composition manifests a characteristic "sandal cologne" aroma having intense musky nuances. Similar sandal cologne aroma containing soaps are produced using the compositions of Examples VIB, VIC, VID and VII.

EXAMPLE IX

PREPARATION OF A SOAP COMPOSITION

A total of 100 grams of soap chips produced from unperfumed sodium base toilet soap made from tallow and coconut oil is mixed with 1 gram of a mixture of compounds defined by the generic structures:

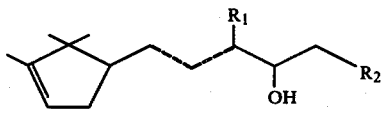

wherein one of the dashed lines is a carbon-carbon single bond and the other of the dashed lines is a carbon-carbon double bond and one of $R_1$ or $R_2$ is methyl and the other of $R_1$ or $R_2$ is hydrogen produced according to Example IC until a substantially homogenous composition is obtained. The soap composition manifests a powerful sandalwood aroma with nutty and oily nuances and also have an intense musky topnote.

EXAMPLE X

PREPARATION OF A SOLID DETERGENT COMPOSITION

A total of 100 grams of a detergent powder sold under the trademark "RINSO"[R] are mixed with 0.15 grams of a perfume composition containing the mixture of Example III until a substantially homogeneous composition having a "sandal cologne" fragrance with woody notes and a "cyclamal-lilial" character is obtained.

EXAMPLE XI

PREPARATION OF COLOGNE AND HANDKERCHIEF PERFUME

The composition of Example III is incorporated into a cologne having a concentration of 2.5% in 85% aqueous ethanol; and into a handkerchief perfume in a concentration of 20% (in 95% ethanol). The use of the composition of Example III affords a distinct and definite "sandal cologne" aroma having a warm sandalwood-like character to the handkerchief perfume and to the cologne.

EXAMPLE XII

PREPARATION OF COLOGNE AND HANDKERCHIEF PERFUME

A mixture of compounds defined by the generic structure:

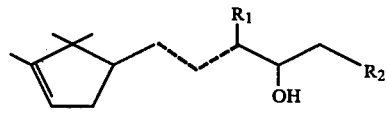

wherein one of the dashed lines is a carbon-carbon single bond and the other of the dashed lines is a carbon-carbon double bond and one of $R_1$ or $R_2$ is methyl and the other of $R_1$ or $R_2$ is hydrogen produced according to Example IC is incorporated into colognes having concentrations of 2.0%, 2.5%, 3.0%, 3.5%, 4.0%, 4.5% and 5.0% in 85% aqueous foodgrade ethanol; and into handkerchief perfumes in concentrations of 15%, 20%, 25%, 30% and 35% (in 95% foodgrade ethanol). The uses of the mixture of compounds defined by the generic structure:

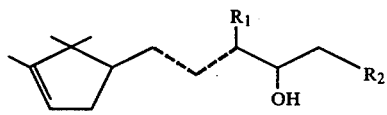

produced according to Example IC afford a distinct and definite sandalwood aroma with nutty and oily nuances and intense musky topnotes to the handkerchief perfumes and to the colognes prepared as above.

EXAMPLE XIV

PERFUMED LIQUID DETERGENT

Concentrated liquid detergents with strong cedarwood and sandalwood aromas are prepared containing 0.10%, 0.15% and 0.20% of a mixture of compounds having the structures:

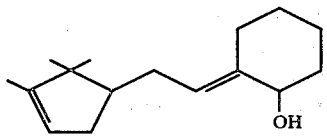

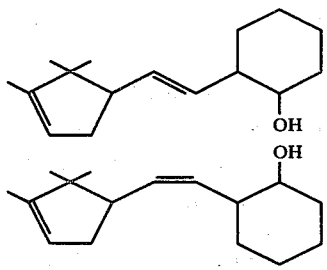

prepared according to Example IIB. The liquid detergents are prepared by adding and homogeneously mixing the appropriate quantity of said mixture of compounds prepared according to Example IIB in the liquid detergent described according to British Patent No. 1,092,149 containing 2% by weight ethyl/maleic anhydride copolymer (specific viscosity 0.5-1.0) and 0.42 weight percent methyl vinyl ethyl/maleic anhydride copolymer (specific viscosity 0.4) as stabilizer and 8% by weight of a sultaine detergent. The detergents all possess strong cedarwood, sandalwood aroms with sweet nuances, the intensity increasing with greater concentration of compounds prepared according to Example IB. A similar effect is obtained using the separate constituents of the composition prepared according to Example IIB with these detergents.

EXAMPLE XV

PREPARATION OF A DETERGENT COMPOSITION

A total of 100 grams of a detergent powder (essentially water soluble non-ionic detergent and stable laundry enzyme as described in U.S. Pat. No. 3,953,353 issued on April 27, 1976) is mixed with 0.15 grams of compound defined by the structure:

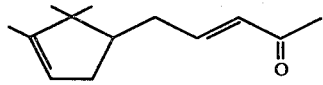

until a substantially homogeneous composition is obtained. This composition has an excellent floral ionone violets-like aroma with fatty rue oil nuances.

EXAMPLE XVI

PREPARATION OF A SOAP COMPOSITION

A marble soap is prepared according to British Patent 1,507,705 issued on Apr. 19, 1978 producing 0.15 grams of the compound having the structure:

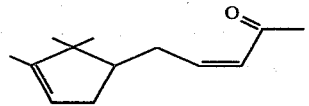

into 100 grams of soap just prior to extrusion. After manufacture the soap possesses a pleasant fruity, ionony, green, buttery, aroma.

What is claimed is:

1. A process for preparing 2,2,3-trimethyl-3-cyclopenten-1-ylalkenyl and alkylidene alkanones and cycloalkanones according to the reaction scheme:

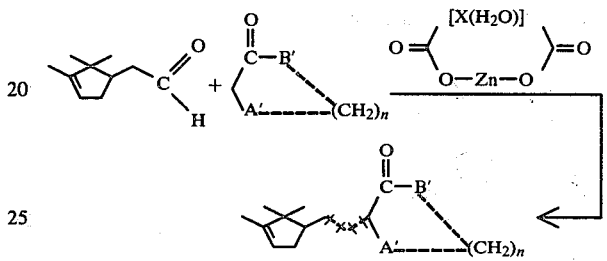

wherein x is 0 or 2;
wherein one of the lines ++++++ is a carbon-carbon double bond and the other of the lines ++++++ is a carbon-carbon single bond; wherein A' is one of hydrogen, $C_3$, $C_2H_5$ or —$CH_2$— and B' is hydrogen, $CH_3$, $C_2H_5$ or —$CH_2$—; n is 0, 1 or 2; each of the dashed lines represents a carbon-carbon single or no bond; with the proviso that A' and B' is both —$CH_2$— when n=1 or n=2 and the dashed line represents a carbon-carbon single bond; and A' is hydrogen and B' is $C_2H_5$ or $CH_3$ or A' is $CH_3$ and B' is $CH_3$ or $C_2H_5$ and n is 0 and the dashed line represents no bond comprising the steps of intimately admixing campholenic aldehyde with a ketone having the structure:

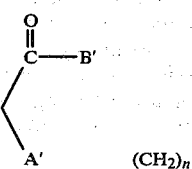

in the presence of a catalyst selected from the group consisting of zinc acetate and zinc acetate dihydrate; said reaction being carried out in the liquid phase at an elevated temperature sufficient to produce the desired product.

2. The process of claim 1 wherein the ketone reactant is acetone.

3. The process of claim 1 wherein the ketone reactant is cyclohexanone.

4. The process of claim 1 wherein the ketone reactant is methyl ethyl ketone.

5. The process of claim 1 wherein the ketone reactant is 3-pentanone.

6. The process of claim 1 comprising the additional step of carrying out the reaction scheme:

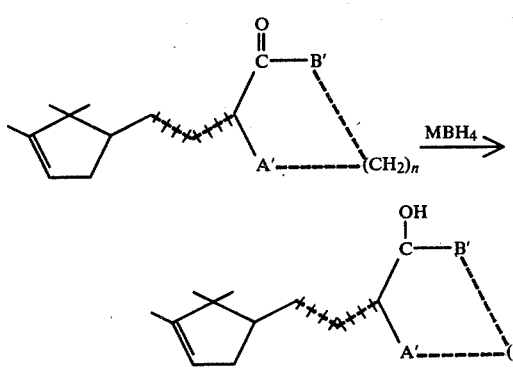

wherein M is alkaline metal selected from the group consisting of potassium and sodium, comprising the steps of admixing an alkaline metal borohydride with the ketone reaction product having the structure:

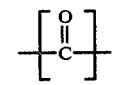

wherein X has the structure:

$$\left[\begin{array}{c} O \\ \| \\ C \end{array}\right]$$

7. The process of claim 1 wherein the mole ratio of catalyst:ketone reaction varies from about 0.05:1 up to about 1:1; and the reaction temperature being from about 100° C. up to about 250° C.

8. The process of claim 1 wherein the mole ratio of catalyst:ketone reaction varies from about 0.05:1 up to about 1:1, the mole ratio of ketone:aldehyde reactants varies from about 1:1 up to about 10:1; and the reaction temperature varying from about 100° C. up to about 250° C.

* * * * *

UNITED STATES PATENT AND TRADEMARK OFFICE
CERTIFICATE OF CORRECTION

PATENT NO. : 4,210,767
DATED : July 1, 1980
INVENTOR(S) : Takao Yoshida, et al

It is certified that error appears in the above-identified patent and that said Letters Patent are hereby corrected as shown below:

Column 52, line 14, after "alkylidene,", add:

---aldehydes,---.

Column 52, line 33, replace "$C_3$" with:

---$CH_3$---.

Column 52, line 43, after the word "ketone", add:

---or aldehyde---.

Column 52, lines 45-50, replace the structure thereat with the structure:

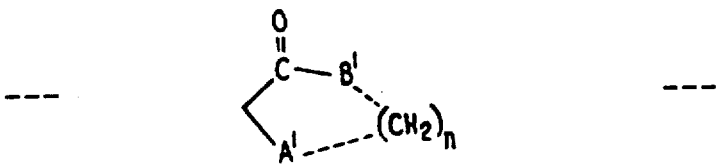

Column 53, line 25, after the word "ketone" add:

---or aldehyde---.

\* \* \* \* \*

In the Abstract, at line 4, after the word "secondary alkanols," add:

---primary alkanols,---.

UNITED STATES PATENT AND TRADEMARK OFFICE
CERTIFICATE OF CORRECTION

PATENT NO. : 4,210,767

DATED : July 1, 1980

INVENTOR(S) : Takao Yoshida, et al

It is certified that error appears in the above-identified patent and that said Letters Patent are hereby corrected as shown below:

Page 2 of the Abstract, right-hand column, replace the reaction at lines 1 and 2 with the reaction:

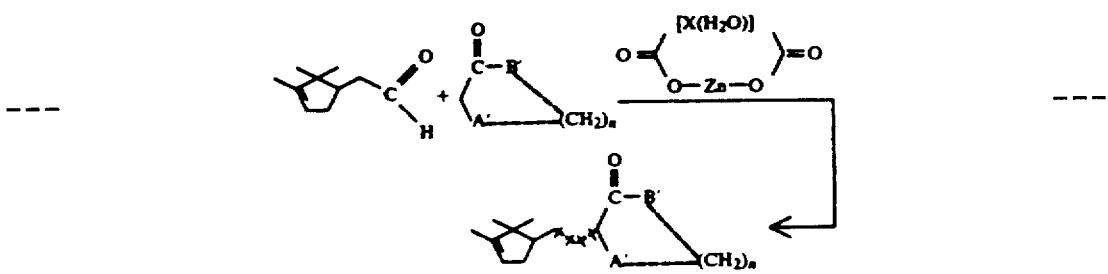

Page 2 of the Abstract, right-hand column, last line, replace "alkaline" with:

---alkali---.

In the Abstract, line 5 (first page) after "alkanones," add:

---aldehydes,---.

Signed and Sealed this

Seventh Day of January 1986

[SEAL]

Attest:

DONALD J. QUIGG

Attesting Officer     Commissioner of Patents and Trademarks